US006987088B2

(12) United States Patent
Dennis

(10) Patent No.: US 6,987,088 B2
(45) Date of Patent: Jan. 17, 2006

(54) COMPOUNDS THAT BIND HER2

(75) Inventor: Mark S. Dennis, San Carlos, CA (US)

(73) Assignee: Genentech, Inc., South Sanfrancisco, CA (US)

( * ) Notice: Subject to any disclaimer, the term of this patent is extended or adjusted under 35 U.S.C. 154(b) by 15 days.

(21) Appl. No.: 10/196,394

(22) Filed: Jul. 15, 2002

(65) Prior Publication Data
US 2003/0171278 A1 Sep. 11, 2003

Related U.S. Application Data

(63) Continuation of application No. 09/609,721, filed on Jun. 30, 2000, now abandoned.
(60) Provisional application No. 60/142,232, filed on Jul. 2, 1999.

(51) Int. Cl.
A01N 37/18 (2006.01)

(52) U.S. Cl. .................. 514/2; 530/300; 530/387.3; 435/69.1; 435/320.1; 435/252.3; 435/325; 435/6; 514/12

(58) Field of Classification Search .............. 514/2; 530/300; 435/69.1, 69.7, 320.1, 252.3, 325, 435/6
See application file for complete search history.

(56) References Cited

U.S. PATENT DOCUMENTS

| 5,116,964 | A |   | 5/1992  | Capon et al.   |         |
|-----------|---|---|---------|----------------|---------|
| 5,279,966 | A | * | 1/1994  | Jessell et al. |         |
| 5,578,482 | A | * | 11/1996 | Lippman et al. | 435/384 |
| 5,624,821 | A |   | 4/1997  | Winter et al.  |         |
| 5,648,260 | A |   | 7/1997  | Winter et al.  |         |
| 5,869,618 | A |   | 2/1999  | Lippman et al. |         |
| 5,871,969 | A | * | 2/1999  | Hastings et al.|         |
| 6,414,130 | B1|   | 7/2002  | Doherty et al. |         |

FOREIGN PATENT DOCUMENTS

| WO | WO 98/17797 | 4/1998  |
| WO | WO 98/57989 | 12/1998 |
| WO | WO 99/14323 | 3/1999  |
| WO | WO 99/31140 | 6/1999  |
| WO | WO 99/39729 | 8/1999  |
| WO | WO 00/24782 | 5/2000  |
| WO | WO 01/61356 | 8/2001  |

OTHER PUBLICATIONS

Seq IG No.:15 (sequence search results only).*
Seq IG No.:8 (sequence search results only).*
Arap et al., "Cancer Treatment by Targeted Drug Delivery to Tumor Vasculature in a Mouse Model" *Science* 279:377–380 (1998).

Baselga et al., "Phase II Study of Weekly Intravenous Recombinant Humanized Anti–p185$^{HER2}$ Monoclonal Antibody in Patients With HER2/neu–Overexpressing Metastatic Breast Cancer" *J. Clin. Oncol.* 14(3):737–744 (Mar. 1996).

Clackson and Wells, "In vitro selection from protein and peptide libraries" *Trends Biotechnol.* 12:173–184 (1994).

Dennis and Lazarus, "Kunitz Domain Inhibitors of Tissue Factor—Factor VIIa; I. Potent Inhibitors Selected from Libraries by Phage Display" *Journal of Biological Chemistry* 269(35):22129–22136 (1994).

Dennis and Lazarus, "Kunitz Domain Inhibitors of Tissue Factor—Factor VIIa; II. Potent and Specific Inhibitors by Competitive Phage Selection" *Journal of Biological Chemistry* 269(35):22137–22144 (1994).

Hudziak et al., "Cell transformation potential of a HER2 transmembrane domain deletion mutant retained in the endoplasmic reticulum" *Journal of Biological Chemistry* 266:24109–24115 (1991).

Jones et al., "Binding specificities and affinities of egf domains for ErbB receptors" *FEBS Letters* 447:227–231 (1999).

Lowman and Wells, "Affinity Maturation of Human Growth Hormone by Monovalent Phage Display" *J. Mol. Biol.* 234:564–578 (1993).

Lowman et al., "Molecular Mimics of Insulin–Like Growth Factor 1 (IGF–1) for Inhibiting IGF–1: IGF–Binding Protein Interactions." *Biochemistry* 37(25):8870–8878 (1998).

Lowman et al., "Selecting High–Affinity Binding Proteins by Monovalent Phage Display" *Biochemistry* 30(45):10832–10838 (1991).

Lowman, H., "Bacteriophage display and discovery of peptide leads for drug development" *Annual Review of Biophysics and Biomolecular Structure* 26:401–424 (1997).

Lowman, H., "Phage display of peptide libraries on protein scaffolds" *Methods in Molecular Biology*, Chapter 24, 87:249–264 (1998).

(Continued)

*Primary Examiner*—Lorraine Spector
*Assistant Examiner*—Dong Jiang
(74) *Attorney, Agent, or Firm*—Merchant & Gould P.C.

(57) ABSTRACT

The invention provides novel compounds which bind to the human erbB2 gene product (ErbB2, also known as HER2, or c-ErbB-2). In particular aspects, the invention provides for the treatment of disorders characterized by the overexpression of ErbB2 utilizing the novel compounds of the invention. The invention also provides pharmaceutical compositions comprising the novel compounds as well as for their use in research, diagnostic, therapeutic, and prophylactic methods.

26 Claims, 21 Drawing Sheets

OTHER PUBLICATIONS

Pasqualini and Ruoslahti, "Organ targeting in vivo using phage display peptide libraries" *Nature* 380:364–366 (1996).

Seelig et al., "Synthetic mimics of juxtaposed amino– and carboxyl–terminal peptide domains of human γ interferon block ligand binding to human γ interferon receptor" *Chemical Abstracts* (abstract #75131) 120(7):678 (1994).

Seelig et al., "Synthetic Mimics of Juxtaposed Amino– and Carboxyl–terminal Peptide Domains of Human γ Interferon Block Ligand Binding to Human γ Interferon Receptor" *Journal of Biological Chemistry* 269(1):358–363 (1994).

Semba et al., "A v–erbB–related protooncogene, c–erbB–2, is distinct from the c–erbB–1/epidermal growth factorreceptor gene and is amplified in a human salivary gland adenocarcinoma" *Proc. Natl. Acad. Sci. USA* 82:6497–6501 (1985).

Wells and Lowman, "Rapid Evolution of Peptide and Protein Binding Properties in Vitro" *Curr. Opin. Struct. Bio.* 2:597–604 (1992).

Yamamoto et al., "Similarity of protein encoded by the human c–erb–B–2 gene to epidermal growth factor receptor" *Nature* 319:230–234 (1986).

* cited by examiner

```
           230        240        250        260        270
humIgG1    PAPELLGGPSVFLFPPKPKDTLMISRTPEVTCVVVDVSHEDPEVKFNWYV
humIgG2    PAP-PVAGPSVFLFPPKPKDTLMISRTPEVTCVVVDVSHEDPEVQFNWYV
humIgG3    PAPELLGGPSVFLFPPKPKDTLMISRTPEVTCVVVDVSHEDPEVQFKWYV
humIgG4    PAPEFLGGPSVFLFPPKPKDTLMISRTPEVTCVVVDVSQEDPEVQFNWYV
murIgG1    ---TVPEVSSVFIFPPKPKDVLTITLTPKVTCVVVDISKDDPEVQFSWFV
murIgG2A   PAPNLLGGPSVFIFPPKIKDVLMISLSPIVTCVVVDVSEDDPDVQISWFV
murIgG2B   PAPNLEGGPSVFIFPPNIKDVLMISLTPKVTCVVVDVSEDDPDVQISWFV
murIgG3    PPGNILGGPSVFIFPPKPKDALMISLTPKVTCVVVDVSEDDPDVHVSWFV 280        290        300        310        320
humIgG1    DGVEVHNAKTKPREEQYNSTYRVVSVLTVLHQDWLNGKEYKCKVSNKALP
humIgG2    DGVEVHNAKTKPREEQFNSTFRVVSVLTVVHQDWLNGKEYKCKVSNKGLP
humIgG3    DGVEVHNAKTKPREEQFNSTFRVVSVLTVLHQDWLNGKEYKCKVSNKALP
humIgG4    DGVEVHNAKTKPREEQFNSTYRVVSVLTVLHQDWLNGKEYKCKVSNKGLP
murIgG1    DDVEVHTAQTQPREEQFNSTFRSVSELPIMHQDCLNGKEFKCRVNSAAFP
murIgG2A   NNVEVHTAQTQTHREDYNSTLRVVSALPIQHQDWMSGKEFKCKVNNKDLP
murIgG2B   NNVEVHTAQTQTHREDYNSTIRVVSHLPIQHQDWMSGKEFKCKVNNKDLP
murIgG3    DNKEVHTAWTQPREAQYNSTFRVVSALPIQHQDWMRGKEFKCKVNNKALP 330        340        350        360        370
humIgG1    APIEKTISKAKGQPREPQVYTLPPSREEMTKNQVSLTCLVKGFYPSDIAV
                                     D L
humIgG2    APIEKTISKTKGQPREPQVYTLPPSREEMTKNQVSLTCLVKGFYPSDIAV
humIgG3    APIEKTISKTKGQPREPQVYTLPPSREEMTKNQVSLTCLVKGFYPSDIAV
humIgG4    SSIEKTISKAKGQPREPQVYTLPPSQEEMTKNQVSLTCLVKGFYPSDIAV
murIgG1    APIEKTISKTKGRPKAPQVYTIPPPKEQMAKDKVSLTCMITDFFPEDITV
murIgG2A   APIERTISKPKGSVRAPQVYVLPPPEEEMTKKQVTLTCMVTDFMPEDIYV
murIgG2B   SPIERTISKPKGLVRAPQVYTLPPPAEQLSRKDVSLTCLVVGFNPGDISV
murIgG3    APIERTISKPKGRAQTPQVYTIPPPREQMSKKKVSLTCLVTNFFSEAISV 380        390        400        410        420
humIgG1    EWESNGQPENNYKTTPPVLDSDGSFFLYSKLTVDKSRWQQGNVFSCSVMH
humIgG2    EWESNGQPENNYKTTPPMLDSDGSFFLYSKLTVDKSRWQQGNVFSCSVMH
humIgG3    EWESSGQPENNYNTTPPMLDSDGSFFLYSKLTVDKSRWQQGNIFSCSVMH
humIgG4    EWZSNGQPENNYKTTPPVLDSDGSFFLYSRLTVDKSRWQEGNVFSCSVMH
murIgG1    EWQWNGQPAENYKNTQPIMDTDGSYFVYSKLNVQKSNWEAGNTFTCSVLH
murIgG2A   EWTNNGKTELNYKNTEPVLDSDGSYFMYSKLRVEKKNWVERNSYSCSVVH
murIgG2B   EWTSNGHTEENYKDTAPVLDSDGSYFIYSKLNMKTSKWEKTDSFSCNVRH
murIgG3    EWERNGELEQDYKNTPPILDSDGTYFLYSKLTVDTDSWLQGEIFTCSVVH 430        440
humIgG1    EALHNHYTQKSLSLSPGK
humIgG2    EALHNHYTQKSLSLSPGK
humIgG3    EALHNRFTQKSLSLSPGK
humIgG4    EALHNHYTQKSLSLSLGK
murIgG1    EGLHNHHTEKSLSHSPGK
murIgG2A   EGLHNHHTTKSFSRTPGK
murIgG2B   EGLKNYYLKKTISRSPGK
murIgG3    EALHNHHTQKNLSRSPGK
```

FIG. 2A

Percent Identity Among Fc Sequences

|   | 1 | 2 | 3 | 4 | 5 | 6 | 7 | 8 |
|---|---|---|---|---|---|---|---|---|
| 1. humIgG1 | - | 94 | 94 | 94 | 64 | 66 | 63 | 68 |
| 2. humIgG2 |   | - | 93 | 92 | 65 | 63 | 60 | 67 |
| 3. humIgG3 |   |   | - | 91 | 64 | 64 | 61 | 67 |
| 4. humIgG4 |   |   |   | - | 62 | 64 | 61 | 64 |
| 5. murIgG1 |   |   |   |   | - | 65 | 61 | 67 |
| 6. murIgG2A |   |   |   |   |   | - | 77 | 70 |
| 7. murIgG2B |   |   |   |   |   |   | - | 68 |
| 8. murIgG3 |   |   |   |   |   |   |   | - |

FIG. 2B

```
         230       240       250       260       270
humIgG1  PAPELLGGPSVFLFPPKPKDTLMISRTPEVTCVVVDVSHEDPEVKFNWYV
humIgG2  PAP-PVAGPSVFLFPPKPKDTLMISRTPEVTCVVVDVSHEDPEVQFNWYV
humIgG3  PAPELLGGPSVFLFPPKPKDTLMISRTPEVTCVVVDVSHEDPEVQFKWYV
humIgG4  PAPEFLGGPSVFLFPPKPKDTLMISRTPEVTCVVVDVSQEDPEVQFNWYV
                 * * * *                         *    *  *

280       290       300       310       320
humIgG1  DGVEVHNAKTKPREEQYNSTYRVVSVLTVLHQDWLNGKEYKCKVSNKALP
humIgG2  DGVEVHNAKTKPREEQFNSTFRVVSVLTVVHQDWLNGKEYKCKVSNKGLP
humIgG3  DGVEVHNAKTKPREEQFNSTFRVVSVLTVLHQDWLNGKEYKCKVSNKALP
humIgG4  DGVEVHNAKTKPREEQFNSTYRVVSVLTVLHQDWLNGKEYKCKVSNKGLP
                         *    *           *              *

330       340       350       360       370
humIgG1  APIEKTISKAKGQPREPQVYTLPPSREEMTKNQVSLTCLVKGFYPSDIAV
                         D L
humIgG2  APIEKTISKTKGQPREPQVYTLPPSREEMTKNQVSLTCLVKGFYPSDIAV
humIgG3  APIEKTISKTKGQPREPQVYTLPPSREEMTKNQVSLTCLVKGFYPSDIAV
humIgG4  SSIEKTISKAKGQPREPQVYTLPPSQEEMTKNQVSLTCLVKGFYPSDIAV
         * *        *                *

380       390       400       410       420
humIgG1  EWESNGQPENNYKTTPPVLDSDGSFFLYSKLTVDKSRWQQGNVFSCSVMH
humIgG2  EWESNGQPENNYKTTPPMLDSDGSFFLYSKLTVDKSRWQQGNVFSCSVMH
humIgG3  EWESSGQPENNYNTTPPMLDSDGSFFLYSKLTVDKSRWQQGNIFSCSVMH
humIgG4  EWESNGQPENNYKTTPPVLDSDGSFFLYSRLTVDKSRWQEGNVFSCSVMH
             *       *     *                *      *  *

430       440
humIgG1  EALHNHYTQKSLSLSPGK
humIgG2  EALHNHYTQKSLSLSPGK
humIgG3  EALHNRFTQKSLSLSPGK
humIgG4  EALHNHYTQKSLSLSLGK
             * *           *
```

FIG. 3

QVYESWGCIGPGCACLQACL-Z

QVYESWGCIGPGCACLQACLGGGSGGQVYESWGCIGPGCACLQACL-Z
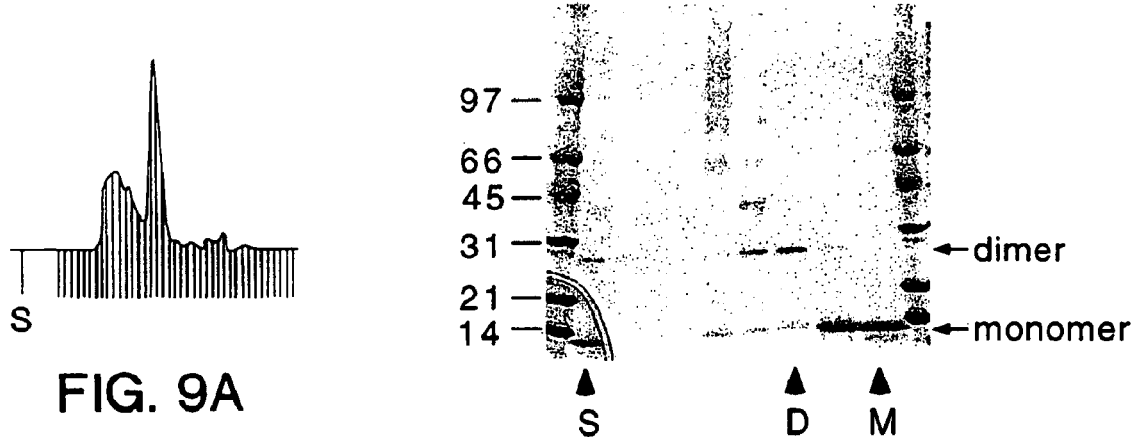
FIG. 9A
FIG. 9B
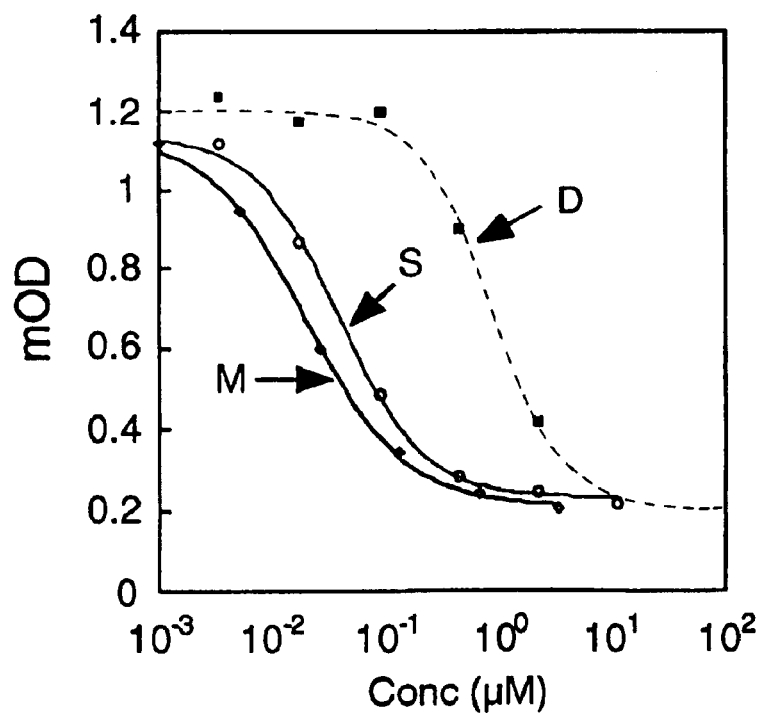
FIG. 9C

FIG. 11

1 = Control Fc (no peptide fusion)
2 = HER2-Fc fusion (1.1 Fl-Fc)

| | 1 | 2 | 3 | 4 | 5 | 6 | 7 | 8 | 9 | 10 | 11 | 12 | 13 | 14 | 15 | 16 | 17 | 18 | 19 |
|---|---|---|---|---|---|---|---|---|---|---|---|---|---|---|---|---|---|---|---|
| Pool 1 | Y | E | V | E | A | W | D | M | G | P | G | C | A | N | L | F | E | A | H |
| 1.1 Consensus | Y | E | F | E | G | W | G | H | C | G | P | G | C | A | Y | L | F | E | A | H |
| Library 1.1.F | – | – | – | E | – | W | – | – | C | G | P | G | C | – | L | – | – | – | – | – |
| 1.1.FC | Y | E | W | E | G | W | G | C | C | G | P | G | C | A | L | F | G | Y |
| 1.1.FN | R | W | D | E | G | W | G | H | C | G | P | G | C | W | L | V | R | K |
| 1.1.FA | Q | R | N | E | A | W | G | H | C | G | P | G | C | M | L | A | E | G |
| 1.1.FM | L | S | P | E | T | W | G | H | C | G | P | G | C | M | L | S | W | R |
| 1.1.FE | E | N | W | E | M | W | G | H | C | G | P | G | C | F | L | E | P | C |
| 1.1.FH | C | I | D | E | T | W | G | H | C | G | P | G | C | E | L | R | K | C |
| 1.1.FB | T | Q | A | E | R | W | G | H | C | G | P | G | C | B | L | M | A | C |
| 1.1.FF | A | P | R | E | V | W | G | H | C | G | P | G | C | A | L | L | R | C |
| 1.1.FI | Q | V | Y | E | S | W | G | H | C | G | P | G | C | R | L | Q | A | C |
| 1.1.FK | R | T | E | E | Q | W | G | H | C | G | P | G | C | E | L | L | S | C |
| 1.1.FD | F | A | G | E | S | W | G | H | C | G | P | G | C | N | L | I | G | C |
| 1.1.FQ | T | A | R | E | P | W | G | H | C | G | P | G | C | S | L | L | A | C |
| 1.1.FS | R | P | H | E | P | W | G | H | C | G | P | G | C | K | L | Q | S | C |
| 1.1.FX | A | S | H | E | V | W | G | H | C | G | P | G | C | A | L | L | A | C |
| 1.1.FY | K | L | N | E | E | W | G | H | C | G | P | G | C | A | L | M | C | C |
| 1.1.FZ | K | L | N | E | D | W | G | H | C | G | P | G | C | – | L | L | – | – |

FIG. 16B

COMPOUNDS THAT BIND HER2

RELATED APPLICATIONS

This application is a continuation application of U.S. patent application Ser. No. 09/609,721, filed under 37 CFR 1.53(b)(1) on 30 Jun. 2000, now abandoned, which claims priority under 35 USC 119(e) to provisional application No. 60/142,232, filed Jul. 2, 1999.

BACKGROUND OF THE INVENTION

1. Field of the Invention

This invention relates to novel compounds which bind to the human erbB2 gene product (ErbB2, also known as HER2, or c-ErbB-2). In particular aspects, the invention relates to the treatment of disorders characterized by the expression of ErbB2 utilizing the novel compounds of the invention. The invention also relates to compositions, such as pharmaceutical compositions, comprising the novel compounds, as well as their use in research, diagnostic, therapeutic, and prophylactic methods.

2. Description of Related Disclosures

Phage display provides a means for generating peptides and protein variants through randomization of specific amino acid residues within a template sequence or by generation of naive peptide libraries (Lowman, H. (1998) Methods Mol. Biol. 87:249–264; Lowman (1997) Annu. Rev. Biophys. Biomol. Struct. 26:401–424). Identification and isolation of displayed proteins or peptides that bind a predetermined target molecule can be achieved through enrichment of displaying phage over non-binding or weakly binding variants on immobilized target molecules (Lowman, H. (1989), supra). Successive rounds of mutagenesis and selection can yield peptide ligands or protein variants with high affinity for cellular receptors (Lowman, H. (1998), supra). The technique has been used to identify peptide motifs that home to, for example, a cellular target (Arap et al., (1998) Science 279:377–380), or to generate affinity improved or matured peptide ligands from native protein binding ligands (Lowman et al., (1991) Biochemistry 30: 10832–10838). Examples of affinity or specificity improved proteins include human growth hormone, zinc fingers, protease inhibitors, atrial natriuretic peptides, and antibodies (Wells, J. and Lowman H. (1992) Curr. Opin. Struct. Biol. 2:597–604; Clackson, T. and Wells, J. (1994) Trends Biotechnol. 12:173–184; Lowman et al., (1991) Biochemistry 30(10):832–838; Lowman et al. and Wells J. (1993) J. Mol. Biol. 234:564–578; Dennis M. and Lazarus R. (1994) J. Biol. Chem. 269(22):137–144).

Utilizing in vivo phage selection, phage display has been used to identify and isolate peptides capable of mediating selective localization to various organs such as brain and kidney (Pasqualini and Ruoslohti (1996) Nature 380:364–366) as well as to identify peptides that home to particular tumor types bearing $\alpha_v\beta_3$ or $\alpha_v\beta_5$ integrins (Arap et al., (1998) Science 279:377–380). U.S. Pat. No. 5,627,263 describes peptides that are recognized by and selectively bind the $\alpha_v\beta_1$ integrin. Using structurally constrained peptide libraries generated by monovalent phage display, 14 amino acid peptides that specifically bind to insulin-like growth factor 1 binding proteins (IGFBPs) have been isolated (Lowman et al., (1998) Biochemistry, 37:8870–8878). The peptides contain a helix structure and bind IGFBPs in vitro liberating insulin like growth factor-$\alpha$ (IGF-1) activity (Lowman et al., (1998) supra).

Particular cellular receptors and their ligands, especially those implicated in the pathogenesis of various human malignancies, have recently been the focus of much attention in the scientific community as novel protein based therapeutics enter the clinic. For example, it has been found that the human erbB2 gene (also known as her2, or c-erbB-2), which encodes a 185-kd transmembrane glycoprotein receptor ($p185^{HER2}$) related to the epidermal growth factor receptor (EGFR), is overexpressed in about 25% to 30% of human breast cancer (Slamon et al., (1987) Science 235:177–182; Slamon et al., (1989) Science 244:707–712). Several lines of evidence support a direct role for ErbB2 in the pathogenesis and clinical aggressiveness of ErbB2-overexpressing tumors. The introduction of erbB2 into non-neoplastic cells has been shown to cause their malignant transformation (Hudziak et al., (1987) Proc. Natl. Acad. Sci. USA 84:7159–7163; DiFiore et al., (1987) Science 237:78–182). Transgenic mice that express HER2 were found to develop mammary tumors (Guy et al., (1992) Proc. Natl. Acad. Sci. USA 89:10578–10582).

ErbB2 overexpression is commonly regarded as a predictor of a poor prognosis, especially in patients with primary disease that involves axillary lymph nodes (Slamon et al., (1987) and (1989), supra; Ravdin and Chamness, (1995) Gene 159:19–27; and Hynes and Stern, (1994) Biochim. Biophys. Acta 1198:165–184). Overexpression has also been linked to sensitivity and/or resistance to hormone therapy and chemotherapeutic regimens, including CMF (cyclophosphamide, methotrexate, and fluoruracil) and anthracyclines (Baselga et al., (1997) Oncology 11(3 Suppl 1):43–48).

A recombinant humanized anti-ErbB2 monoclonal antibody (a humanized version of the murine anti-ErbB2 antibody 4D5, referred to as rhuMAb HER2 or HERCEPTIN®) is therapeutically active in patients with ErbB2-overexpressing metastatic breast cancers that have previously received extensive anti-cancer therapy (Baselga et al., (1996) J. Clin. Oncol. 14:737–744).

SUMMARY OF THE INVENTION

The present invention provides compounds which bind to the human erbB2 gene product (ErbB2). The compounds of the present invention (referred to as peptide ligands herein) are, for example, peptides or peptide derivatives such as peptide mimetics and peptide analogs. Preferred peptide ligands include linear and cyclic peptides, preferably cyclic peptide compounds comprising the following core formula:

-Cys-Xaa-Xaa-Xaa-Xaa-Cysand preferably those having the general formula:

Cys-Xaa-Xaa-Xaa-Xaa-Xaa-Xaa-Cys-Xaa-Xaa-Xaa-Xaa-Xaa-Xaa-
Cys-Cys-Xaa-Xaa-Xaa-Cys-Xaa-Xaa-Xaa-Xaa-Xaa-Xaa-Cys
(SEQ ID NO:70)

or the general formula:

Xaa-Xaa-Xaa-Xaa-Xaa-Xaa-Xaa-Cys-Xaa-Xaa-Xaa-Xaa-Cys-Xaa-Xaa-Xaa-Xaa-Xaa-Xaa-Xaa, including dimers and other combinations of the foregoing general structures. Preferred among the peptide ligands of the invention are peptides comprising the core formula:

-Cys-Cys/Ile-Gly-Pro-Gly-Cys-       (SEQ ID NO:71)

Specific examples of such compounds include cyclic peptides of between about 10 and 60 amino acid residues and optionally including N- or C-terminal modifications or both, such as esters, amides, salts and other derivatives thereof. According to preferred aspects of the invention, the compounds are preferably non-naturally occurring amino acid sequences that bind ErbB2. Preferably the compound is a non-naturally occurring amino acid sequence of between about 5 and about 50 amino acid residues. Preferred compounds are cyclic peptides having the foregoing general formulae and having of between about 20 and about 30 amino acid residues and include dimers and other combinations thereof.

In particular aspects the invention is directed to combinations of peptide ligands with other peptide ligands or with other proteins, especially serum proteins or peptides. The combinations are prepared with various objectives in mind, including; increasing the affinity or avidity of the peptide ligand for its target molecule, as for example, by use of various multimerization domains; increasing the stability of the peptide ligand or facilitating its recovery and purification, as for example by expressing the peptide ligand as a Z protein fusion; improving the therapeutic efficacy of the peptide ligand in aspects of the invention involving in vivo use of the peptide ligand, by for example, increasing or decreasing the serum half life, by for example, fusing the peptide ligand to a plasma protein such as serum albumin, an immunoglobulin, apolipoproteins or transferrin (such fusion being made conveniently in recombinant host cells or by the use of bifunctional crosslinking agents)and introducing additional functionalities, as for example, those of a functional Fc domain or cytotoxic or enzyme moiety.

According to a preferred aspect of the present invention the compound of the invention is linked to a multimerization domain. The multimerization domain is preferably an immunoglobulin sequence or, for example, a leucine zipper sequence. According to this aspect of the invention the immunoglobulin sequence is preferably an immunoglobulin constant region sequence and especially the constant region of an immunoglobulin heavy chain. According to preferred aspects of the invention, the multimerization domain pairs with one or more companion multimerization domains to provide home- and hetero-multimer compositions. Preferred according to this aspect of the present invention are homo- and hetero-multimers, especially homo- and heterodimers wherein the multimerization domains are immunoglobulin heavy chain constant regions which pair to provide functional immunoglobulin Fc domains. Therefore, according to preferred aspects, the invention provides a hybrid molecule comprising a compound of the invention which functions to target an ErbB2 bearing cell type and functional immunoglobulin Fc domain possessing an effector function associated with a functional immunoglobulin Fc domain.

Hybrid molecules according to this aspect of the invention optionally include a further functional moiety such as an enzyme moiety or a cytotoxic moiety. For example, the additional functional domain may be an enzyme covalently linked to a hybrid molecule and capable of acting on a prodrug in such a way as to convert the prodrug to its more active form. The optional functional domain, according to certain preferred aspects of the invention, may be a cytotoxic agent linked by, for example, covalent attachment, to a hybrid molecule. Preferred cytotoxic agents include, for example, chemotherapeutic agents, toxins and radioactive isotopes. The compounds including the hybrid molecules and compositions comprising them are used in binding or detecting the human erbB2 gene product and optionally delivering a functional moiety such as an enzyme or cytotoxic drug to an ErbB2 bearing cell type.

In one embodiment, the compound of the present invention, such as the hybrid molecule described above, is a polypeptide and the invention encompasses a composition of matter comprising an isolated nucleic acid, preferably DNA, encoding the polypeptide of the invention. According to this aspect, the invention further comprises an expression control sequence operably linked to the DNA molecule, an expression vector, preferably a plasmid, comprising the DNA molecule, where the control sequence is recognized by a host cell transformed with the vector, and a host cell transformed with the vector. According to preferred aspects the nucleic acid encodes a hybrid molecule comprising a peptide compound of the invention and an immunoglobulin constant region domain sequence. The nucleic acid molecule according to this aspect of the present invention encodes a hybrid molecule and the nucleic acid encoding the peptide compound of the invention is operably linked to (in the sense that the DNA sequences are contiguous and in reading frame) the immunoglobulin domain sequence. Optionally the DNA sequences may be linked through a nucleic acid sequence encoding an optional linker domain amino acid sequence.

The compositions of the present invention may be made by a process which includes the steps of isolating or synthesizing nucleic acid sequences encoding any of the amino acid sequences of the invention, ligating the nucleic acid sequence into a suitable expression vector capable of expressing the nucleic acid sequence in a suitable host, transforming the host with the expression vector into which the nucleic acid sequence has been ligated, and culturing the host under conditions suitable for expression of the nucleic acid sequence, whereby the protein encoded by the selected nucleic acid sequence is expressed by the host. Preferably, the polypeptide is then recovered from the host cell culture. In this process, the ligating step may further contemplate ligating the nucleic acid into a suitable expression vector such that the nucleic acid is operably linked to a suitable secretory signal, whereby the amino acid sequence is secreted by the host.

The invention includes compositions, including pharmaceutical compositions, comprising the compounds of the invention, especially for the detection and treatment of diseases or disorders associated with erbB2 gene expression. Provided are, for example, kits and articles of manufacture for the detection and treatment of cancer. Kits and articles of manufacture preferably include:

(a) a container;

(b) a label on or associated with said container; and (c) a composition comprising a compound of the present invention contained within said container wherein, according to certain embodiments, the composition is effective for treating a disease or disorder associated with erbB2, gene expression, such as cancer. Preferably, the label on said container indicates that the composition can be used for treating cancer, and the compound in said composition comprises a compound as described herein which binds to the human erbB2 gene product. The kits optionally include accessory components such as a second container comprising a pharmaceutically-acceptable buffer and instructions for using the composition to treat a disorder.

Also disclosed are methods useful in the treatment of various diseases and disorders, such as cancer, especially those characterized by the involvement of ErbB2. Therefore, the invention provides a method of treating an ErbB2 mediated or associated disease or disorder in a host in need thereof comprising administering to the host a therapeutically effective amount of a compound of the invention. The present invention further provides various dosage forms of the compounds of the present invention, including but not limited to, those suitable for parenteral, oral, rectal and pulmonary administration of a compound. In preferred aspects of the present invention, a therapeutic dosage form is provided suitable for intravenous delivery and the invention provides for the treatment of diseases or disorders involving a ErbB2 mediated or associated process or event such as cancer.

BRIEF DESCRIPTION OF THE DRAWINGS

FIG. 2A depicts alignments of native IgG Fc region amino acid sequences. Shown are human (hum) IgG Fc region sequences, humIgG1 (non-A and A allotypes) (SEQ ID NOs:72 and 73, respectively), humIgG2 (SEQ ID NO:74), humIgG3 (SEQ ID NO:75) and humIgG4 (SEQ ID NO:76), are shown. The human IgG1 sequence is the non-A allotype, and differences between this sequence and the A allotype (at positions 356 and 358; EU numbering system) are shown below the human IgG1 sequence. Also shown are native murine (mur) IgG Fc region sequences, murIgG1 (SEQ ID NO:77), murIgG2A (SEQ ID NO:78), murIgG2B (SEQ ID NO:79) and murIgG3 (SEQ ID NO:80), are also shown. FIG. 2B shows the percent identity among the Fc region sequences of FIG. 2A.

FIG. 3 shows the alignments of native human IgG Fc region sequences, humIgG1 (non-A and A allotypes) (SEQ ID NOs:72 and 73), humIgG2 (SEQ ID NO:74), humIgG3 (SEQ ID NO:75) and humIgG4 (SEQ ID NO:76) with differences between the sequences marked with asterisks.

FIG. 8A shows the 1.1.FI-Z (SEQ ID NO:81) preparation (S) purified using a Superdex 75 into monomer (M) and dimer (D) containing fractions. FIG. 8B shows an SDS PAGE analysis of starting material and fractions from the SUPERDEX™ 75 column for peptide 1.1.FI-Z. FIG. 8C shows HER2 binding activity coinciding with dimer fractions of 1.1.FI-Z when assayed using a competition assay.

FIGS. 9A–C. FIG. 9A shows the $(1.1FI)_2$-Z (SEQ ID NO:82) (1.1FI repeated twice and fused to the Z domain of protein A) preparation purified using a SUPERDEX™ 75 to monomer and dimer containing fractions. FIG. 9B shows and SDS PAGE analysis of fractions from the SUPERDEX™ column for peptide $(1.1FI)_2$-Z. FIG. 9C shows HER2 binding activity coinciding with monomer fractions of $(1.1FI)_2$-Z when assayed using a competition assay.

FIGS. 10A and 10B show that peptides HER201 and 7.1c-Z block the binding of Class 1 and Class 7 phage suggesting that both classes of peptides bind to the same site on HER2.

FIG. 11 shows examples of Class 1 and Class 7 sequences revealing a core homology region between the two classes of peptides. Sequence 7.1c (SEQ ID NO:83), 1.1.2 (SEQ ID NO:84), 1.1.FC (SEQ ID NO:85), 1.1.FA (SEQ ID NO:86), 1.1.FB (SEQ ID NO:87), 1.1.FH (SEQ ID NO:88), 1.1.CF (SEQ ID NO:89).

FIG. 15 shows the deduced peptide sequences from clones in libraries 1.1 and 7.1. Sequence 1.1 (SEQ ID NO:57); 1.1.8 (SEQ ID NO:58); 1.1.9 (SEQ ID NO:59); 1.1.10 (SEQ ID NO:60); 1.1.1 (SEQ ID NO:61); 1.1.2 (SEQ ID NO:62); 1.1.6 (SEQ ID NO:63); 1.1.11 (SEQ ID NO:64); 1.1.3 (SEQ ID NO:65); 1.1.4 (SEQ ID NO:66); 1.1.5 (SEQ ID NO:67); 1.1.7 (SEQ ID NO:68); Consensus (SEQ ID NO:69); 7.1 (SEQ ID NO:45); 7.1.1 (SEQ ID NO:46); 7.1.9 (SEQ ID NO:47); 7.1.6 (SEQ ID NO:48); 7.1.5 (SEQ ID NO:49); 7.1.3 (SEQ ID NO:50); 7.1.4 (SEQ ID NO:51); 7.1.2 (SEQ ID NO:52); 7.1.7 (SEQ ID NO:53); 7.1.8 (SEQ ID NO:54); 7.1.11 (SEQ ID NO:55); Consensus (SEQ ID NO:56).

FIG. 16 shows the sequences from random clones for each library by the fourth round of selection. Sequence 1.1 (SEQ ID NO:57); Consensus (SEQ ID NO:58); 1.1.FC (SEQ ID NO:30); 1.1.FN(SEQ ID NO:31); 1.1.FA (SEQ ID NO:1); 1.1.FM (SEQ ID NO:2); 1.1.FE (SEQ ID NO:3); 1.1.FH (SEQ ID NO:29); 1.1.FB (SEQ ID NO:12); 1.1.FF (SEQ ID NO:13); 1.1.FI (SEQ ID NO:14); 1.1.FK (SEQ ID NO:15); 1.1.FD (SEQ ID NO:16); 1.1.FQ (SEQ ID NO:17); 1.1.FS (SEQ ID NO:18); 1.1.FX (SEQ ID NO:9); 1.1.FY (SEQ ID NO:10); 1.1.FZ (SEQ ID NO:11); 1.1.NC (SEQ ID NO:4); 1.1.NB (SEQ ID NO:5); 1.1.NM (SEQ ID NO:6); 1.1.NQ (SEQ ID NO:7); 1.1.NA (SEQ ID NO:19); 1.1.NG (SEQ ID NO:20); 1.1.NH (SEQ ID NO:21); 1.1.NE (SEQ ID NO:22); 1.1.NJ (SEQ ID NO:23); 1.1.NF (SEQ ID NO:24); 1.1.NK (SEQ ID NO:25); 1.1.NR (SEQ ID NO:26); 1.1.CF (SEQ ID NO:28); 1.1.CA (SEQ ID NO:32); 1.1.CB (SEQ ID NO:33); 1.1.CC (SEQ ID NO:34); 1.1.CD (SEQ ID NO:35); 1.1.CE (SEQ ID NO:36); 1.1.CG (SEQ ID NO:37); 1.1.CH (SEQ ID NO:38); 1.1.CI (SEQ ID NO:39); 1.1.CJ (SEQ ID NO:40); 1.1.CL (SEQ ID NO:41); 1.1.CM (SEQ ID NO:42); 1.1.CP (SEQ ID NO:43).

DETAILED DESCRIPTION OF THE PREFERRED EMBODIMENTS

Definitions

Figure 1A:
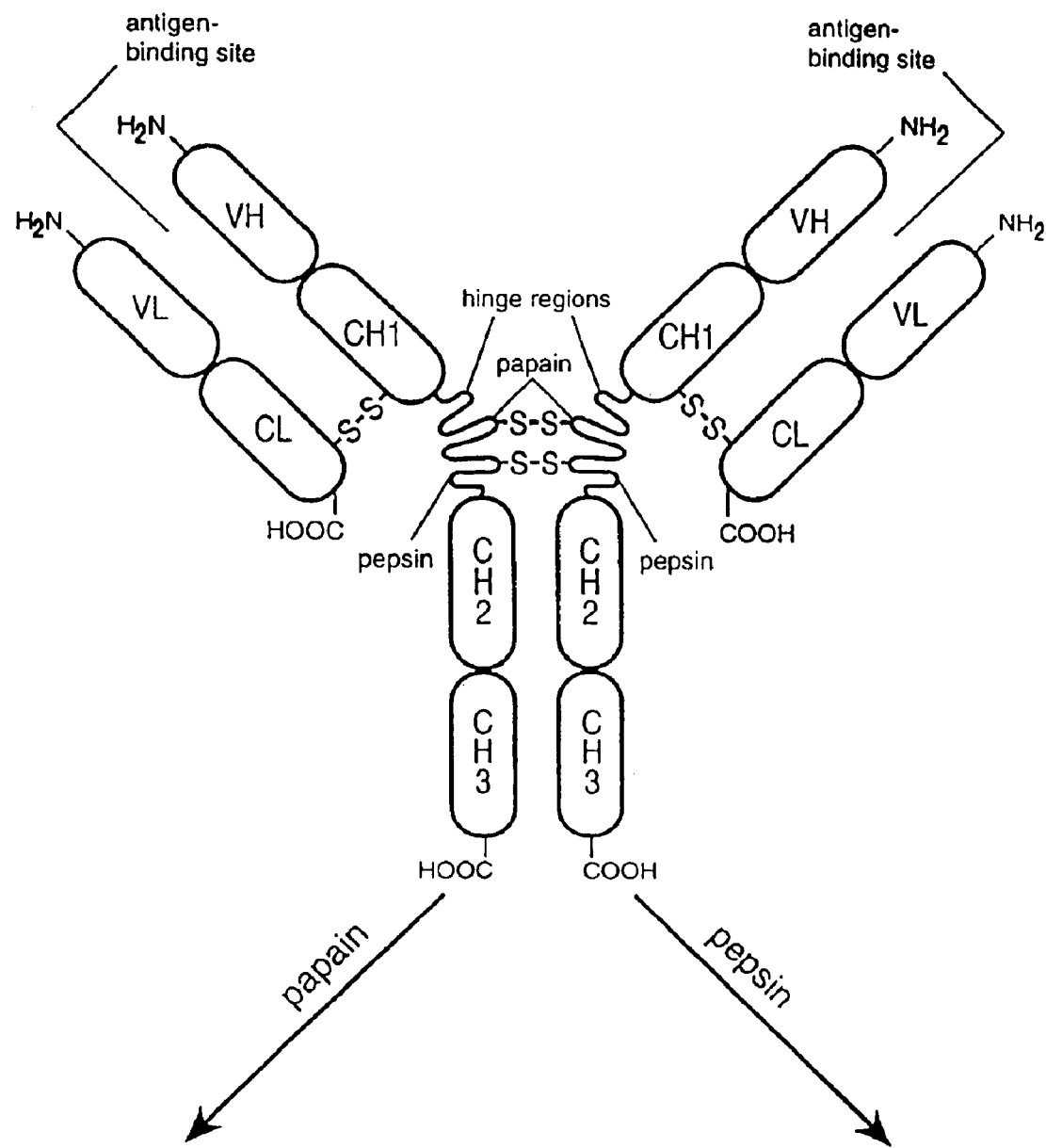
FIG. 1 is a schematic representation of a native IgG and fragments thereof resulting from papain and pepsin digest. Disulfide bonds are represented by —S—S— between, for example, the CH1 and CL domains. In the figure, V is variable domain; C is constant domain; L stands for light chain and H stands for heavy chain.

The terms "HER2", "ErbB2" "c-Erb-B2" are used interchangeably. Unless indicated otherwise, the terms "ErbB2" "c-Erb-B2" and "HER2" when used herein refer to the human protein and "her2", "erbB2" and "c-erb-B2" refer to the human gene. The human erbB2 gene and ErbB2 protein are described in, for example, Semba et al., (1985) PNAS (USA) 82:6497–6501 and Yamamoto et al. (1986) Nature 319:230–234 (Genebank accession number X03363). ErbB2 comprises four domains (Domains 1–4).

The term "peptide ligand" within the context of the present invention is meant to refer to amino acid sequences, regardless of their origin, that function to bind ErbB2. Peptide ligands within the context of the present invention are generally constrained (that is, having some element of structure as, for example, the presence of amino acids which initiate a β turn or β pleated sheet, or for example, cyclized by the presence of disulfide bonded Cys residues) or unconstrained (e.g., linear) amino acid sequences of less than about 50 amino acid residues, and preferably less than about 40 amino acid residues. Of the peptide ligands less than about 40 amino acid residues, preferred are the peptide ligands of between about 10 and about 30 amino acid residues and especially the peptide ligands of about 20 to about 30 amino acid residues. However, upon reading the instant disclosure, the skilled artisan will recognize that it is not the length of a particular peptide ligand but its ability to bind ErbB2 that distinguishes the peptide ligand of the present invention. Therefore, peptide ligands of 5, 6, 7, 8, 9, 10, 11, 12, 13, 14, 15, 16, 17, 18, 19, 20, 21, 22, 23, 24, 25, 26, 27, 28, 29 and 30 amino acid residues, for example, are equally likely to be peptide ligands within the context of the present invention.

A peptide ligand of the present invention will bind ErbB2 with sufficient affinity and specificity if the peptide ligand "homes" to, "binds" or "targets" ErbB2, such as an ErbB2 bearing cell, in vitro and preferably in vivo (see, for example, the use of the term "homes to," "homing," and "targets" in Pasqualini and Ruoslahti (1996) Nature, 380:364–366 and Arap et al., (1998) Science 279:377–380). In general, the peptide ligand will bind ErbB2 with an affinity of less than about 1 μM, preferably less about 100 nM and more preferably less than about 10 nM as determined by an in vitro assay such as a competition assay utilizing ErbB substrate analogous to those described by Jones et al., (1999) FEBS Letters 447:227–231. However, peptide ligands having an affinity for ErbB2 of less than about 1 nM and preferably between about 1 pM and 1 nM are equally likely to be peptide ligands within the context of the present invention. In general a peptide ligand that binds ErbB2 as described above can be isolated and identified by any of a number of art standard techniques as described herein as for example by binding an immobilized ErbB2 molecule.

As mentioned, peptides ligands are amino acid sequences as described above which may contain naturally as well as non-naturally occurring amino acid residues. Therefore, so-called "peptide mimetics" and "peptide analogs" which may include non-amino acid chemical structures that mimic the structure of a particular amino acid or peptide may be peptide ligands within the context of the invention. Such mimetics or analogs are characterized generally as exhibiting similar physical characteristics such as size, charge or hydrophobicity present in the appropriate spacial orientation as found in their peptide counterparts. A specific example of peptide mimetic compound is a compound in which the amide bond between one or more of the amino acids is replaced by, for example, a carbon-carbon bond or other bond as is well known in the art (see, for example Sawyer, in *Peptide Based Drug Design* pp. 378–422 (ACS, Washington D.C. 1995).

Therefore, the term "amino acid" within the scope of the present invention is used in its broadest sense and is meant to include naturally occurring L α-amino acids or residues. The commonly used one and three letter abbreviations for naturally occurring amino acids are used herein (Lehninger, A. L., Biochemistry, 2d ed., pp. 71–92, (1975), Worth Publishers, New York). The term includes D-amino acids as well as chemically modified amino acids such as amino acid analogs, naturally occurring amino acids that are not usually incorporated into proteins such as norleucine, and chemically synthesized compounds having properties known in the art to be characteristic of an amino acid. For example, analogs or mimetics of phenylalanine or proline, which allow the same conformational restriction of the peptide compounds as natural Phe or Pro are included within the definition of amino acid. Such analogs and mimetics are referred to herein as "functional equivalents" of an amino acid. Other examples of amino acids are listed by Roberts and Vellaccio (*The Peptides: Analysis, Synthesis, Biology,*) Eds. Gross and Meiehofer, Vol. 5 p 341, Academic Press, Inc, N.Y. 1983, which is incorporated herein by reference.

Peptide ligands synthesized by, for example, standard solid phase synthesis techniques, are not limited to amino acids encoded by genes. Commonly encountered amino acids which are not encoded by the genetic code, include, for example, those described in International Publication No. WO 90/01940 such as, for example, 2-amino adipic acid (Aad) for Glu and Asp; 2-aminopimelic acid (Apm) for Glu and Asp; 2-aminobutyric (Abu) acid for Met, Leu, and other aliphatic amino acids; 2-aminoheptanoic acid (Ahe) for Met, Leu and other aliphatic amino acids; 2-aminoisobutyric acid (Aib) for Gly; cyclohexylalanine (Cha) for Val, and Leu and Ile; homoarginine (Har) for Arg and Lys; 2,3-diaminopropionic acid (Dpr) for Lys, Arg and His; N-ethylglycine (EtGly) for Gly, Pro, and Ala; N-ethylglycine (EtGly) for Gly, Pro, and Ala; N-ethylasparigine (EtAsn) for Asn, and Gln; Hydroxyllysine (Hyl) for Lys; allohydroxyllysine (AHyl) for Lys; 3-(and 4)hydoxyproline (3Hyp, 4Hyp) for Pro, Ser, and Thr; alloisoleucine (AIle) for Ile, Leu, and Val; p-amidinophenylalanine for Ala; N-methylglycine (MeGly, sarcosine) for Gly, Pro, and Ala; N-methylisoleucine (MeIle) for Ile; Norvaline (Nva) for Met and other aliphatic amino acids; Norleucine (Nle) for Met and other aliphatic amino acids; Ornithine (Orn) for Lys, Arg and His; Citrulline (Cit) and methionine sulfoxide (MSO) for Thr, Asn and Gln; N-methylphenylalanine (MePhe), trimethylphenylalanine, halo (F, Cl, Br, and I) phenylalanine, triflourylphenylalanine, for Phe.

Conservative amino acid subsitutions within the context of the invention are shown in Table 1 under the heading of "exemplary substitutions" and "preferred substitutions". If preferred substitutions do not result in a decrease or change in HER2 binding, then more substantial changes, denominated "exemplary substitutions" in Table 1, or as further described herein, may be introduced and the products tested for HER2 binding.

TABLE 1

| Original Residue | Exemplary Substitutions | Preferred Substitutions |
| --- | --- | --- |
| Ala (A) | val; leu; ile | val |
| Arg (R) | lys; gln; asn | lys |
| Asn (N) | gln; his; asp, lys; arg | gln |
| Asp (D) | glu; asn | glu |
| Cys (C) | ser; ala | ser |
| Gln (Q) | asn; glu | asn |
| Glu (E) | asp; gln | asp |
| Gly (G) | ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | tyr |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Peptide ligands within the context of the present invention are preferably non-naturally occurring amino acid sequences. By non-naturally occurring is meant that the amino acid sequence of the particular peptide ligand is not found in nature. According to the present invention the term "non-naturally occurring" is used to refer to a peptide ligand that corresponds to a non-native or non-naturally occurring amino acid sequence. Peptide ligands of this variety may be produced or selected using a variety of techniques well known to the skilled artisan. For example, constrained or unconstrained peptide libraries may be randomly generated and displayed on phage utilizing art standard techniques (for example, Lowman et al., (1998) Biochemistry 37:8870–8878).

At least three distinct species of peptide ligands can be distinguished based upon function associated with binding ErbB2. They will be referred to herein as "neutral," "agonist" and "antagonist" peptide ligands. In general, a neutral peptide ligand functions to bind ErbB2 as described above. Neutral peptide ligands are preferred in aspects of the present invention where targeting of a particular cell type bearing ErbB2 with, for example, a cytotoxic agent or an enzyme is desired.

In general, an "agonist" peptide ligand in addition to binding ErbB2, has a direct effect on an ErbB2 bearing cell. Preferably the agonist peptide ligand will bind ErbB2 as described and, as well, initiate or mediate an event associated with the ErbB2-ErbB3 protein complex and/or the ErbB2-ErbB4 protein complex such as, for example, the ability to cause the intracellular kinase domain to phosphorylate tyrosine residues in the ErbB2 receptor complex. Additionally, binding of the agonist peptide ligand maybe associated with dimerization of the ErbB2 receptor. The ability to induce ErbB2 receptor mediated phosphorylation or ErbB2 receptor dimerization can be quantified using art standard techniques such as tyrosine phosphorylation assays and SDS PAGE.

By contrast, an "antagonist" peptide ligand acts to reduce the activity associated with a natural ligand binding the ErbB2-ErbB3 protein complex and/or ErbB2-ErbB4 protein complex, for example, the cellular response induced by the binding of the native ligand, by for example, binding to and blocking the association of ErbB2-ErbB3 protein complex and/or ErbB2-ErbB4 protein complex with a native or naturally occurring ligand.

However, the foregoing classes are not limiting. For example, in certain embodiments, binding of a peptide ligand causes internalization of the ErbB2 receptor, or the induction of associated cellular events such as the induction of programmed cell death or apoptosis. Peptide ligands that initiate internalization of ErbB2 or an ErbB2 receptor complex are especially useful in embodiments of the invention requiring intracellular delivery of a cytotoxic agent as described herein below.

The phrase "induces apoptosis" or "capable of inducing apoptosis" refers to the ability of a compound to induce programmed cell death as determined by binding of annexin V, fragmentation of DNA, cell shrinkage, dilation of endoplasmic reticulum, cell fragmentation, and/or formation of membrane vesicles (called apoptotic bodies). The cell is one which expresses or overexpresses the ErbB2 receptor. Preferably the "cell" is a tumor cell, e.g. a breast, ovarian, stomach, endometrial, salivary gland, lung, kidney, colon, thyroid, pancreatic or bladder cell. In vitro, the cell may be a SKBR3, BT474, Calu 3 cell, MDA-MB-453, MDA-MB-361 or SKOV3 cell. Various methods are available for evaluating the cellular events associated with apoptosis. For example, phosphatidyl serine (PS) translocation can be measured by annexin binding; DNA fragmentation can be evaluated through DNA laddering; and nuclear/chromatin condensation along with DNA fragmentation can be evaluated by any increase in hypodiploid cells. Preferably, the compound which induces apoptosis is one which results in about 2 to 50 fold, preferably about 5 to 50 fold, and most preferably about 10 to 50 fold, induction of annexin binding relative to untreated cell in an annexin binding assay using BT474 cells.

"Heregulin" (HRG) when used herein refers to a polypeptide which activates the ErbB2-ErbB3 and ErbB2-ErbB4 protein complexes (i.e. induces phosphorylation of tyrosine residues in the complex upon binding thereto). Various polypeptides encompassed by this term are disclosed in Jones et al., (1999) FEBS Letters 447:227–231; Holmes et al., (1992) Science, 256:1205–1210; WO 92/20798; Wen et al., (1994) Mol. Cell. Biol., 14(3):1909–1919; and Marchionni et al., (1993) Nature, 362:312–318, for example. The term includes biologically active fragments and/or variants of a naturally occurring HRG polypeptide, such as an EGF-like domain fragment thereof (e.g. $HRG\beta 1_{177-244}$).

The "ErbB2-ErbB3 protein complex" and "ErbB2-ErbB4 protein complex" are noncovalently associated oligomers of the ErbB2 receptor and the ErbB3 receptor or ErbB4 receptor, respectively. The complexes form on a cell expressing both of these receptors and can be isolated by immunoprecipitation and analyzed by SDS-PAGE as described in Sliwkowski et al., (1994) J. Biol. Chem., 269(20):14661–14665.

The term "multimerization domain" as used in particular aspects of the present invention, is meant to refer to the portion of the molecule to which the peptide ligand is joined, either directly or through a "linker domain." The multimerization domain is an amino acid domain which, according to preferred embodiments, facilitates the interaction of two or more multimerization domains. While the multimerization domain promotes the interaction between two or more multimerization domains, there is no requirement within the context of the present invention that the peptide ligand joined to a multimerization domain be present as a portion of a multimer.

According to preferred aspects of the present invention the multimerization domain is a polypeptide which promotes the stable interaction of two or more multimerization domains. By way of example and not limitation, a multimerization domain may be an immunoglobulin sequence, such as an immunoglobulin constant region, a leucine zipper, a hydrophobic region, a hydrophilic region, a polypeptide comprising a free thiol which forms an intermolecular disulfide bond between two or more multimerization domains or, for example a "protuberance-into-cavity" domain described in U.S. Pat. No. 5,731,168. In that patent, protuberances are constructed by replacing small amino acid side chains from the interface of a first polypeptide with a larger side chain (for example a tyrosine or tryptophan). Compensatory cavities of identical or similar size to the protuberances are optionally created on the interface of a second polypeptide by replacing large amino acid side chains with smaller ones (for example alanine or threonine).

Therefore, in a preferred aspect, the multimerization domain provides that portion of the molecule which promotes or allows stable interaction of two or more multimerization domains and promotes or allows the formation of dimers and other multimers from monomeric multimerization domains. Preferably, according to this aspect of the invention, multimerization domains are immunoglobulin constant region domains. Immunoglobulin constant domains provide the advantage of improving in vivo circulating half-life of the compounds of the invention and optionally allow the skilled artisan to incorporate an "effector function" as described herein below into certain aspects of the invention.

Throughout the present specification and claims, the numbering of the residues in an immunoglobulin heavy chain is that of the EU index as in Kabat et al., Sequences of Proteins of Immunological Interest, 5th Ed. Public Health Service, National Institutes of Health, Bethesda, Md. (1991), expressly incorporated herein by reference. The "EU index as in Kabat" refers to the residue numbering of the human IgG1 EU antibody.

"Antibodies" (Abs) and "immunoglobulins" (Igs) are glycoproteins having the same structural characteristics. While antibodies exhibit binding specificity to a specific antigen, immunoglobulins include both antibodies and other antibody-like molecules which lack antigen specificity. Polypeptides of the latter kind are, for example, produced at low levels by the lymph system and at increased levels by myelomas.

"Antibodies" and "immunoglobulins" are usually heterotetrameric glycoproteins of about 150,000 Daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has an amino (N) terminal variable domain (VH) followed by carboxy (C) terminal constant domains. Each light chain has a variable N-terminal domain (VL) and a C-terminal constant domain; the constant domain of the light chain (CL) is aligned with the first constant domain (CH1) of the heavy chain, and the light chain variable domain is aligned with the variable domain of the heavy chain. According to the domain definition of immunoglobulin polypeptide chains, light (L) chains have two conformationally similar domains VL and CL; and heavy chains have four domains (VH, CH1, CH2, and CH3) each of which has one intrachain disulfide bridge.

Depending on the amino acid sequence of the constant (C) domain of the heavy chains, immunoglobulins can be assigned to different classes. There are five major classes of immunoglobulins: IgA, IgD, IgE, IgG, and IgM. The immunoglobulin class can be further divided into subclasses (isotypes), e.g., $IgG_1$, $IgG_2$, $IgG_3$, $IgG_4$, $IgA_1$, and $IgA_2$. The heavy-chain constant domains that correspond to the different classes of immunoglobulins are $\alpha$, $\delta$, $\epsilon$, $\gamma$, and $\mu$ domains respectively. The light chains of antibodies from any vertebrate species can be assigned to one of two distinct types called kappa ($\kappa$) or lambda ($\lambda$), based upon the amino acid sequence of their constant domains. Sequence studies have shown that the $\mu$ chain of IgM contains five domains VH, $CH\mu1$, $CH\mu2$, $CH\mu3$, and $CH\mu4$. The heavy chain of IgE ($\epsilon$) also contains five domains.

The subunit structures and three-dimensional configurations of different classes of immunoglobulins are well known. Of these IgA and IgM are polymeric and each subunit contains two light and two heavy chains. The heavy chain of IgG ($\gamma$) contains a length of polypeptide chain lying between the $CH\gamma1$ and $CH\gamma2$ domains known as the hinge region. The $\alpha$ chain of IgA has a hinge region containing an O-linked glycosylation site and the $\mu$ and $\epsilon$ chains do not have a sequence analogous to the hinge region of the $\gamma$ and $\alpha$ chains, however, they contain a fourth constant domain lacking in the others. The domain composition of immunoglobulin chains can be summarized as follows:

Light Chain
$\lambda$=V$\lambda$ C$\lambda$
$\kappa$=V$\kappa$ C$\kappa$
Heavy Chain
IgG ($\gamma$)=VH CH$\gamma$1, hinge CH$\gamma$2 CH$\gamma$3
IgM ($\mu$)=VH CH$\mu$1 CH$\mu$2 CH$\mu$3 CH$\mu$4
IgA ($\alpha$)=VH CH$\alpha$1 hinge CH$\alpha$2 CH$\alpha$3
IgE ($\epsilon$)=VH CH$\epsilon$1 CH$\epsilon$2 CH$\epsilon$3 CH$\epsilon$4
IgD ($\delta$)=VH CH$\delta$1 hinge CH$\delta$2 CH$\delta$3

The "CH2 domain" of a human IgG Fc region (also referred to as "C$\gamma$2" domain) usually extends from about amino acid 231 to about amino acid 340. The CH2 domain is unique in that it is not closely paired with another domain. Rather, two N-linked branched carbohydrate chains are interposed between the two CH2 domains of an intact native IgG molecule.

The "CH3 domain" comprises the stretch of residues C-terminal to a CH2 domain in an Fc region (i.e. from about amino acid residue 341 to about amino acid residue 447 of an IgG).

"Hinge region" is generally defined as stretching from Glu216 to Pro230 of human IgG1 (Burton, Molec. Immunol.22:161–206 (1985)). Hinge regions of other IgG isotypes may be aligned with the IgG1 sequence by placing the first and last cysteine residues forming inter-heavy chain S—S bonds in the same positions.

The "lower hinge region" of an Fc region is normally defined as the stretch of residues immediately C-terminal to the hinge region, i.e. residues 233 to 239 of the Fc region.

Figure 1B:
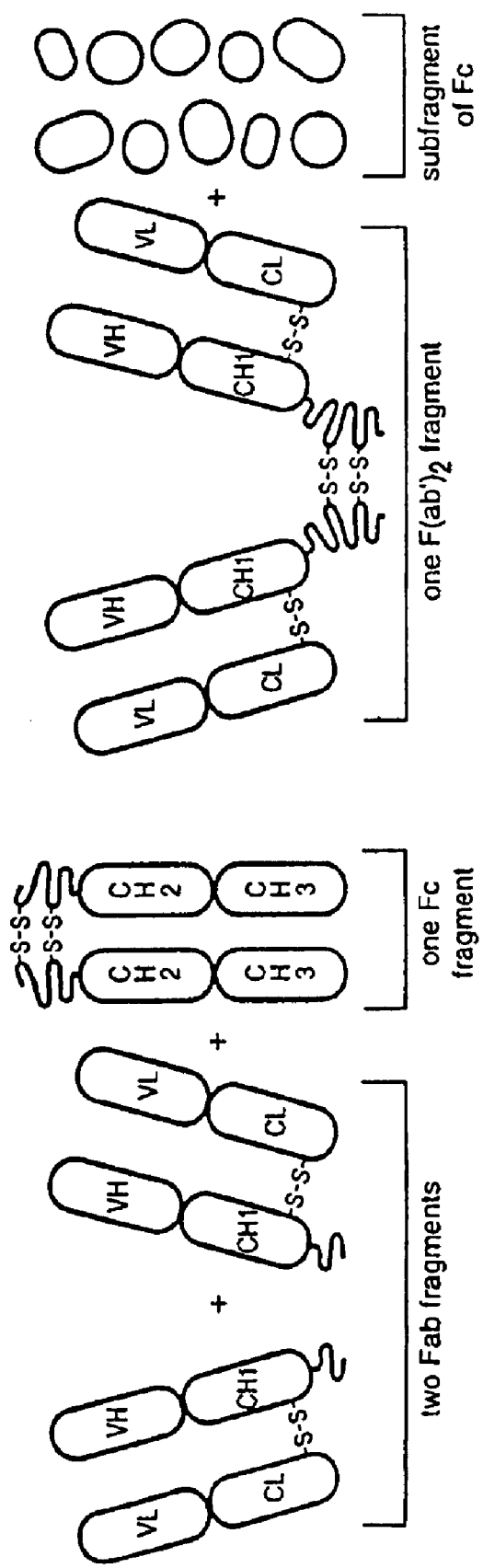

Papain digestion of antibodies produces two identical antigen-binding fragments, called "Fab" fragments or regions, each with a single antigen-binding site, and a residual "Fc" fragment or region (FIG. 1). Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The Fc region of an immunoglobulin generally comprises two constant domains, CH2 and CH3, as shown, for example, in FIG. 1. A "native Fc region sequence" comprises an amino acid sequence identical to the amino acid sequence of an Fc region found in nature. Native human Fc region sequences are shown in FIGS. 2 & 3 and include but are not limited to the human IgG1 Fc region (non-A and A allotypes); human IgG2 Fc region; human IgG3 Fc region; and human IgG4 Fc region as well as naturally occurring variants thereof. Native murine Fc regions sequences are shown in FIG. 2A.

Pepsin treatment yields an F(ab')$_2$ fragment that has two antigen-combining sites and is still capable of cross-linking antigen. The Fab fragment contains the constant domain of the light chain and the first constant domain (CH1) of the heavy chain. Fab' fragments differ from Fab fragments by the addition of a few residues at the carboxyl terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

A "functional Fc region" possesses an "effector function" of a native Fc region. Exemplary "effector functions" include C1q binding; complement dependent cytotoxicity; Fc receptor binding; antibody-dependent cell-mediated cytotoxicity (ADCC); phagocytosis; down regulation of cell surface receptors (e.g. B cell receptor; BCR), etc. Such effector functions generally require the Fc region to be combined with a binding domain (e.g. a peptide ligand) and can be assessed using various assays known in the art.

By introducing the appropriate amino acid sequence modifications in a parent or native Fc region, one can generate a variant Fc region which (a) mediates antibody-dependent cell-mediated cytotoxicity (ADCC) in the presence of human effector cells more effectively and/or (b) binds an Fc gamma receptor (FcγR) with better affinity than the parent polypeptide. Such Fc region variants will generally comprise at least one amino acid modification in the Fc region. The variant Fc region may include two, three, four, five, etc substitutions therein.

Several antibody effector functions are mediated by Fc receptors (FcRs), which bind the Fc region of an antibody. FcRs are defined by their specificity for immunoglobulin isotypes; Fc receptors for IgG antibodies are referred to as FcγR, for IgE as FcεR, for IgA as FcαR and so on. Three subclasses of FcγR have been identified: FcγR I (CD64), FcγR II (CD32) and FcγR III (CD16). Because each FcγR subclass is encoded by two or three genes, and alternative RNA spicing leads to multiple transcripts, a broad diversity in FcγR isoforms exists. These different FcR subtypes are expressed on different cell types (reviewed in Ravetch and Kinet, *Annu. Rev. Immunol.* 9:457–492 (1991)). For example, in humans, FcγRIIIB is found only on neutrophils, whereas FcγRIIIA is found on macrophages, monocytes, natural killer (NK) cells, and a subpopulation of T-cells. Notably, FcγRIIIA is the only FcR present on NK cells, one of the cell types implicated in ADCC.

The binding site on human and murine antibodies for FcγR have been previously mapped to the lower hinge region (residues 233–239: EU index numbering as in Kabat et al., *Sequences of Proteins of Immunological Interest,* 5th Ed. Public Health Service, National Institutes of Health, Bethesda, Md. (1991)). Woof et al. *Molec. Immunol.* 23:319–330 (1986); Duncan et al. *Nature* 332:563 (1988); Canfield and Morrison, *J. Exp. Med.* 173:1483–1491 (1991); Chappel et al., *Proc. Natl. Acad. Sci USA* 88:9036–9040 (1991).

"C1q" is a polypeptide that includes a binding site for the Fc region of an immunoglobulin. C1q together with two serine proteases, C1r and C1s, forms the complex C1, the first component of the complement dependent cytotoxicity (CDC) pathway.

"Antibody-dependent cell-mediated cytotoxicity" and "ADCC" refer to a cell-mediated reaction in which nonspecific cytotoxic cells that express FcRs (e.g. Natural Killer (NK) cells, neutrophils, and macrophages) recognize bound antibody on a target cell and subsequently cause lysis of the target cell. The primary cells for mediating ADCC, NK cells, express FcγRIII only, whereas monocytes express FcγRI, FcγRII and FcγRIII. FcR expression on hematopoietic cells in summarized is Table 3 on page 464 of Ravetch and Kinet, *Annu. Rev. Immunol* 9:457–92 (1991).

As used herein, the term "salvage receptor binding ligand" refers to an ligand of the Fc region of an IgG molecule (e.g., IgG$_1$, IgG$_2$, IgG$_3$, or IgG$_4$) that is responsible for increasing the in vivo serum half-life of the IgG molecule (U.S. Pat. No. 5,739,277, issued Apr. 14, 1998).

"Treatment" refers to both therapeutic treatment and prophylactic or preventative measures. Those in need of treatment include those already with the disorder as well as those in which the disorder is to be prevented.

"Mammal" for purposes of treatment refers to any animal classified as a mammal, including humans, domestic and farm animals, and zoo, sports, or pet animals, such as dogs, horses, cats, cows, etc. Preferably, the mammal is human.

A "disorder" is any condition that would benefit from treatment with the compositions comprising the peptide ligands of the invention. This includes chronic and acute disorders or diseases including those pathological conditions which predispose the mammal to the disorder in question. Non-limiting examples of disorders to be treated herein include benign and malignant tumors; leukemias and lymphoid malignancies; neuronal, glial, astrocytal, hypothalamic and other glandular, macrophagal, epithelial, stromal and blastocoelic disorders; and inflammatory, angiogenic and immunologic disorders.

The terms "cancer" and "cancerous" refer to or describe the physiological condition in mammals that is typically characterized by unregulated cell growth. Examples of cancer include, but are not limited to, carcinoma, lymphoma, blastoma, sarcoma, and leukemia. More particular examples of such cancers include squamous cell cancer, small-cell lung cancer, non-small cell lung cancer, gastrointestinal cancer, pancreatic cancer, glioblastoma, cervical cancer, ovarian cancer, liver cancer, bladder cancer, hepatoma, breast cancer, colon cancer, colorectal cancer, endometrial carcinoma, salivary gland carcinoma, kidney cancer, liver cancer, prostate cancer, vulval cancer, thyroid cancer, hepatic carcinoma and various types of head and neck cancer.

As used herein, the term "parenteral" refers to introduction of a compound of the invention into the body by other than the intestines, and in particular, intravenous (i.v.), intraarterial (i.a.), intraperitoneal (i.p.), intramuscular (i.m.), intraventricular, and subcutaneous (s.c.) routes.

Modes for Carrying Out the Invention

Peptide Ligands

Peptide ligands within the context of the present invention bind ErbB2 and can be identified by their ability to compete for binding ErbB2 in an in vitro assay with a peptide ligand having the general formula:

$$Xaa_{(1-14)}\text{-Cys-}Xaa_{16}\text{-Gly-Pro-Gly-Cys-}Xaa_{(21-27)} \quad \text{(SEQ ID NO:90)}$$

wherein $Xaa_{(1-14)}$ is absent or between one and fourteen amino acids; $Xaa_{16}$ is selected from the group consisting of Met, Thr, Cys and Ile and is preferably Ile; $Xaa_{(21-27)}$ is absent or between one and 7 amino acids. Preferably the peptide ligand will compete for binding ErbB2 as described with a peptide ligand having the following general formula:

$$Xaa_{(1-3)}\text{-Glu-}Xaa_5\text{-Trp-Gly-Cys-Ile-Gly-Pro-Gly-Cys-}Xaa_{14}\text{-}Xaa_{15}\text{-Leu-}Xaa_{(17-20)} \quad \text{(SEQ ID NO:91)}$$

wherein $X_{(1-3)}$ and $X_{(17-20)}$ are, independently, absent or between one and three and one and four amino acids respectively and $Xaa_1$, $Xaa_2$ and $Xaa_3$ are amino acids. In particular embodiments, the peptide ligand of the present invention will compete with any of the peptide ligands represented in SEQ ID NO: 1–SEQ ID NO: 44 and SEQ ID NO: 57–SEQ ID NO: 69 decribed herein and preferably will compete with SEQ ID NO: 14 for binding ErbB2.

As will be appreciated from the foregoing, the term "compete" and "ability to compete" are relative terms. Thus the terms, when used to describe the peptide ligands of the present invention, refer to peptide ligands that produce a 50% inhibition of binding of, for example, SEQ ID NO:14, when present at 50 µM, preferably when present at 1 µM, more preferably 100 µM, and preferably when present at 1 nM or less in a standard competition assay as described herein. Such peptide ligands will generally bind ErbB2 with an affinity of less than about 1 µM, preferably less about 100 nM and more preferably less than about 10 nM as determined by a standard competition assay such as the one described in the Example sections. However, peptide ligands having an affinity for ErbB2 of less than about 1 nM and preferably between about 1 pM and 1 nM are equally likely to be peptide ligands within the context of the present invention.

For in vitro assay systems to determine whether a compound has the ability to compete or competes with a peptide ligand described above, the skilled artisan can employ any of a number of standard competition assays. Such procedures include but are not limited to competitive assay systems using techniques such as radioimmunoassays, enzyme immunoassays (EIA), preferably the enzyme linked immunosorbent assay (ELISA), "sandwich" immunoassays, immunoradiometric assays, fluorescent immunoassays, and immunoelectrophoresis assays, to name but a few.

By way of exemplification and not limitation an ELISA assay can be conducted wherein microtiter plates (for example, Nunc Maxisorp™ 96-well plates, Inter Med, Denmark) are coated with HER2-ECD in 50 mM ammonium bicarbonate, pH 9.3, using 5 µg/ml, overnight at 4° C. Wells can be blocked using PBS containing 1% BSA (PBS-BSA) for 1 hr at 25° C. Candidate peptide ligands are titered in PBS-BSA and tested for their ability to block the binding of peptide 1.1.FI (SEQ ID NO: 14) produced as a Z protein fusion (1.1.FI-Z) as described herein and biotinylated (1.1.FI-Zb) to immobilized HER2-ECD. Following an incubation of about 1 hour the plate is washed with PBS-TWEEN and Strepavidin-HRP is added for about 30 min. Plates are washed again with PBS-TWEEN and the bound HRP assayed using ABTS/$H_2O_2$ substrate. The change in absorbance at 405 nm is monitored. Decrease in absorbance is plotted vs. sample concentration and an $IC_{50}$ for each candidate peptide ligand is determined.

As previously noted, preferred peptide ligands of the present invention are non-naturally occuring peptide ligands of between about 10 and 30 amino acid residues and preferably about 20 amino acid residues. Especially preferred peptide ligands as described above consist of naturally occurring amino acids and can be generated using standard recombinant and synthetic techniques well known to the skilled artisan.

Preferred peptide ligands have the general formula:
Xaa-Xaa-Xaa-Xaa-Xaa-Xaa-Xaa-Cys-Xaa-Xaa-Xaa-Xaa-Cys-Xaa-Xaa-Xaa-Xaa-Xaa-Xaa-Xaa. Somewhat more particularly, preferred peptide ligands have the formula:

$$Xaa_{(1-7)}\text{-Cys-}Xaa_9\text{-Gly-Pro-Gly-Cys-}Xaa_{(14-20)} \quad \text{(SEQ ID NO:92)}$$

wherein $X_{(1-7)}$ and $Xaa_{(14-20)}$ are, independently, absent or between one and seven amino acids and $Xaa_9$ is an amino acid selected from the group consisting of Met, Ile and Thr and is preferably Ile. Somewhat more particularity, preferred peptide ligands have the formula:

$$Xaa_{(1-5)}\text{-Trp-}Xaa_7\text{-Cys-}Xaa_9\text{-Gly-Pro-Gly-Cys-}Xaa_{(14-20)} \quad \text{(SEQ ID NO:93)}$$

wherein $Xaa_{(1-5)}$ is absent or between one and five amino acids and $Xaa_7$ is selected from the group consisting of Asp, Gly, Glu and His and preferably Gly. More preferred according to this aspect of the invention, are peptide ligands having the following formula are preferred:

$$Xaa_{(1-3)}\text{-Glu-}Xaa_5\text{-Trp-Gly-Cys-Ile-Gly-Pro-Gly-Cys-}Xaa_{14}\text{-}Xaa_{15}\text{-Leu-}Xaa_{(17-20)} \quad \text{(SEQ ID NO:91)}$$

wherein $Xaa_{(1-3)}$- is absent or between one and three amino acids, $Xaa_5$ is an amino acid, $Xaa_{13}$ is an amino acid, $Xaa_{14}$ is an amino acid and -$Xaa_{(17-20)}$ is absent or between one and four amino acids. Exemplary peptide ligands according to this aspect of the invention are peptide ligands wherein $X_{(1,3)}$- is absent or selected from the group consisting of: Gln-Arg-Asn-, Leu-Ser-Pro-, Glu-Asn-Trp-, Ala-Ser-His-, Lys-Leu-Asn-, Thr-Gln-Ala-, Ala-Pro-Arg-, Gln-Val-Tyr-, Arg-Thr-Glu-, Phe-Ala-Gly-, Thr-Ala-Arg-, Arg-Pro-His-, Asn-Val-Cys-, Cys-Ile-Asp-, Tyr-Glu-Trp-, Arg-Trp-Asp-, His-Trp-Met-, Asn-Trp-Pro-, Phe-Asn-Trp-, Phe-Ser-Gly-, Gly-Gly-Trp-, Leu-Trp-Phe-, Gly-Ile-Pro-, Trp-Trp-Thr-, Leu-Gly-Trp-, Ser-Pro-Trp-, Arg-Gly-Trp-, Tyr-Glu-Phe-, Tyr-Glu-Gly-, Tyr-Glu-Val-, Tyr-Ser-Phe-, Tyr-Asp-Phe-, Asp-Glu-Val-, Ser-Glu-Val-, Phe-Glu-Phe-, and His-Asp-Val-; $Xaa_5$ is selected from the group consisting of Ala, Thr, Met, Val, Arg, Glu, Asp, Ser, Gln, Pro, Gly, Phe and Lys; $Xaa_{14}$ is selected from the group consisting of Glu, Lys, Arg, Asp, Ser, Ala, Asn, Thr, Gly, Pro, Val and Gln, $Xaa_{15}$ is selected from the group consisting of Met, Phe, Ala, Cys, Gln, Glu, Trp, Leu, Val, Tyr, Thr, Ser and Asn, and -$Xaa_{(17-20)}$ is a four amino acid peptide having the following exemplary sequences:
-Phe-Gly-Ala-His (SEQ ID NO:94)
-Phe-Asp-Ala-His (SEQ ID NO:95)
-Leu-Glu-Ala-His (SEQ ID NO:96)
-Phe-Glu-Gly-His (SEQ ID NO:97)
-Phe-Gly-Ala-Leu (SEQ ID NO:98)
-Phe-Glu-Ala-Tyr (SEQ ID NO:99)
-Phe-Ala-Gly-His (SEQ ID NO:100) and
-Phe-Glu-Ala-Phe (SEQ ID NO:101).
Preferably -$Xaa_{(17-20)}$ is a four amino acid peptide having the following formula:

$$\text{-}Xaa_{17}\text{-}Xaa_{18}\text{-Cys-}Xaa_{20}.$$

Exemplary peptide ligands according to this aspect of the invention are peptide ligands wherein -Xaa$_{(17-20)}$ is selected from the group consisting of:
-Gln-Ala-Cys-Met (SEQ ID NO:102)
-Leu-Gln-Cys-Trp (SEQ ID NO:103)
-Met-Ser-Cys-Val (SEQ ID NO:104)
-Leu-Arg-Cys-Ile (SEQ ID NO:105)
-Gln-Ala-Cys-Leu (SEQ ID NO:106)
-Leu-Ser-Cys-Leu (SEQ ID NO:107)
-Ile-Gly-Cys-Leu (SEQ ID NO:108)
-Leu-Ala-Cys-Leu (SEQ ID NO:109)
-Leu-Ser-Cys-Ile (SEQ ID NO:110)
-Met-Asn-Cys-Leu (SEQ ID NO:111)
-Leu-Arg-Cys-Leu (SEQ ID NO:112)
-Leu-Lys-Cys-Leu (SEQ ID NO:113)
-Leu-Gly-Cys-Leu (SEQ ID NO:114)
-Leu-Asn-Cys-Ile (SEQ ID NO:115)
-Met-Gly-Cys-Leu (SEQ ID NO:116) and
-Met-Ala-Cys-Leu (SEQ ID NO:117).

According to another embodiment of this aspect of the invention are peptide ligands wherein -Xaa$_{(17-20)}$ is a four amino acid peptide having the following formula:

-Cys-Xaa$_{18}$-Xaa$_{19}$-Cys wherein Xaa$_{18}$ is an amino acid and Xaa$_{19}$ is an amino acid. According to this aspect of the invention, exemplary peptide ligands comprise an -Xaa$_{(17-20)}$ selected from the group consisting of:
-Cys-Ala-Trp-Cys (SEQ ID NO:118)
-Cys-Ser-Trp-Cys (SEQ ID NO:119)
-Cys-Glu-Pro-Cys (SEQ ID NO:120)
-Cys-Asp-Trp-Cys (SEQ ID NO:121)
-Cys-Glu-Trp-Cys (SEQ ID NO:122)
-Cys-Asn-Trp-Cys (SEQ ID NO:123) and
-Cys-Gly-Trp-Cys (SEQ ID NO:124).

Exemplary peptide ligands according to this aspect of the invention include:
Gln-Arg-Asn-Glu-Ala-Trp-Gly-Cys-Ile-Gly-Pro-Gly-Cys-Glu-Met-Leu-Cys-Ala-Trp-Cys (SEQ ID NO:1)
Leu-Ser-Pro-Glu-Thr-Trp-Gly-Cys-Ile-Gly-Pro-Gly-Cys-Glu-Met-Leu-Cys-Ser-Trp-Cys (SEQ ID NO:2)
Glu-Asn-Trp-Glu-Met-Trp-Gly-Cys-Ile-Gly-Pro-Gly-Cys-Lys-Phe-Leu Cys-Glu-Pro-Cys (SEQ ID NO:3)
Glu-Val-Trp-Gly-Cys-Ile-Gly-Pro-Gly-Cys-Lys-Ala-Leu-Cys-Asp-Trp-Cys (SEQ ID NO:4)
Glu-Arg-Trp-Gly-Cys-Ile-Gly-Pro-Gly-Cys-Arg-Met-Leu-Cys-Glu-Trp-Cys (SEQ ID NO:5)
Glu-Val-Trp-Gly-Cys-Ile-Gly-Pro-Gly-Cys-Asp-Met-Leu-Cys-Asn-Trp-Cys (SEQ ID NO:6)
Glu-Val-Trp-Gly-Cys-Ile-Gly-Pro-Gly-Cys-Ser-Met-Leu-Cys-Gly-Trp-Cys (SEQ ID NO:7)
Xaa-Xaa-Xaa-Glu-Xaa-Trp-Gly-Cys-Ile-Gly-Pro-Gly-Cys-Xaa-Met-Leu-Cys-Xaa-Trp-Cys (SEQ ID NO:8)
Ala-Ser-His-Glu-Val-Trp-Gly-Cys-Ile-Gly-Pro-Gly-Cys-Lys-Cys-Leu-Gln-Ala-Cys-Met (SEQ ID NO:9)
Lys-Leu-Asn-Glu-Glu-Trp-Gly-Cys-Ile-Gly-Pro-Gly-Cys-Ala-Cys-Leu Leu-Gln-Cys-Trp (SEQ ID NO:10)
Lys-Leu-Asn-Glu-Asp-Trp-Gly-Cys-Ile-Gly-Pro-Gly-Cys-Ala-Cys-Leu-Leu-Xaa-Cys-Xaa (SEQ ID NO:11)
Thr-Gln-Ala-Glu-Arg-Trp-Gly-Cys-Ile-Gly-Pro-Gly-Cys-Glu-Cys-Leu-Met-Ser-Cys-Val (SEQ ID NO:12)
Ala-Pro-Arg-Glu-Val-Trp-Gly-Cys-Ile-Gly-Pro-Gly-Cys-Ala-Cys-Leu-Leu-Arg-Cys-Ile (SEQ ID NO:13)
Gln-Val-Tyr-Glu-Ser-Trp-Gly-Cys-Ile-Gly-Pro-Gly-Cys-Ala-Cys-Leu-Gln-Ala-Cys-Leu (SEQ ID NO:14)
Arg-Thr-Glu-Glu-Gln-Trp-Gly-Cys-Ile-Gly-Pro-Gly-Cys-Arg-Cys-Leu Leu-Ser-Cys-Leu (SEQ ID NO:15)
Phe-Ala-Gly-Glu-Ser-Trp-Gly-Cys-Ile-Gly-Pro-Gly-Cys-Glu-Cys-Leu-Ile-Gly-Cys-Leu (SEQ ID NO:16)
Thr-Ala-Arg-Glu-Val-Trp-Gly-Cys-Ile-Gly-Pro-Gly-Cys-Asn-Cys-Leu-Leu-Ala-Cys-Leu (SEQ ID NO:17)
Arg-Pro-His-Glu-Pro-Trp-Gly-Cys-Ile-Gly-Pro-Gly-Cys-Ser-Cys-Leu-Leu-Ser-Cys-Ile (SEQ ID NO:18)
Glu-Val-Trp-Gly-Cys-Ile-Gly-Pro-Gly-Cys-Glu-Cys-Leu-Met-Asn-Cys-Leu (SEQ ID NO:19)
Glu-Gly-Trp-Gly-Cys-Ile-Gly-Pro-Gly-Cys-Glu-Cys-Leu-Leu-Arg-Cys-Leu (SEQ ID NO:20)
Glu-Gly-Trp-Gly-Cys-Ile-Gly-Pro-Gly-Cys-Gly-Cys-Leu-Leu-Lys-Cys-Leu (SEQ ID NO:21)
Glu-Pro-Trp-Gly-Cys-Ile-Gly-Pro-Gly-Cys-Ala-Cys-Leu-Leu-Gly-Cys-Leu (SEQ ID NO:22)
Glu-Glu-Trp-Gly-Cys-Ile-Gly-Pro-Gly-Cys-Ala-Cys-Leu-Leu-Asn-Cys-Ile (SEQ ID NO:23)
Glu-Gln-Trp-Gly-Cys-Ile-Gly-Pro-Gly-Cys-Lys-Cys-Leu-Met-Gly-Cys-Leu (SEQ ID NO:24)
Glu-Gln-Trp-Gly-Cys-Ile-Gly-Pro-Gly-Cys-Gly-Cys-Leu-Leu-Arg-Cys-Leu (SEQ ID NO:25)
Glu-Ala-Trp-Gly-Cys-Ile-Gly-Pro-Gly-Cys-Gly-Cys-Leu-Met-Ala-Cys-Leu (SEQ ID NO:26)
Xaa-Xaa-Xaa-Glu-Xaa-Trp-Gly-Cys-Ile-Gly-Pro-Gly-Cys-Xaa-Cys-Leu-Leu-Xaa-Cys-Leu (SEQ ID NO:27)
Asn-Val-Cys-Glu-Phe-Trp-Gly-Cys-Ile-Gly-Pro-Gly-Cys-Ala-Gln-Leu-Cys (SEQ ID NO:28)
Cys-Ile-Asp-Glu-Thr-Trp-Gly-Cys-Ile-Gly-Pro-Gly-Cys-Glu-Glu-Leu Arg-Cys-Lys-Arg (SEQ ID NO:29)
Tyr-Glu-Trp-Glu-Gly-Trp-Gly-Cys-Ile-Gly-Pro-Gly-Cys-Pro-Ala-Leu-Gly-Phe-Gly-Tyr (SEQ ID NO:30)
Arg-Trp-Asp-Glu-Glu-Trp-Gly-Cys-Ile-Gly-Pro-Gly-Cys-Glu-Trp-Leu-Val-Val-Arg-Lys (SEQ ID NO:31)
His-Trp-Met-Glu-Arg-Trp-Gly-Cys-Ile-Gly-Pro-Gly-Cys-Gly-Phe-Leu (SEQ ID NO:32)
Asn-Trp-Pro-Glu-Gly-Trp-Gly-Cys-Ile-Gly-Pro-Gly-Cys-Lys-Leu-Leu (SEQ ID NO:33)
Phe-Asn-Trp-Glu-Lys-Trp-Gly-Cys-Ile-Gly-Pro-Gly-Cys-Arg-Thr-Leu (SEQ ID NO:34)
Phe-Ser-Gly-Glu-Arg-Trp-Gly-Cys-Ile-Gly-Pro-Gly-Cys-Gln-Val-Leu (SEQ ID NO:35)
Gly-Gly-Trp-Glu-Gly-Trp-Gly-Cys-Ile-Gly-Pro-Gly-Cys-Arg-Tyr-Leu (SEQ ID NO:36)
Leu-Trp-Phe-Glu-Arg-Trp-Gly-Cys-Ile-Gly-Pro-Gly-Cys-Thr-Xaa-Leu (SEQ ID NO:37)
Gly-Ile-Pro-Glu-Gly-Trp-Gly-Cys-Ile-Gly-Pro-Gly-Cys-Glu-Trp-Leu (SEQ ID NO:38)
Trp-Trp-Thr-Glu-Arg-Trp-Gly-Cys-Ile-Gly-Pro-Gly-Cys-Ser-Met-Leu (SEQ ID NO:39)
Xaa-Cys-Xaa-Glu-Arg-Trp-Gly-Cys-Ile-Gly-Pro-Gly-Cys-Ser-Met-Leu (SEQ ID NO:40)
Leu-Gly-Trp-Glu-Arg-Trp-Gly-Cys-Ile-Gly-Pro-Gly-Cys-Arg-Ala-Leu (SEQ ID NO:41)
Ser-Pro-Trp-Glu-Gly-Trp-Gly-Cys-Ile-Gly-Pro-Gly-Cys-Arg-Trp-Leu (SEQ ID NO:42)
Arg-Gly-Trp-Glu-Gly-Trp-Gly-Cys-Ile-Gly-Pro-Gly-Cys-Ser-Phe-Leu (SEQ ID NO:43)
Xaa-Xaa-Trp-Glu-Xaa-Trp-Gly-Cys-Ile-Gly-Pro-Gly-Cys-Xaa-Xaa-Leu-Xaa-Xaa-Xaa-Xaa (SEQ ID NO:44)
Tyr-Glu-Val-Glu-Ala-Trp-Asp-Cys-Met-Gly-Pro-Gly-Cys-Ala-Asn-Leu-Phe-Glu-Ala-His (SEQ ID NO:57)
Tyr-Glu-Phe-Glu-Gly-Trp-Asp-Cys-Met-Gly-Pro-Gly-Cys-Ala-Ser-Val-Phe-Gly-Ala-His (SEQ ID NO:58)
Tyr-Glu-Gly-Glu-Ser-Trp-Gly-Cys-Ile-Gly-Pro-Gly-Cys-Ala-Ser-Leu-Phe-Asp-Ala-His (SEQ ID NO:59)
Tyr-Glu-Val-Glu-Val-Trp-Gly-Cys-Ile-Gly-Pro-Gly-Cys-Gly-Tyr-Leu-Phe-Gly-Ala-His (SEQ ID NO:60)
Tyr-Glu-Val-Glu-Gly-Trp-Gly-Cys-Met-Gly-Pro-Gly-Cys-Ala-Phe-Leu-Leu-Glu-Ala-His (SEQ ID NO:61)

Tyr-Ser-Phe-Glu-Gly-Trp-Gly-Cys-Ile-Gly-Pro-Gly-Cys-Ala-Tyr-Leu-Phe-Glu-Gly-His (SEQ ID NO:62)
Tyr-Asp-Phe-Glu-Gly-Trp-Gly-Cys-Ile-Gly-Pro-Gly-Cys-Gly-Asn-Leu-Leu-Glu-Ala-His (SEQ ID NO:63)
Tyr-Asp-Phe-Glu-Gly-Trp-Asp-Cys-Thr-Gly-Pro-Gly-Cys-Ala-Tyr-Leu-Phe-Glu-Gly-His (SEQ ID NO:64)
Asp-Glu-Val-Glu-Ser-Trp-Gly-Cys-Ile-Gly-Pro-Gly-Cys-Ala-Tyr-Leu-Phe-Gly-Ala-Leu (SEQ ID NO:65)
Ser-Glu-Val-Glu-Val-Trp-His-Cys-Ile-Gly-Pro-Gly-Cys-Val-Tyr-Leu-Phe-Glu-Ala-Tyr (SEQ ID NO:66)
Phe-Glu-Phe-Glu-Gly-Trp-Glu-Cys-Met-Gly-Pro-Gly-Cys-Ala-Glu-Leu-Phe-Ala-Gly-His (SEQ ID NO:67)
His-Asp-Val-Glu-Gly-Trp-Gly-Cys-Ile-Gly-Pro-Gly-Cys-Ala-Asp-Leu-Phe-Glu-Ala-Phe (SEQ ID NO:68)
Tyr-Glu-Phe-Glu-Gly-Trp-Gly-Cys-Ile-Gly-Pro-Gly-Cys-Ala-Tyr-Leu-Phe-Glu-Ala-His (SEQ ID NO:69)
including conservative amino acid substitutions within the foregoing exemplary amino acid sequences.

Further preferred peptide compounds also have the general formula:

Cys-Xaa-Xaa-Xaa-Xaa-Xaa-Xaa-Cys-Xaa-Xaa-Xaa-Xaa-Xaa-Xaa-Cys-Cys-Xaa-Xaa-Xaa-Cys-Xaa-Xaa-Xaa-Xaa-Xaa-Cys (SEQ ID NO:125).

Somewhat more particularly the formula:

$Xaa_{(1-10)}$-Glu-$Xaa_{12}$-Trp-$Xaa_{14}$-Cys-Cys-Gly-Pro-Gly-Cys-$Xaa_{21}$-$Xaa_{22}$-$Xaa_{23}$-$Xaa_{(24-27)}$ (SEQ ID NO:126)

wherein $Xaa_{(1-10)}$ is absent or between 1 and 10 amino acids, $Xaa_{12}$ is an amino acid, $Xaa_{14}$ is an amino acid, $Xaa_{21}$ is an amino acid, $Xaa_{22}$ is an amino acid, $Xaa_{23}$ is an amino acid selected from the group consisting of Val and Leu and $Xaa_{(24-27)}$ is absent or between one and four amino acids. Preferably, according to this aspect of the invention, $Xaa_{12}$ is an amino acid selected from the group consisting of Val, Leu, Ser, Trp; $Xaa_{14}$ is an amino acid selected from the group consisting of Gln, Glu, Asp and His; $Xaa_{21}$ is an amino acid selected from the group consisting of Gly and Glu; $Xaa_{22}$ is an amino acid selected from the group consisting of Trp, Leu and Phe and $Xaa_{23}$ is Val.

Preferred peptide ligands according to this aspect of the invention include those wherein $Xaa_{(1-10)}$ is 10 amino acids having the following formula:
Cys-$Xaa_{(2-7)}$-Cys-$Xaa_9$-Gly- and wherein $Xaa_{(24-27)}$ is four amino acids having the following formula:
$Xaa_{(24-26)}$-Cys and wherein $Xaa_{(2-7)}$ is six amino acids and $Xaa_{(24-26)}$ is 3 amino acids.

Preferred according to this aspect of the invention are peptide ligands wherein $Xaa_{(1-10)}$ has the following formula:

Cys-$Xaa_2$-Trp-Val-$Xaa_5$-$Xaa_6$-$Xaa_7$-Cys-$Xaa_9$-Gly (SEQ ID NO:127)

wherein
$Xaa_2$ is an amino acid selected from the group consisting of Ala and Ser, $Xaa_5$ is an amino acid selected from the group consisting of Ser, Leu, Ala, Arg and Val, $Xaa_6$ is an amino acid selected from the group consisting of Phe, Val and Leu, $Xaa_7$ is an amino acid selected from the group consisting of Asp, Gln, Tyr, Trp, Leu and His and $Xaa_9$ is an amino acid selected from the group consisting of Gly, Phe and Leu.

Preferred among this group of peptides are peptide ligands wherein $Xaa_{(1-10)}$ has the following formula:

Cys-Ala-Trp-Val-Leu-$Xaa_6$-$Xaa_7$-Cys-Gly-Gly- (SEQ ID NO:128) and wherein $Xaa_{(24-26)}$ has the following formula:

$Xaa_{24}$-$Xaa_{25}$-$Xaa_{26}$ and $Xaa_{24}$ is an amino acid selected from the group consisting of Trp, Val, Gly and Ala, preferably Val; $Xaa_{25}$ is an amino acid selected from the group consisting of Asn, Lys, Asp, Glu and His, preferably Asn and $Xaa_{26}$ is an amino acid selected from the group consisting of Ala, Ser and Val and preferably Ala.

By way of exemplification and not limitation the following are suitable peptide ligands within the context of the present invention:
Cys-Ser-Trp-Val-Leu-Val-Gln-Cys-Gly-Gly-Glu-Trp-Trp-His-Cys-Cys-Gly-Leu-Gly-Cys-Gly-Leu-Val-Val-Asn-Ala-Cys (SEQ ID NO: 45)
Cys-Ala-Trp-Val-Ser-Phe-Glu-Cys-Gly-Gly-Glu-Val-Trp-His-Cys-Cys-Gly-Leu-Gly-Cys-Gly-Trp-Val-Trp-Lys-Ala-Cys (SEQ ID NO: 46)
Cys-Ala-Trp-Val-Leu-Val-Gln-Cys-Gly-Gly-Glu-Trp-Trp-His-Cys-Cys-Gly-Pro-Gly-Cys-Glu-Phe-Val-Val-Asp-Ala-Cys (SEQ ID NO: 47)
Cys-Ala-Trp-Val-Ala-Val-Tyr-Cys-Gly-Gly-Glu-Leu-Trp-His-Cys-Cys-Gly-Pro-Gly-Cys-Gly-Phe-Val-Val-Asp-Ser-Cys (SEQ ID NO: 48)
Cys-Ala-Trp-Val-Arg-Val-Trp-Cys-Phe-Gly-Glu-Trp-Trp-Asp-Cys-Cys-Gly-Leu-Gly-Cys-Gly-Trp-Val-Val-Asn-Val-Cys (SEQ ID NO: 49)
Cys-Ala-Trp-Val-Arg-Val-Leu-Cys-Gly-Gly-Glu-Trp-Trp-His-Cys-Cys-Gly-Leu-Gly-Cys-Gly-Trp-Val-val-Glu-Ala-Cys (SEQ ID NO: 50)
Cys-Ser-Trp-Val-Ser-Val-Leu-Cys-Gly-Gly-Glu-Trp-Trp-Gln-Cys-Cys-Gly-Pro-Gly-Cys-Gly-Leu-Val-Val-Asn-Ala-Cys (SEQ ID NO: 51)
Cys-Ser-Trp-Val-Ser-Leu-Gln-Cys-Gly-Gly-Glu-Trp-Trp-His-Cys-Cys-Gly-Gly-Gly-Cys-Gly-Trp-Val-Val-Asn-Val-Cys (SEQ ID NO: 52)
Cys-Ser-Trp-Val-Leu-Leu-His-Cys-Gly-Gly-Glu-Trp-Trp-His-Cys-Cys-Gly-Gly-Gly-Cys-Gly-Trp-Val-Gly-Glu-Ala-Cys (SEQ ID NO: 53)
Cys-Ser-Trp-Val-Leu-Leu-Glu-Cys-Gly-Gly-Glu-Leu-Trp-Glu-Cys-Cys Gly-Leu-Gly-Cys-Gly-Trp-Val-Ala-Asp-Ala-Cys (SEQ ID NO: 54)
Cys-Ser-Trp-Val-Val-Phe-Glu-Cys-Leu-Gly-Glu-Ser-Trp-His-Cys-Cys-Gly-Gly-Gly-Cys-Gly-Trp-Val-Val-His-Ala-Cys (SEQ ID NO: 55)
Cys-Ala-Trp-Val-Ser-Val-Glu-Cys-Gly-Gly-Glu-Trp-Trp-His-Cys-Cys-Gly-Pro-Gly-Cys-Gly-Trp-Val-Val-Asp-Ala-Cys (SEQ ID NO: 56)

Peptide Ligand Combinations

A. Multimerization Domains

According to a preferred embodiment of the invention, the peptide ligands are combined with a multimerization domain. According to this aspect of the invention, hybrid molecules are provided which comprise at least two distinct domains. Each molecule comprises a peptide ligand domain and a multimerization domain. According to the present invention, the peptide ligand domain is joined to a multimerization domain such as an immunoglobulin Fc region, optionally via a flexible linker domain.

The hybrid molecules of the present invention are constructed by combining the peptide ligands with a suitable multimerization domain. Ordinarily, when preparing the hybrid molecules of the present invention, nucleic acid encoding the peptide ligand will be operably linked to nucleic acid encoding the multimerization domain sequence. Typically the construct encodes a fusion protein wherein the C-terminus of the peptide ligand is joined to the N-terminus or C-terminus, preferably the C-terminus of the multimerization domain. However, fusions where, for example, the N-terminus of the peptide ligand is joined to the N-terminus or C-terminus of the multimerization domain are also possible.

Preferred multimerization domains are immunoglobulin constant region sequences. Typically, in such fusions the encoded hybrid molecule will retain at least functionally active hinge, CH2 and CH3 domains of the constant region of an immunoglobulin heavy chain. Fusions are also made, for example, to the C-terminus of the Fc portion of a constant domain, or immediately N-terminal to the CH1 of the heavy chain or the corresponding region of the light chain.

The precise amino acid site at which the fusion of the peptide ligand to the immunoglobulin constant domain is made is not critical; particular sites are well known and may be selected in order to optimize the biological activity, secretion, or binding characteristics. In this regard, the skilled artisan may reference the construction of various immunoadhesins described in the literature (U.S. Pat. Nos. 5,116,964, 5,714,147 and 5,336,603; Capon et al., (1989) Nature 337:525–531; Traunecker et al., (1989) Nature 339:68–70; and Byrn et al., (1990) Nature 344:667–670; Watson et al., (1990) J. Cell. Biol. 110:2221–2229; Watson et al., (1991) Nature 349:164–167; Aruffo et al., (1990) Cell 61:1303–1313; Linsley et al., (1991) J. Exp. Med. 173:721–730; Lisley et al., J. Exp. Med. 174:561–569; Stamenkovic et al., Cell 66:1133–1144; Ashkenazi et al., (1991) Proc. Natl. Acad. Sci. USA 88:10535–10539; Lesslauer et al., (1991) Eur. J. Immunol. 27:2883–2886; and Peppel et al., (1991) J. Exp. Med. 174:1483–1489; Mohler et al., (1993) J. Immunol. 151:1548–1561); Bennett et al., (1991) J. Biol. Chem. 266:23060–23067; Kurschner et al., (1992) J. Biol. Chem. 267:9354–9360; Chalupny et al., (1992) PNAS USA 89:10360–10364; Ridgway and Gorman, (1991) J. Cell. Biol. 115, Abstract No. 1448).

According to a particular aspect, an immunoglobulin type multimerization domain is selected to provide a multimer such as a dimer having a functional Fc. In preferred aspects the multimerization domain is selected to provide an Fc domain having an effector function associated with a native immunoglobulin Fc region. Therefore, the peptide ligand is joined, in particular aspects, to an immunoglobulin heavy chain constant domain to provide a multimer comprising a functional Fc domain selected for a particular effector function or functions. In this case, DNA encoding an immunoglobulin chain-peptide ligand sequence is typically coexpressed with the DNA encoding a second peptide ligand-immunoglobulin heavy chain fusion protein. Upon secretion, the hybrid heavy chain will be covalently associated to provide an immunoglobulin-like structure comprising two disulfide-linked immunoglobulin heavy chains. The skilled artisan will recognize that effector functions include, for example, C1q binding; complement dependent cytotoxicity; Fc receptor binding; antibody-dependent cell-mediated cytotoxicity (ADCC); phagocytosis; and down regulation of cell surface receptors (e.g. B cell receptor; BCR) and prolonging half-life through incorporation of the salvage receptor binding ligand as described in, for example, U.S. Pat. No. 5,739,277 issued Apr. 14, 1998.

Preferably, the Fc region is a human Fc region, e.g. a native sequence human Fc region human IgG1 (A and non-A allotypes), IgG2, IgG3 or IgG4 Fc region. Such sequences are shown in FIGS. 2 & 3. Additionally, by introducing the appropriate amino acid sequence modifications in a parent Fc region, one can generate a variant Fc region which (a) mediates antibody-dependent cell-mediated cytotoxicity (ADCC) in the presence of human effector cells more effectively and/or (b) binds an Fc gamma receptor (Fc(R) with better affinity than the native sequence. Such Fc region variants will generally comprise at least one amino acid modification in the Fc region.

In a preferred embodiment, the peptide ligand sequence is fused to the N-terminus of the Fc region of immunoglobulin $G_1$ ($IgG_1$). It is possible to fuse the entire heavy chain constant region to the peptide ligand sequence. However, more preferably, a sequence beginning in the hinge region just upstream of the papain cleavage site which defines IgG Fc chemically (i.e. residue 216, taking the first residue of heavy chain constant region to be 114), or analogous sites of other immunoglobulins is used in the fusion. In a particularly preferred embodiment, the peptide ligand amino acid sequence is fused to (a) the hinge region (or other linker domain) and CH2 and CH3 or (b) the CH1, hinge, CH2 and CH3 domains, of an IgG heavy chain. In a further preferred embodiment the peptide ligand amino acid sequence is fused to (a) the hinge region (or other linker domain) and (b) the CH3 domain of an IgG1 (see, for example, the constructs described in Hu et al., (1996) Cancer Res. 56:3055–3061).

According to a particular aspect of this embodiment, hybrid molecules comprising a peptide ligand and a multimerization domain are assembled as multimers, for example homodimers, or heterodimers or even heterotetramers. Homodimers result from the pairing or crosslinking of two monomers comprising a peptide ligand and a multimerization domain. However, it is not essential that two identical monomers pair. According to a particular aspect of the invention a hybrid molecule as defined herein comprising a peptide ligand and a multimerization domain such as an immunoglobulin constant domain may pair with a) companion immunoglobulin chain comprising one arm of an immunoglobulin. Various exemplary assembled hybrid molecules within the scope of the present invention are schematically diagramed below:

(a) ACH
(b) ACH-ACH
(c) ACH-VHCH-VLCL
(d) ACH-VHCH wherein each A represents identical or different peptide ligands;
VL is an immunoglobulin light chain variable domain;
VH is an immunoglobulin heavy chain variable domain;
CL is an immunoglobulin light chain constant domain and
CH is an immunoglobulin heavy chain constant domain.

In the interests of brevity, the foregoing structures only show key features; they do not show optional linker domains between the peptide ligand domains and the multimerization domains as described herein below; they do not indicate joining, hinge or other domains of the immunoglobulins, nor are disulfide bonds shown. However, where such domains are required for binding activity, they are constructed to be present in the ordinary locations which they occupy in the immunoglobulin molecules.

Although the presence of an immunoglobulin light chain is not required in the hybrid molecules of the present invention, an immunoglobulin light chain might be present either covalently associated to a peptide ligand-immunoglobulin heavy chain fusion polypeptide, or directly fused to the peptide ligand. In the former case, DNA encoding an immunoglobulin light chain is typically coexpressed with the DNA encoding the peptide ligand-immunoglobulin heavy chain fusion protein. Upon secretion, the hybrid heavy chain and the light chain will be covalently associated to provide an immunoglobulin-like structure comprising two disulfide-linked immunoglobulin heavy chain-light chain pairs.

The hybrid molecules described herein are most conveniently constructed by fusing the cDNA sequence encoding the peptide ligand portion in-frame to an immunoglobulin cDNA sequence. However, fusion to genomic immunoglobulin fragments can also be used (see, e.g. Aruffo et al., (1990), Cell 61:1303–1313; and Stamenkovic et al. (1991), Cell 66:1133–1144). The latter type of fusion requires the presence of Ig regulatory sequences for expression. cDNAs encoding IgG heavy-chain constant regions can be isolated based on published sequences from cDNA libraries derived from spleen or peripheral blood lymphocytes, by hybridization or by polymerase chain reaction (PCR) techniques. The cDNAs encoding the peptide ligand and the immunoglobulin parts of the hybrid molecule are inserted in tandem into a plasmid vector that directs efficient expression in the chosen host cells.

Alternatively, and especially in embodiments where the peptide ligand is synthesized by, for example standard solid phase synthesis techniques, the peptide ligand may be linked to the multimerization domain by any of a variety of means familiar to those of skill in the art. Covalent attachment is typically the most convenient, but other forms of attachment may be employed depending upon the application. Examples of suitable forms of covalent attachment include the bonds resulting from the reaction of molecules bearing activated chemical groups with amino acid side chains in the multimerization domain and can be made using a variety of bifunctional protein coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene).

The invention includes the specific targeting of, for example HER2 bearing cell types, in vivo via the peptide ligands and according to this aspect of the present invention, conferring an Fc effector function such as Fc receptor binding, complement fixation, protein A binding, increasing half-life or crossing the blood brain barrier to the molecule.

B. Peptide Ligand Fusions

According to the present invention, the peptide ligand domain is optionally linked to, for example, another peptide ligand domain either directly or via a flexible peptide linker as described below. According to the present invention, the linker domain, is any group of molecules that provides a spatial bridge between two or more peptide ligand domains as described in more detail herein below. According to this aspect of the invention, peptide ligands are linked together, as for example in a fusion protein. The hybrid molecules of this aspect of the invention are useful in, for example, cross-linking two or more receptors.

C. Linker Domains

According to the present invention, the peptide ligand domain is optionally linked to, for example, another peptide ligand domain or a multimerization domain via a flexible peptide linker. The linker component of the hybrid molecule of the invention does not necessarily participate in but may contribute to the function of the hybrid molecule. Therefore, according to the present invention, the linker domain, is any group of molecules that provides a spatial bridge between two or more peptide ligand domains or a peptide ligand domain and a mulitmerization domain.

The linker domain can be of variable length and makeup. It is generally, the orientation caused by the linker domain and not its chemical structure that is important. The linker domain preferably allows for the peptide ligand domain of the hybrid molecule to bind, substantially free of spacial/conformational restrictions to the coordinant ErbB2 molecule. Therefore, the length of the linker domain is dependent upon the character of the two functional, e.g., the peptide ligand and the multimerization domains of the hybrid molecule.

One skilled in the art will recognize that various combinations of atoms provide for variable length molecules based upon known distances between various bonds (Morrison, and Boyd, Organic Chemistry, 3rd Ed, Allyn and Bacon, Inc., Boston, Mass. (1977)). For example, the linker domain may be a polypeptide of variable length. The amino acid composition of the polypeptide determines the character and length of the linker. Exemplary, linker domains comprises between 2 and 10 amino acids, preferably about 6 amino acids as, for example, Gly-Gly-Gly-Ser-Gly-Gly (SEQ ID NO:129), Gly-Gly-Gly-Ser-Ser-Gly (SEQ ID NO:130), and Gly-Gly-Gly-Arg-Gly-Gly (SEQ ID NO:131).

D. Other Bispecific Combinations

According to certain aspects of the invention, bi- or dual-specific compositions comprising at least one peptide ligand domain are envisioned. For example, bispecific antibody compositions have been produced using leucine zippers (Kostelny et al., (1992) J. Immunol., 148(5): 1547–1553). The leucine zipper peptides from the Fos and Jun proteins are linked to the Fab' portions of two different antibodies by gene fusion. The antibody homodimers can be reduced at the hinge region to form monomers and then re-oxidized to form antibody heterodimers. This method can also be utilized for the production of peptide ligand homodimer and heterodimers utilizing the peptide ligands in place of the binding domains of the antibody heterodimers.

Recombinant Synthesis

The present invention encompasses a composition of matter comprising isolated nucleic acid, preferably DNA, encoding a peptide described herein. DNAs encoding the peptides of the invention can be prepared by a variety of methods known in the art. These methods include, but are not limited to, chemical synthesis by any of the methods described in Engels et al., (1989) Agnew. Chem. Int. Ed. Engl., 28:716–734, the entire disclosure of which is incorporated herein by reference, such as the triester, phosphite, phosphoramidite and H-phosphonate methods. In one embodiment, codons preferred by the expression host cell are used in the design of the encoding DNA. Alternatively, DNA encoding the peptide can be altered to encode one or more variants by using recombinant DNA techniques, such as site specific mutagenesis (Kunkel et al., (1991) Methods Enzymol. 204:125–139; Carter, P., et al., (186) Nucl. Acids. Res. 13:4331; Zoller, M. J. et al., (1982) Nucl. Acids Res. 10:6487), cassette mutagenesis (Wells, J. A., et al., (1985) Gene 34:315), restriction selection mutagenesis (Wells, J. A., et al., (1986) Philos. Trans, R. Soc. London SerA 317, 415), and the like.

The invention further comprises an expression control sequence operably linked to the DNA molecule encoding a peptide of the invention, and an expression vector, such as a plasmid, comprising the DNA molecule, wherein the control sequence is recognized by a host cell transformed with the vector. In general, plasmid vectors contain replication and control sequences which are derived from species compatible with the host cell. The vector ordinarily carries a replication site, as well as sequences which encode proteins that are capable of providing phenotypic selection in transformed cells.

Suitable host cells for expressing the DNA include prokaryote, yeast, or higher eukaryote cells. Suitable prokaryotes include but are not limited to eubacteria, such as Gram-negative or Gram-positive organisms, for example, Enterobacteriaceae such as *E. coli*. Various *E. coli* strains are publicly available, such as *E. coli* K12 strain MM294 (ATCC 31,446); *E. coli* X1776 (ATCC 31,537 γ*E. coli* strain W3110 (ATCC 27,325) and K5 772 (ATCC 53,635).

In addition to prokaryotes, eukaryotic organisms, such as yeasts, or cells derived from multicellular organisms can be used as host cells. For expression in yeast host cells, such as common baker's yeast or *Saccharomyces cerevisiae*, suitable vectors include episomally replicating vectors based on the 2-micron plasmid, integration vectors, and yeast artificial chromosome (YAC) vectors. Suitable host cells for expression also are derived from multicellular organisms. Examples of invertebrate cells include insect cells such as *Drosophila* S2 and *Spodoptera* Sf9, as well as plant cells. For expression in insect host cells, such as Sf9 cells, suitable vectors include baculoviral vectors. For expression in plant host cells, particularly dicotyledonous plant hosts, such as tobacco, suitable expression vectors include vectors derived from the Ti plasmid of *Agrobacterium tumefaciens*.

Examples of useful mammalian host cells include monkey kidney CV1 line transformed by SV40 (COS-7, ATCC CRL 1651); human embryonic kidney line (293 or 293 cells subcloned for growth in suspension culture, Graham et al., (1977) J. Gen Virol., 36:59); baby hamster kidney cells (BHK, ATCC CCL 10); Chinese hamster ovary cells/-DHFR (CHO, Urlaub and Chasin, (1980) Proc. Natl. Acad. Sci. USA, 77:4216); mouse sertoli cells (TM4, Mather, (1980) Biol. Reprod., 23:243–251); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., (1982) Annals N.Y. Acad. Sci., 383:44–68); MRC 5 cells; FS4 cells; and a human hepatoma cell line (Hep G2).

For expression in prokaryotic hosts, suitable vectors include pBR322 (ATCC No. 37,017), phGH107 (ATCC No. 40,011), pBO475, pS0132, pRIT5, any vector in the pRIT20 or pRIT30 series (Nilsson and Abrahmsen, (1990) Meth. Enzymol., 185:144–161), pRIT2T, pKK233-2, pDR540 and pPL-lambda. Prokaryotic host cells containing the expression vectors of the present invention include *E. coli* K12 strain 294 (ATCC NO. 31446), *E coli* strain JM101 (Messing et al.,(1981) Nucl. Acid Res., 9:309), *E. coli* strain B, *E. coli* strain χ1776 (ATCC No. 31537), *E. coli* c600 (Appleyard, *Genetics*, 39: 440 (1954)), *E. coli* W3110 (F-, gamma-, prototrophic, ATCC No. 27325), *E. coli* strain 27C7 (W3110, tonA, phoA E15, (argF-lac)169, ptr3, degP41, ompT, kan') (U.S. Pat. No. 5,288,931, ATCC No. 55,244), *Bacillus subtilis, Salmonella typhimurium, Serratia marcesans*, and *Pseudomonas species*.

For expression in mammalian host cells, useful vectors include vectors derived from SV40, vectors derived from cytomegalovirus such as the pRK vectors, including pRK5 and pRK7 (Suva et al., (1987) Science, 237:893–896; EP 307,247 (Mar. 15, 1989), EP 278,776 (Aug. 17, 1988)) vectors derived from vaccinia viruses or other pox viruses, and retroviral vectors such as vectors derived from Moloney's murine leukemia virus (MoMLV).

Optionally, the DNA encoding the peptide of interest is operably linked to a secretory leader sequence resulting in secretion of the expression product by the host cell into the culture medium. Examples of secretory leader sequences include stII, ecotin, lamB, herpes GD, lpp, alkaline phosphatase, invertase, and alpha factor. Also suitable for use herein is the 36 amino acid leader sequence of protein A (Abrahmsen et al., (1985) EMBO J., 4:3901).

Host cells are transfected and preferably transformed with the above-described expression or cloning vectors of this invention and cultured in conventional nutrient media modified as appropriate for inducing promoters, selecting transformants, or amplifying the genes encoding the desired sequences.

Transfection refers to the taking up of an expression vector by a host cell whether or not any coding sequences are in fact expressed. Numerous methods of transfection are known to the ordinarily skilled artisan, for example, $CaPO_4$ precipitation and electroporation. Successful transfection is generally recognized when any indication of the operation of this vector occurs within the host cell.

Transformation means introducing DNA into an organism so that the DNA is replicable, either as an extrachromosomal element or by chromosomal integrant. Depending on the host cell used, transformation is done using standard techniques appropriate to such cells. The calcium treatment employing calcium chloride, as described in section 1.82 of Sambrook et al., Molecular Cloning (2nd ed.), Cold Spring Harbor Laboratory, NY (1989), is generally used for prokaryotes or other cells that contain substantial cell-wall barriers. Infection with *Agrobacterium tumefaciens* is used for transformation of certain plant cells, as described by Shaw et al., (1983) Gene, 23:315 and WO 89/05859 published 29 Jun. 1989. For mammalian cells without such cell walls, the calcium phosphate precipitation method described in sections 16.30–16.37 of Sambrook et al., supra, is preferred. General aspects of mammalian cell host system transformations have been described by Axel in U.S. Pat. No. 4,399,216 issued 16 Aug. 1983. Transformations into yeast are typically carried out according to the method of Van Solingen et al., (1977) J. Bact., 130:946 and Hsiao et al., (1979) Proc. Natl. Acad. Sci. (USA), 76:3829. However, other methods for introducing DNA into cells such as by nuclear injection, electroporation, or by protoplast fusion may also be used.

Other preferred vectors can be constructed using standard techniques by combining the relevant traits of the vectors described above. Relevant traits include the promoter, the ribosome binding site, the gene of interest or gene fusion (the Z domain of protein A and the gene of interest and a linker), the antibiotic resistance markers, and the appropriate origins of replication. A variation on the above procedures contemplates the use of gene fusions, wherein the gene encoding the desired peptide is associated, in the vector, with a gene encoding another protein or a fragment of another protein. This results in the desired peptide being produced by the host cell as a fusion with another protein or peptide. The "other" protein or peptide is often a protein or peptide which can be secreted by the cell, making it possible to isolate and purify the desired peptide from the culture medium and eliminating the necessity of destroying the host cells which arises when the desired peptide remains inside the cell. Alternatively, the fusion protein can be expressed intracellularly. It is useful to use fusion proteins that are highly expressed.

The use of gene fusions, though not essential, can facilitate the expression of heterologous peptides in insect cells as well as the subsequent purification of those gene products. Protein A fusions are often used because the binding of protein A, or more specifically the Z domain of protein A, to IgG provides an "affinity handle" for the purification of the fused protein. For example, a DNA sequence encoding the desired peptide ligand can be fused by site directed mutagenesis to the gene for a consensus domain of protein A known as the Z domain (Nilsson et al., (1987) Protein Engineering 1:107–113). After expression and secretion the fusion protein can be enzymatically cleaved to yield free peptide which can be purified from the enzymatic mix (see, e.g., Varadarajan et al., (1985) Proc. Natl. Acad. Sci USA 82:5681–5684; Castellanos-Serra et al., (1996) FEBS Letters 378:171–176; Nilsson et al., (1996) J. Biotechnol. 48:241–250).

Fusion proteins can be cleaved using chemicals, such as cyanogen bromide, which cleaves at a methionine, or hydroxylamine, which cleaves between an Asn and Gly residue. Using standard recombinant DNA methodology, the nucleotide base pairs encoding these amino acids may be inserted just prior to the 5' end of the gene encoding the desired peptide.

Alternatively, one can employ proteolytic cleavage of fusion protein. Carter, in *Protein Purification: From Molecular Mechanisms to Large-Scale Processes*, Ladisch et al., eds. (American Chemical Society Symposium Series No. 427, 1990), Ch 13, pages 181–193.

Proteases such as Factor Xa, thrombin, and subtilisin or its mutants, and a number of others have been successfully used to cleave fusion proteins. Preferred according to the present invention for the production of peptide ligands of less than about 30 amino acids is the protease trypsin which is highly specific for Arg and Lys residues. Trypsin cleavage is discussed generally in Nilsson et al. (1996) J. Biotech. 48:241 and Smith et al., Methods Mol. Biol. 32:289. Typically, a peptide linker that is amenable to cleavage by the protease used is inserted between the "other" protein (e.g., the Z domain of protein A) and the desired peptide. Using recombinant DNA methodology, the nucleotide base pairs encoding the linker are inserted between the genes or gene fragments coding for the other proteins. Proteolytic cleavage of the partially purified fusion protein containing the correct linker can then be carried out on either the native fusion protein, or the reduced or denatured fusion protein.

The peptide may or may not be properly folded when expressed as a fusion protein. Also, the specific peptide linker containing the cleavage site may or may not be accessible to the protease. These factors determine whether the fusion protein must be denatured and refolded, and if so, whether these procedures are employed before or after cleavage.

When denaturing and refolding are needed, typically the peptide is treated with a chaotrope, such a guanidine HCl, and is then treated with a redox buffer, containing, for example, reduced and oxidized dithiothreitol or glutathione at the appropriate ratios, pH, and temperature, such that the peptide is refolded to its native structure.

The host cells referred to in this disclosure encompass cells in in vitro culture as well as cells that are within a host animal.

In cyclized embodiments of the invention, the recombinantly produced peptide can be cyclized by formation of an intramolecular disulfide bond as described above.

Utility

Generally speaking, the peptide ligands and hybrid molecules of the present invention can be used in the same applications as, for example, native or variant heregulin molecules or antibodies directed against ErbB2 may be used. Of course, some peptide ligands or hybrid molecules within the scope of the present invention may be better suited for a particular application than another application.

Those skilled in the art will readily ascertain which molecules are appropriate for a given application by using one or more conventional biological assay to determine the biological activity of the peptide ligand or hybrid molecule.

As but an example, the heregulins are useful in the treatment of a variety of disorders, for example, disorders and diseases affecting the nervous system, musculature and epithelia. For example, an agonist peptide ligand or hybrid molecule of the present invention may be used in promoting the development, maintenance and or regeneration of a neuron in vivo in the same manner that heregulin or a heregulin variant may be used. Diseases or disorders amenable to treatment with peptide ligands or hybrid molecules according to this aspect of the invention include, for example, central nervous system damage attendant to trauma, surgery, stroke, ischemia, infection, metabolic disorders nutritional deficiency, malignancy or a toxic agent. Neurodegenerative disorders my also be treated included but not limited to human neurodegenerative diseases or disorders such as Alzheimer's disease, Parkinson's disease, epilepsy, multiple sclerosis, Huntington's chorea, Downs syndrome, nerve deafness and Meniere's disease. As well, particular peptide ligands are suited for use in the treatment of neuropathy, such as peripheral neuropathy associated with systemic diseases or disorders such as diabetes.

Agonist peptide ligands which upon binding ErbB2 initiate a phosphorylation event as described are especially useful the foregoing aspects of the invention. Specific agonist peptide ligands of the invention are capable of enhancing the survival of cells, which is to say they increase the period of survival of an ErbB2 bearing cell either in vivo or in vitro relative to the period of survival of cells that have not been exposed to a particular agonist peptide ligand. In preferred embodiments, the agonist peptide ligand causes or enhances the proliferation of ErbB2 bearing cell types, either in vivo or in vitro, as quantified by, for example, measuring $^3$H-thymidine uptake by cells. Proliferation may be associated with differentiation of ErbB2 cells as determined by screening an ErbB2 bearing cell population for phenotypic changes.

According to another aspect of the present invention, certain peptide ligands and hybrid molecules, especially those that bind ErbB2 but do not elicit an agonist associated response, are useful in, for example, inhibiting tumor cell invasion and metastasis as described more fully herein below. For example, a tumor that expresses ErbB2 receptors (especially one which overexpresses ErbB2) can be treated using a peptide ligand or hybrid molecule conjugated to a cytotoxic agent or in targeting a prodrug to cells expressing ErbB2.

A. Effector Function Engineering

For example, it may be desirable to modify the multimerization domain of hybrid molecules of the present invention with respect to effector function, to, for example, enhance the effectiveness of the antibody in treating cancer. For example, cysteine residue(s) may be introduced in an immunoglobulin Fc region, thereby allowing interchain disulfide bond formation in this region. The homo- or heterodimeric hybrid molecule thus generated may have improved internalization capability and/or increased complement-mediated cell killing and antibody-dependent cellular cytotoxicity (ADCC). See Caron et al., (1992) J. Exp Med. 176:1191–1195 and Shopes, B. (1992) J. Immunol. 148:2918–2922. Homodimeric hybrid molecules with enhanced anti-tumor activity may also be prepared using heterobifunctional cross-linkers as described in Wolff et al. (1993) Cancer Research 53:2560–2565.

Alternatively, an heterodimeric hybrid molecule can be engineered which has dual Fc regions and may thereby have enhanced complement lysis and ADCC capabilities. See Stevenson et al. (1989) Anti-Cancer Drug Design 3:219–230.

B. Conjugates

The invention also pertains to conjugates comprising the peptide ligands or any of the hybrid molecules described herein conjugated to a cytotoxic agent such as a chemotherapeutic agent, such as a protein toxin or cytotoxic drug or toxin (e.g. an enzymatically active toxin of bacterial, fungal, plant or animal origin, or fragments thereof), or a radioactive isotope (i.e., a radioconjugate).

Chemotherapeutic agents useful in the generation of such immunoconjugates have been described. A chemotherapeutic agent is a chemical compound useful in the treatment of cancer including carcinoma, lymphoma, blastoma, sarcoma, and leukemias. Examples of chemotherapuetic agents include, antibiotics isolated from microorganisms such as the calicheamicins (Lee et al., (1987) J. Am. Chem. Soc. 109:3464–3466; Hinman et al., (1993) Cancer Res. 53:3336–3342), maytansinoids (such as those described in Liu et al. (1996) Proc. Natl. Acad. Sci. USA 93:8618–8323), Adriamycin, Doxorubicin, 5-Fluorouracil, Cytosine arabinoside, Cyclophophamide, thiotepa, Busulfan, Cytoxin, Taxol, Methotrexate, Cisplatin, Melphalan, Vinblastin, Bleomycin, Etoposide, Ifosfamide, Mitomycin C, Mitosantrone, Vincristine, Vinorelbine, Carboplatin, Teniposide, Daunomycin, Caminomydcin, Aminopterin, Dactinomycin, a Mitomycin, Nicotinamide, an Espeeramicin, Melphalan and any related nitrogen mustard, and endocrine therapeutics (such as diethylstilbestrol, Tamoxifen, LHRH-antagonizing drugs, a progestin, an anti-progestin, etc.)

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), momordica charantia inhibitor, curcin, crotin, sapaonaria officinalis inhibitor, gelonin, mitogellin, restrictocin, phenomycin, enomycin and the tricothecenes.

A variety of radionuclides are available for the production of radioconjugated peptide ligands or hybrid molecules. Examples include $^{212}Bi$, $^{131}I$, $^{131}In$, $^{90}Y$ and $^{186}Re$. Carbon-14-labeled 1-isothiocyanatobenzyl-3-methyldiethylene triaminepentaacetic acid (MX-DTPA) is an exemplary chelating agent for conjugation of radionucleotide to the hybrid molecules.

Conjugates of the peptide ligand or hybrid molecule and a cytotoxic agent are made using a variety of bifunctional protein coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared essentially as described in Vitetta et al. (1987) Science 238: 1098.

In another embodiment, the peptide ligand or hybrid molecules may be conjugated to a "receptor" (such streptavidin) for utilization in tumor pretargeting wherein the peptide ligand or hybrid molecule-receptor conjugate is administered to a patient, followed by removal of unbound conjugate from the circulation using a clearing agent and then administration of a "ligand" (e.g. avidin) which is conjugated to a cytotoxic agent (e.g. a radionucleotide).

C. Liposomes

The hybrid molecules or peptide ligands disclosed herein may also be formulated as liposomes. Liposomes containing the hybrid molecules are prepared by methods known in the art, such as described in Epstein et al., (1985) Proc. Natl. Acad. Sci. USA, 82:3688; Hwang et al., (1980) Proc. Natl. Acad. Sci. USA, 77:4030; and U.S. Pat. Nos. 4,485,045 and 4,544,545. Liposomes with enhanced circulation time are disclosed in U.S. Pat. No. 5,013,556.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. For example, hybrid molecules comprising an immunoglobulin constant domain as described herein can be conjugated to the liposomes as described in Martin et al. *J. Biol. Chem.* 257: 286–288 (1982) via a disulfide interchange reaction. A chemotherapeutic agent is optionally contained within the liposome. See Gabizon et al. *J. National Cancer Inst.* 81(19)1484 (1989).

D. Enzyme Mediated Prodrug Therapy

The peptide ligands or hybrid molecules of the present invention may also be used in the manner of antibodies of antibody dependent enzyme mediated prodrug therapy (ADEPT) by conjugating the peptide ligand or hybrid molecules to a prodrug-activating enzyme which converts a prodrug (e.g. a peptidyl chemotherapeutic agent, see WO81/01145) to an active anti-cancer drug. See, for example, WO 88/07378 and U.S. Pat. No. 4,975,278.

The enzyme component of the conjugate useful for ADEPT-type therapy includes any enzyme capable of acting on a prodrug in such a way so as to covert it into its more active, cytotoxic form. Enzymes that are useful in the method of this invention include, but are not limited to, alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as serratia protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as β-galactosidase and neuraminidase useful for converting glycosylated prodrugs into free drugs; β-lactamase useful for converting drugs derivatized with β-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes", can be used to convert the prodrugs of the invention into free active drugs (see, e.g., Massey, (1987) Nature 328:457–458). Peptide ligand/hybrid molecule-abzyme conjugates can be prepared as described herein for delivery of the abzyme to a tumor cell population.

Enzymes can be covalently bound to the hybrid molecules by techniques well known in the art such as the use of the heterobifunctional crosslinking reagents discussed above. Alternatively, fusion proteins comprising at least the peptide ligand portion of the hybrid molecule of the invention linked to at least a functionally active portion of an enzyme of the invention can be constructed using recombinant DNA techniques well known in the art (see, e.g., Neuberger et al., (1984) Nature, 312:604–608).

E. Pharmaceutical Compositions

Pharmaceutical compositions which comprise the peptide ligands of the invention may be administered in any suitable manner, including parental, topical, oral, or local (such as aerosol or transdermal) or any combination thereof. Suitable regimens also include an initial administration by intravenous bolus injection followed by repeated doses at one or more intervals.

Pharmaceutical compositions of the compounds of the invention are prepared for storage by mixing a peptide ligand containing compound having the desired degree of purity with optional pharmaceutically acceptable carriers, excipients or stabilizers (*Remington's Pharmaceutical Sciences* 16th edition, Osol, A. Ed. [1980]), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

The compositions herein may also contain more than one active compounds as necessary for the particular indication being treated, preferably those with complementary activities that do not adversely affect each other. For example, it may be desirable to further provide molecules, such as antibodies which bind to EGFR, ErbB2 (e.g. an antibody which binds a different ligand on ErbB2), ErbB3, ErbB4, or vascular endothelial factor (VEGF) in the one formulation. Alternatively, or in addition, the composition may comprise a cytotoxic agent, cytokine, growth inhibitory agent and/or cardioprotectant. Such molecules are suitably present in combination in amounts that are effective for the purpose intended.

F. Diagnosing and Prognosing a Disorder

Disorders for prognosis and diagnosis within the context of the present invention are preferably a benign or malignant tumor characterized by the overexpression of the ErbB2 receptor, e.g. a cancer, such as, breast cancer, squamous cell cancer, small-cell lung cancer, non-small cell lung cancer, gastrointestinal cancer, pancreatic cancer, glioblastoma, cervical cancer, ovarian cancer, liver cancer, bladder cancer, hepatoma, colon cancer, colorectal cancer, endometrial carcinoma, salivary gland carcinoma, kidney cancer, liver cancer, prostate cancer, vulval cancer, thyroid cancer, hepatic carcinoma and various types of head and neck cancer. Therefore, one embodiment of the present invention is directed to the detection and/or measurement of Erb2 in a sample and the use of such detection or measurement in the diagnosis, staging, determination of severity, and prognosis in general of the disorder.

In a particular embodiment, the diagnostic techniques described can be used to follow the progress of therapy. In a subject undergoing therapeutic treatment that results in an increase or a decrease in the amount of Erb2 bearing cells, the amount of Erb2 bearing cells in a sample may serve as a useful measure for the success or failure of the treatment. Thus, the present invention provides a method for monitoring the effect of a therapeutic treatment in a subject which comprises measuring at suitable time intervals the amount of Erb2 expressed in a sample of tissue suspected of containing Erb-2 expressing cells. The total amount of Erb2 is compared to a "baseline" or "control" value which depending on the disease, and the treatment, may be the amount of Erb2 in a similar sample from a normal subject, from the patient prior to disease onset or during remission of disease, or from the patient prior to the initiation of therapy. One of ordinary skill in the art will readily discern the appropriate baseline value to use in a particular situation without undue experimentation.

Any procedure known in the art for the measurement of analytes can be used in the practice of the measurement of Erb2 in a sample using the compounds of the present invention. Such procedures include but are not limited to competitive and non-competitive assay systems using techniques such as radioimmunoassays, enzyme immunoassays (EIA), preferably the enzyme linked immunosorbent assay (ELISA), "sandwich" immunoassays, precipitin reactions, gel diffusion reactions, immunodiffusion assays, agglutination assays, complement-fixation assays, immunoradiometric assays, fluorescent immunoassays, protein A immunoassays, and immunoelectrophoresis assays, to name but a few. For examples of preferred immunoassay methods, see U.S. Pat. No. 4,845,026 (Jul. 4, 1989) and U.S. Pat. No. 5,006,459 (Apr. 9, 1991).

For diagnostic and prognostic applications, a compound of the present invention, typically a hybrid molecule as described herein above will be labeled with a detectable moiety and used to detect Erb-2 in a sample as described above. Numerous labels are available which can be preferably grouped into the following categories:

(a) Radioisotopes, such as $^{35}S$, $^{14}C$, $^{125}I$, $^{3}H$, and $^{131}I$. The hybrid molecules can be labeled with the radioisotope using the techniques described in *Current Protocols in Immunology*, Volumes 1 and 2, Coligen et al., Ed., Wiley-Interscience, New York, N.Y., Pubs., (1991) for example and radioactivity can be measured using scintillation counting.

(b) Fluorescent labels such as rare earth chelates (europium chelates) or fluorescein and its derivatives, rhodamine and its derivatives, dansyl, Lissamine, phycoerythrin and Texas Red are available. The fluorescent labels can be conjugated to the hybrid molecules using the techniques disclosed in *Current Protocols in Immunology*, supra, for example. Fluorescence can be quantified using a fluorimeter.

(c) Various enzyme-substrate labels are available and U.S. Pat. No. 4,275,149 provides a review of some of these. The enzyme preferably catalyses a chemical alteration of the chromogenic substrate which can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light which can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, β-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are described in O'Sullivan et al., Methods for the Preparation of Enzyme-Antibody Conjugates for use in Enzyme Immunoassay, in *Methods in Enzym.* (ed J. Langone & H. Van Vunakis), Academic press, New York, 73: 147–166 (1981).

Examples of enzyme-substrate combinations include, for example:

(i) Horseradish peroxidase (HRPO) with hydrogen peroxidase as a substrate, wherein the hydrogen peroxidase oxidizes a dye precursor (e.g. orthophenylene diamine (OPD) or 3,3',5,5'-tetramethyl benzidine hydrochloride (TMB));

(ii) alkaline phosphatase (AP) with para-Nitrophenyl phosphate as chromogenic substrate; and (iii) β-D-galactosidase (β-D-Gal) with a chromogenic substrate (e.g. p-nitrophenyl-β-D-galactosidase) or fluorogenic substrate 4-methylumbelliferyl-β-D-galactosidase.

Numerous other enzyme-substrate combinations are available to those skilled in the art. For a general review of these, see U.S. Pat. Nos. 4,275,149 and 4,318,980.

In the assays of the present invention, a hybrid molecule is preferably bound to a solid phase support or carrier. By "solid phase support or carrier" is intended any support capable of binding an antigen or antibodies. Well-known supports, or carriers, include glass, polystyrene, polypropylene, polyethylene, dextran, nylon, amyloses, natural and modified celluloses, polyacrylamides, agaroses, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

In a preferred embodiment, a sandwich immunoassay is employed, i.e., Erb2 is detected or measured by a method comprising binding of a first antibody or hybrid molecule to the Erb2 antigen, and binding of a second antibody or hybrid molecule to the Erb2, and detecting or measuring Erb2 immunospecifically bound by both the first and second antibody or hybrid molecule. In a specific embodiment, either the first or second antibodies are monoclonal antibodies and either or both of the first and second are hybrid molecules of the present invention. In this embodiment, the peptide ligand portion of the hybrid molecule preferably binds to a site different from that of the first antibody (as reflected e.g., by the lack of competitive inhibition between the antibody and the hybrid molecule for binding to the antigen). In another specific embodiment, the first or second antibody is a polyclonal antibody.

Kits comprising one or more containers or vials containing components for carrying out the assays of the present invention are also within the scope of the invention. For instance, such a kit can comprise reagents required for the immunohistochemical analysis of a sample such as a tumor biopsy. Reagents may include one or more binding partners, e.g. a hybrid molecule or an antibody. For histological assays the kit contains the chromogenic substrate as well as a reagent for stopping the enzymatic reaction when color development has occurred. The substrate included in the kit is one appropriate for the enzyme conjugated to one of the hybrid molecules of the present invention. These are well-known in the art. The kit can optionally also comprise a standard, e.g., a known amount of purified Erb2.

The following examples are offered by way of illustration and not by way of limitation. The disclosures of all citations in the specification are expressly incorporated herein by reference.

EXAMPLES

Example I

Identification and Maturation of HER2 Binding Peptides

Methods

Phage Libraries—Random sequence polyvalent peptide phage libraries (Table 1) were constructed using large scale Kunkel mutagenesis of the template pB2479.g8. This phagemid contains the Tac promoter the mal signal sequence, 3 stop codons and a linker sequence fused to gVIII and includes the LacI$^q$ and ampicillin resistance genes. The peptide libraries are thus expressed polyvalently on phage as fusions to pVITT with the ability to regulate copy number with IPTG. Each library has a diversity in excess of $10^9$ clones.

TABLE 1

|  | Sequence |
|---|---|
| Pool 1 | $X_4CX_2GPX_4CX_4$ |
|  | $X_7CX_4CX_7$ |
|  | $X_7CX_5CX_6$ |
|  | $X_6CX_6CX_6$ |
| Pool 2 | $X_6CX_7CX_5$ |
|  | $X_5CX_8CX_5$ |
|  | $X_5CX_9CX_4$ |
|  | $X_4CX_{10}CX_4$ |
| Pool 3 | $X_8$ |
|  | $X_2CX_2CX_2$ |
|  | $X_2CX_3CX_2$ |
|  | $X_2CX_4CX_2$ |
| Pool 4 | $X_2CX_5CX_2$ |
|  | $X_2CX_6CX_2$ |
|  | $X_2CX_7CX_2$ |
| Pool 5 | $X_2CX_8CX_2$ |
|  | $X_2CX_9CX_2$ |
|  | $X_2CX_{10}CX_2$ |
| Pool 6 | $CCX_3CX_5C$ |
|  | $CCX_5CX_4CX_4CC$ |
| Pool 7 | $CXCX_7CX_3CX_6$ |
|  | $CX_6CX_6CCX_3CX_6C$ |

Selection Conditions—HER2-ECD was immobilized directly to maxisorp plates in 50 mM ammonium bicarbonate, pH 9.3, using 5 µg/ml, overnight at 4° C. Wells were blocked using PBS containing 1% BSA (PBS- BSA) for 1 hr at 25° C. The phage from the libraries described above were pooled into 7 groups as indicated in Table 1. Phage from each pool were incubated in wells containing HER2-ECD in PBS-BSA for 3 hr at 25° C.; generally about $5\times10^{10}$ phage were added at the beginning of each round. Unbound phage were removed by repetitive washing with PBS containing 0.05% Tween 20 (PBS-Tween); remaining phage were eluted with 500 mM KCl, 10 mM HCl, pH 2. The eluted phage were then amplified in XL1-Blue cells with VCSM13 helper phage (Stratagene) overnight at 37° C. IPTG (10 $\mu$M) was added only to the initial phage libraries and during amplification following round 1; later rounds relied on basal expression of the tac promoter for production of peptide-pVIII expression. Enrichment was monitored by titering the number of phage which bound to a target coated well compare to a well coated with BSA.

HER2 Phage Binding Assay—Inhibition of binding of phage displaying a single copy of peptide 1.1FI (Table 1) on their surface to the immobilized extracellular domain of Erb2 (HER2-ECD, Hudziak et al. (1991) J. Biol. Chem. 266:24109–15) was monitored using a phage ELISA. HER2-ECD was immobilized directly to Maxisorp plates (Nunc) in 50 mM ammonium bicarbonate, pH 9.3, using 5 $\mu$g/ml, overnight at 4° C. Wells were blocked using PBS containing 1% BSA (PBS-BSA) for 1 h at 25° C. Dilutions of 1.1FI-Fc in PBS-BSA were tested for their ability to block the binding of 1.1FI displaying phage to the immobilized HER2-ECD. The microtiter plate was washed with PBS containing 0.05% Tween20 (PBS-Tween) and the phage bound to HER2-ECD were detected with an anti-gVIII/HRP monoclonal antibody conjugate (Amersham Pharmacia Biotech). The amount of HRP bound Was measured using ABTS/$H_2O_2$ substrate and monitoring the change at 405 nm.

Results

Figure 4:
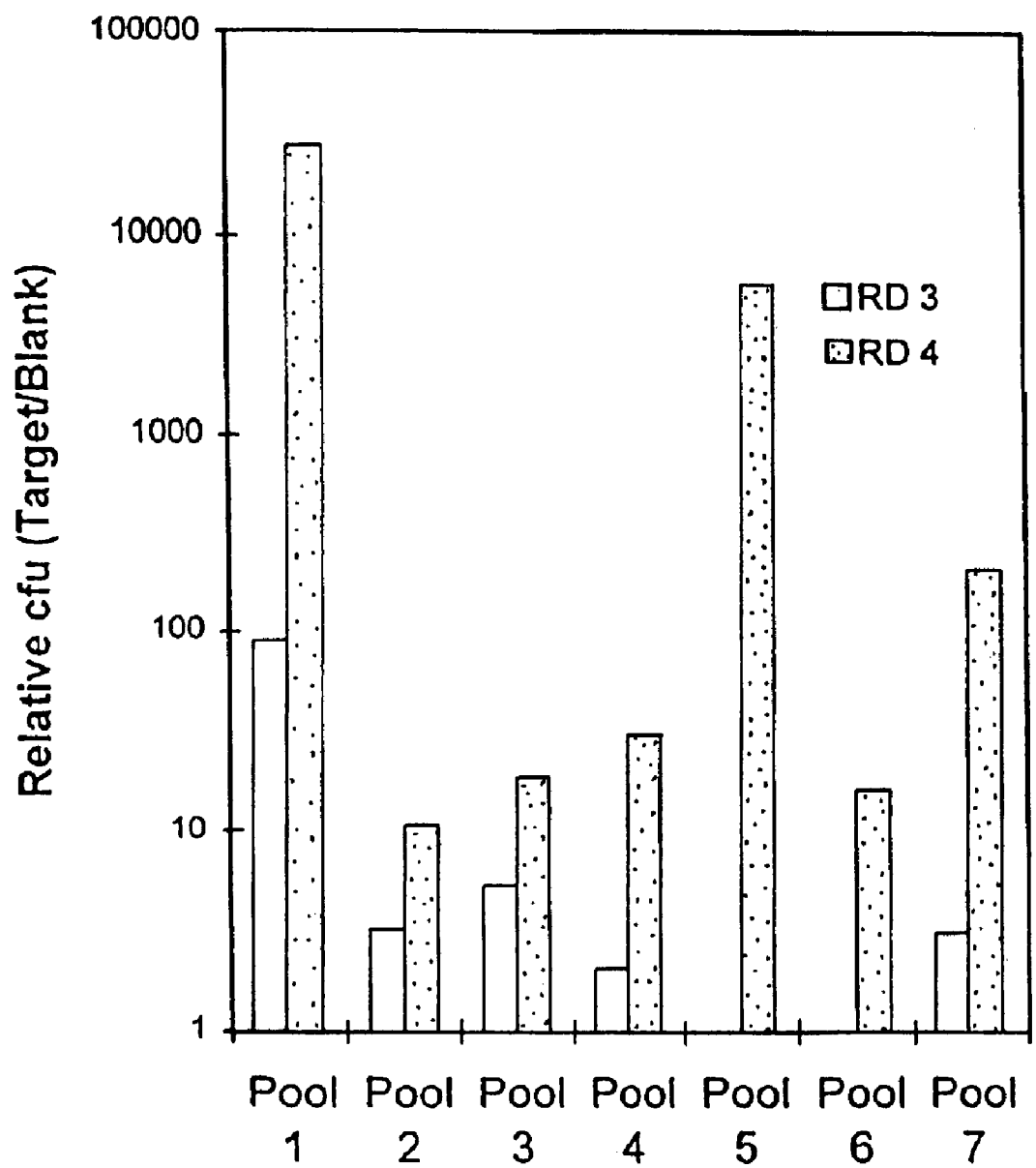
FIG. 4 shows the enrichment of polyvalent peptide phage that bind the HER2 extracellular domain (ECD). The ratio of phage eluted from a well coated with HER2 versus a well coated with BSA is shown for rounds 3 and 4 of selection.

Selection of Polyvalent Peptide-Phage That Bind to HER2-ECD—Polyvalent peptide libraries were sorted in 7 pools (Table 1) against immobilized HER2-ECD. Polyvalent phage display (Scott et al. (1990) Science 249:386–390) was used to enhance binding through avidity effects. Enrichment, the number of phage eluted from a well coated with HER2-ECD divided by the number of phage of eluted from a well coated with BSA, is shown in FIG. 4 for rounds 3 and 4. The DNA from random clones in each pool were sequenced and the deduced peptide sequences are presented in Table 2. Pool 1 was taken over by a single clone, while other pools contained multiple sequences.

Figure 5:
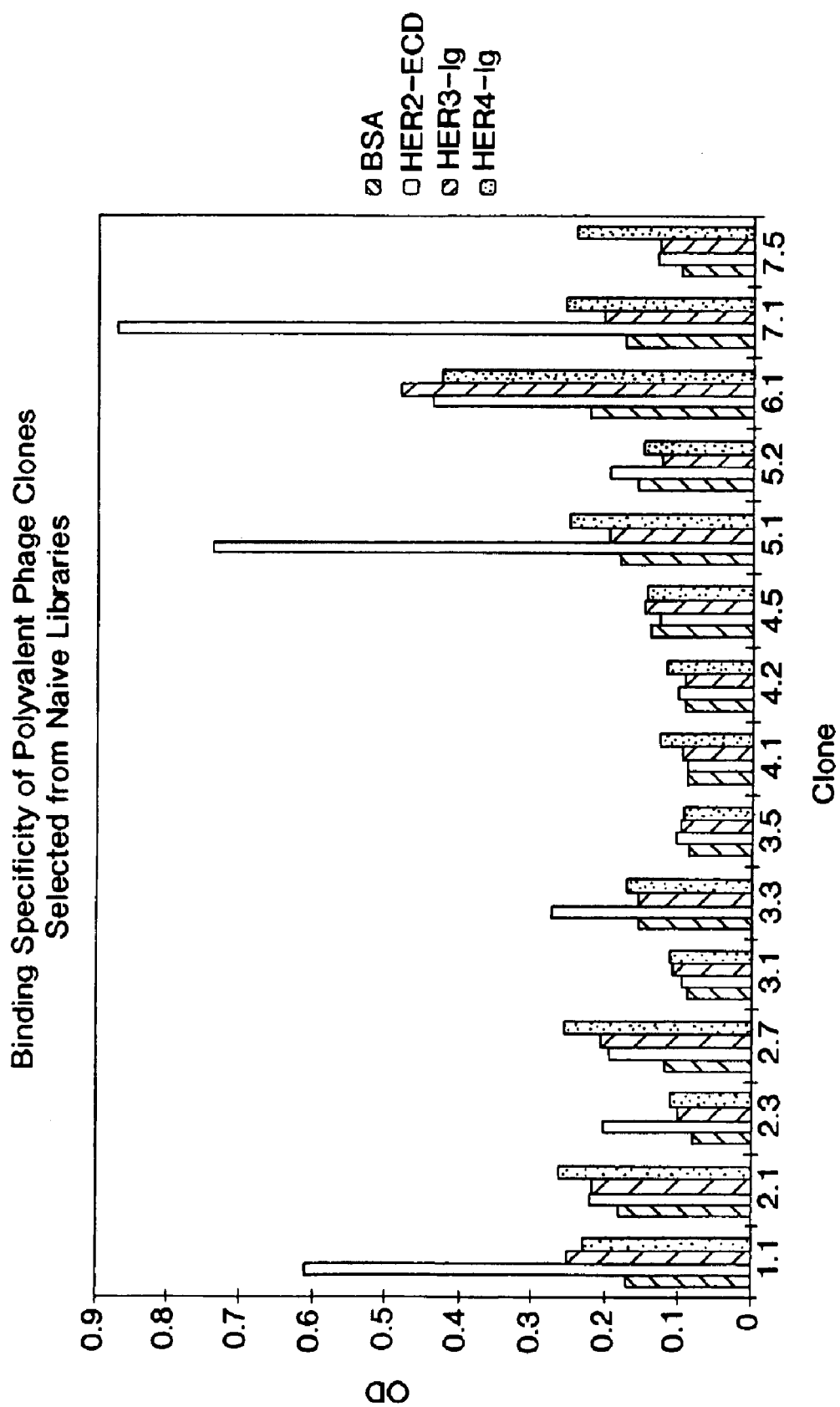
FIG. 5 shows the results of a phage binding assay. Phage clones 1.1, 5.1 and 7.1 were found to bind immobilized HER2-ECD, but not BSA or closely related HER3 or HER4 indicating they specifically recognized HER2-ECD.

Using a phage binding assay, phage clones 1.1, 5.1 and 7.1 were found to bind immobilized HER2-ECD, but not to immobilized BSA, or closely related HER3 or HER4 indicating they specifically recognized HER2-ECD (FIG. 5). The sequences of these clones were subjected to partial randomization in order to re-select for higher affinity clones.

TABLE 2

| clone | Sequence | SEQ ID NO: |
|---|---|---|
| Pool 1 | | |
| 1.1 | Y E V E A W D C M G P G C A N L F E A H | 132 |
| Pool 2 | | |
| 2.1 | S S E C A C D K G G R R V L C I N K V G | 133 |
| 2.3 | E P H G C S L W D W E L R T C S E Y A N | 134 |
| 2.5 | K E R P C A G D A P R K G V C H V A T H | 135 |
| 2.6 | K V R S C I E E S L D T R R C Y L V V E | 136 |
| 2.7 | A K T S S C G E H E E R R A V C V L S R | 137 |
| Pool 3 | | |
| 3.1 | K V W S V Q S P | 138 |
| 3.2 | G K V Q R C I P | 139 |
| 3.3 | Q T C R R V L C L P | 140 |
| 3.4 | R V W T W R W N | 141 |
| 3.5 | R I C T T P C A V | 142 |
| 3.6 | T S C R R V F C A V | 143 |
| 3.7 | R V C T G C V T | 144 |
| 3.8 | K V C T R V C C G T | 145 |
| Pool 4 | | |
| 4.1 | H P C H M R V L C A A | 146 |
| 4.2 | R G C K A T G K V L C S L | 147 |
| 4.3 | S G C L R A V G A C N T | 148 |

TABLE 2-continued

| clone | Sequence | SEQ ID NO: |
|---|---|---|
| 4.4 | A G C G S K A V C V S | 149 |
| 4.5 | R V W T A P Q C L I | 150 |
| 4.6 | K V C H A S S G C V A | 151 |
| 4.7 | R A C Q R A C L C P A | 152 |
| Pool 5 | | |
| 5.1 | R S C A D V A S R C W E H C I T | 153 |
| 5.2 | T D C G R V A S V C W E S C L I | 154 |
| Pool 6 | | |
| 6.1 | C C E T R W W C Q W C F C S G S A C C | 155 |
| 6.2 | G C K R V C S L G V M C | 156 |
| Pool 7 | | |
| 7.1 | C S W V L V Q C G G E W W H C C G L G C G L V V N A C | 157 |
| 7.5 | C G C E E R K A W K C Q E A C A R S G T V | 158 |

Example II

Methods

Partial or Complete Randomization on Monovalent Phage—Monovalent libraries which display a single copy of a peptide on the surface of phage fused through a linker sequence to the tail protein coded for by gIII were constructed using single-stranded template-directed mutagenesis (Kunkel et al. (1991) Met. Enz. 204:125–139) of a similar phagemid pB2479.g3. In this vector the coding sequence for gVIII has been replaced by a gIII, in addition, the $CMP^r$ gene has been inserted into a unique hincII site in the $AMP^r$ gene. The change in drug resistance was designed to eliminate contamination by related although weaker affinity polyvalent clones which could take over the population through avidity effects (Cwirla et al. (1990) Proc. Natl. Acad. Sci. USA 87:6378–6382). Partially randomized libraries were designed to maintain a bias towards the peptide sequences identified from the initial polyvalent libraries while allowing a 50% mutation rate at each amino acid position. This mutation rate was attained by synthesizing the oligos with a 70-10-10-10 mixture of bases (where each base in the doped region of the oligo is coupled using a mixture containing 70% of the base contributing to wildtype sequence and 10% each of the other 3 bases). In contrast, complete randomization in libraries was obtained by synthesizing oligos using NNS for particular codons in order to fully randomize portions of a displayed peptide while keeping other portions of the sequence constant.

Results

Partial Randomization of Peptide-Phage—The initial peptide libraries that were designed encoded a potential diversity of greater than $20^{20}$ ($10^{26}$) different clones while the actual libraries that were made contained approximately only $10^9$ clones; an incredibly small fraction of the potential diversity. In order to narrow the search and yet further explore the peptide diversity within the area of the initially selected peptides, a partial randomization technique was employed. This technique maintains a bias towards the wildtype sequence while introducing a 50% mutation rate (at the amino acid level) at each amino acid position; thus on average, a phage displayed 20 amino acid peptide would acquire 10 random mutations. In addition, anticipation of further affinity improvements led us to construct these libraries on monovalent phage (gIII) (Bass et al., (1990) Proteins: Struct. Funct. Genet. 8:309; Lowman et al., (1991) Biochemistry 30:10832) in order to eliminate avidity effects.

Figure 15A:
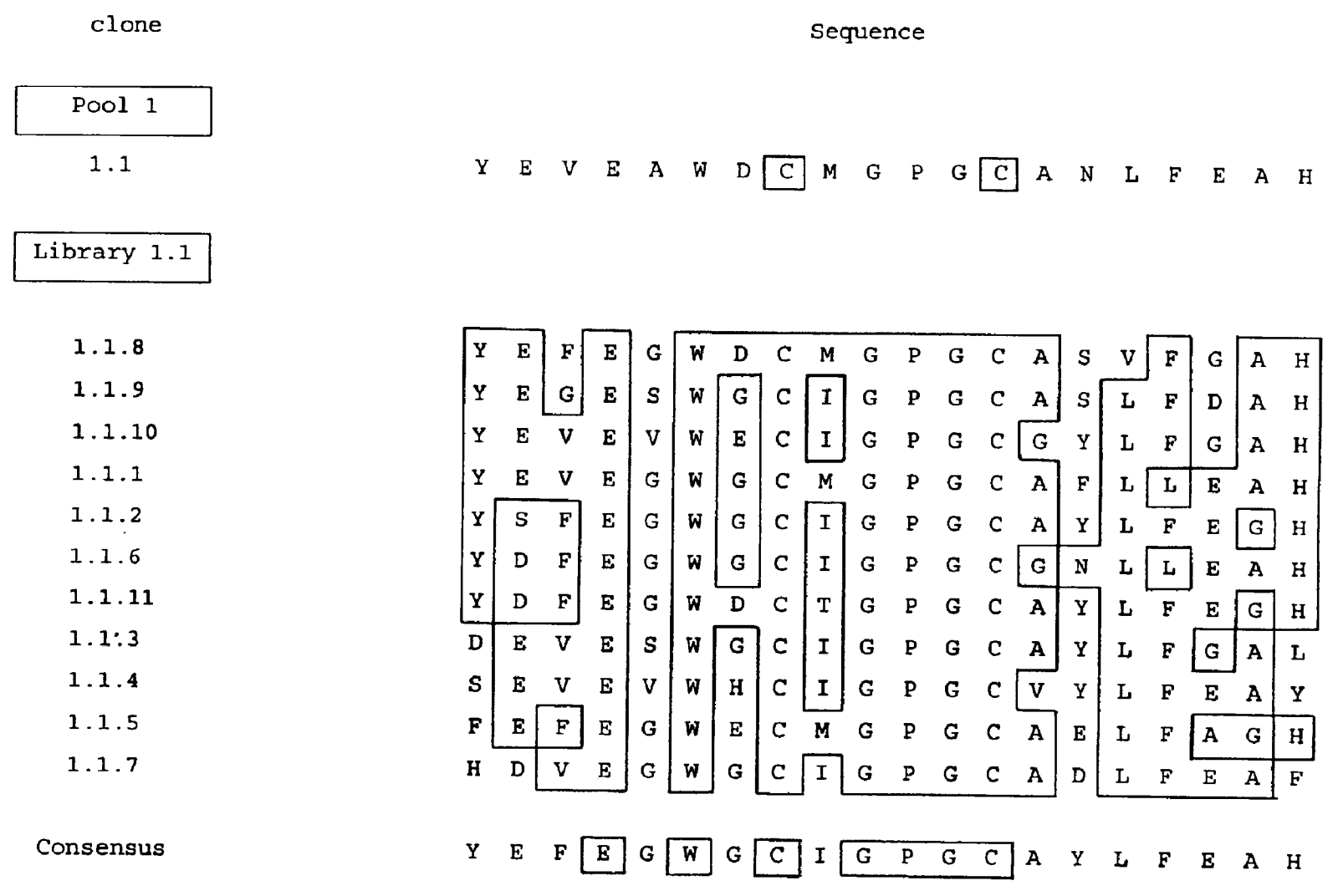
Figure 15B:
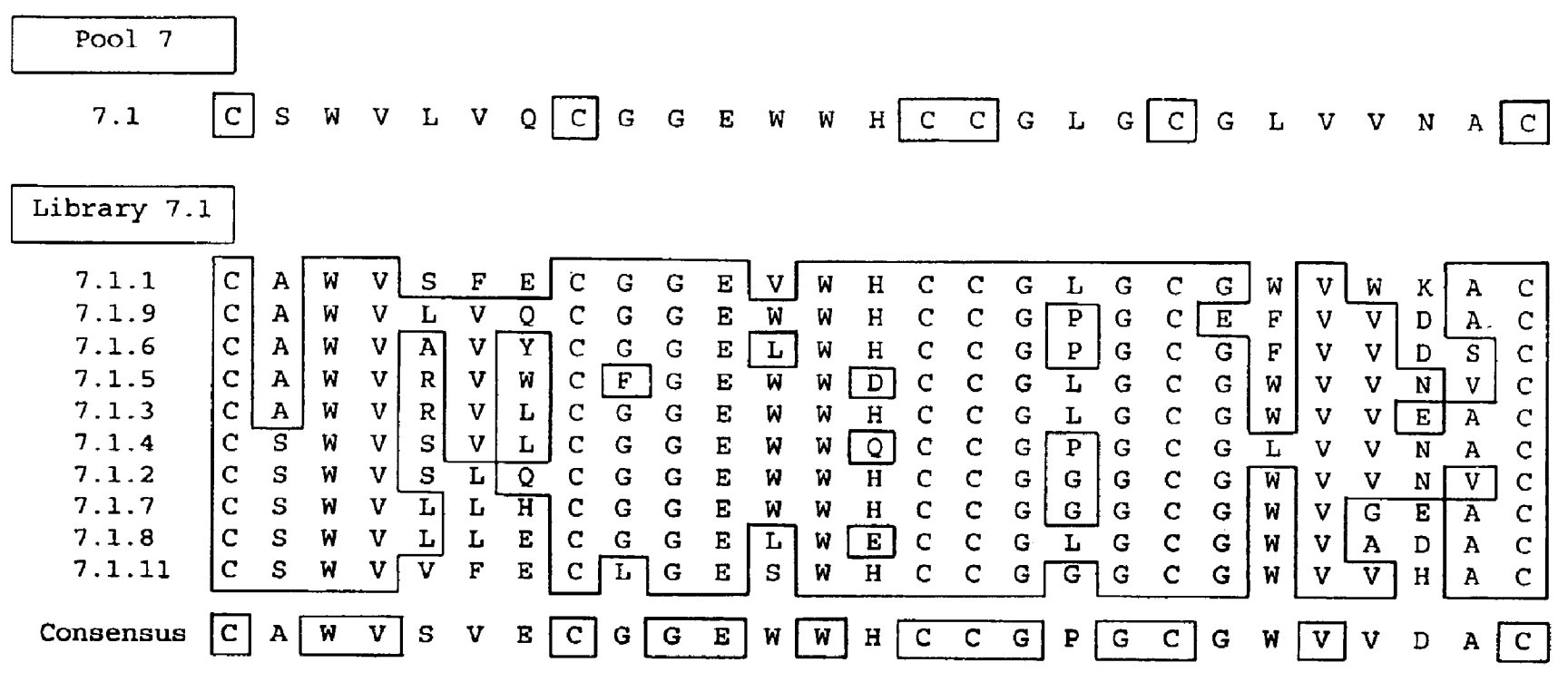

Monovalent partial randomization libraries of clones 1.1, 5.1 and 7.1 were constructed and sorted for 4 rounds on HER2. Enrichment of >10,000 fold was observed for libraries 1.1 and 7.1; however, no enrichment of library 5.1 was observed. Again, random clones were selected and sequenced; the deduced peptide sequences from clones in libraries 1.1 and 7.1 are shown in FIG. 15. Several amino acid positions in libraries 1.1 and 7.1 were 100% retained yet multiple codons were observed at many of these positions. Residues strongly retained following partial randomization may be crucial for binding either through direct contacts or for structural reasons.

Figure 16B:
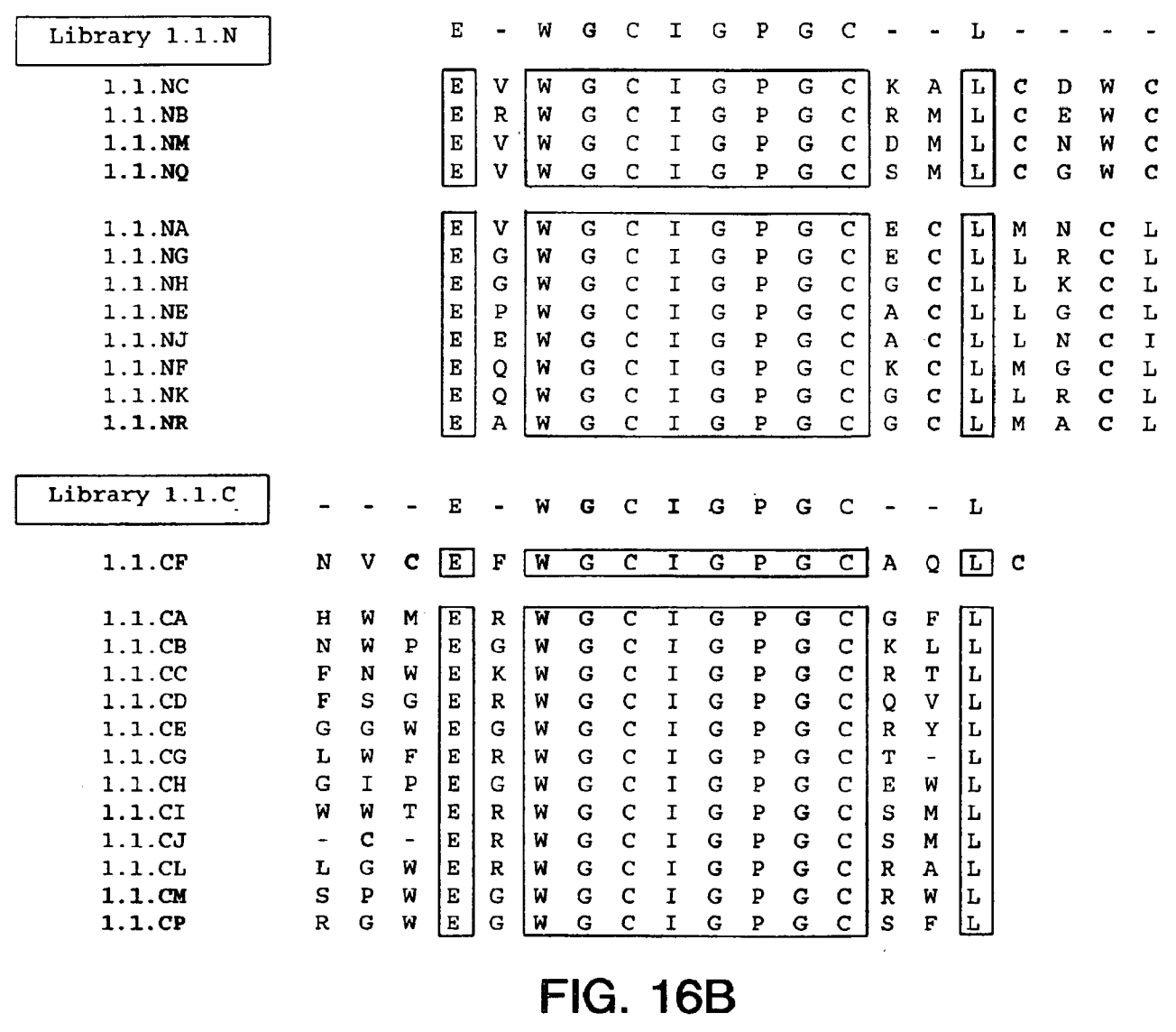

Full maturation of HER2 binding sequences—To complete the affinity maturation of the Class 1 sequences, a third set of libraries were constructed which fixed positions that had been 100% conserved and remaining positions were fully randomize. In addition, the role of residues flanking the disulfide loop of the Class 1 sequence was addressed by constructing libraries with either portions of the amino and carboxy terminal missing. Thus, 3 monovalent libraries were constructed as described in FIG. 16. Enrichment of >500-fold was observed by each library by round 4; the sequences from random clones are presented in FIG. 16. Even though these libraries which fully randomized up to 10 positions were far from complete, a comparison of the full length and amino terminal truncated libraries demonstrated a preference for an additional disulfide in the C terminal region of the Class 1 sequence. In both libraries the additional disulfide is found in 2 locations. In the third library, truncation of the C terminal positions preclude the selection of an additional disulfide at these locations. Aside from the selection of an additional disulfide, the residues selected at other randomized positions are quite diverse.

Example III

Methods

Peptide Synthesis—Peptides were synthesized by either manual or automated (Milligen 9050) Fmoc-based solid phase synthesis on a 0.25 mmol scale using a PEG-polystyrene resin (Bodanszky et al. (1984) Int. J. Peptide and Protein Res. 23(1):111). Side chain protecting groups were removed and the peptide was cleaved from the resin with 95% trifluoroacetic acid (TFA) and 5% triisopropyl-silane. A saturated iodine solution in acetic acid was added to oxidation of disulfide bonds. Peptides were purified by reversed-phase HPLC using a water/acetonitrile gradient containing 0.1% TFA. Peptides were >95% pure by analytical HPLC and its identity verified by mass spectrometry.

Production of Peptide-Z Fusions—Phage peptides selected for binding to HER2-ECD were expressed and secreted from E. coli (27C7) as fusions to the Z domain from protein A. Oligos were designed to insert the coding sequence for the phage-peptide sequences between the stII signal sequence and the Z domain in a plasmid containing the Z domain (pZCT). Cells were grown in phosphate limiting media and peptide-Z fusions were purified from the media using an IgG affinity column as described (Dennis et al., (1993) Proteins: Struct. Funct. Genentics 15:312–321). IgG affinity purified peptide Z-fusion was biotinylated using NHS-LC-biotin (Pierce) and characterized by mass spectrometry. Peptide-Z fusions which formed multimers could be separated into monomer and dimer containing fractions by size exclusion chromatography on a Superdex 75 column in PBS.

Removal of the Z domain from purified peptide-Z fusions—
Removal of the Z domain from purified peptide-Z fusions was accomplished by digestion of the fusion with trypsin. Trypsin (1%, w/w) was added for 4 hrs at 37° C. in 100 mM Tris pH 8.0 and 10 mM $CaCl_2$. The peptide, free of the Z domain was then purified on a C18 reverse-phase HPLC column using a 20 to 50% acetonitrile gradient in 0.1% TFA.

Construction of Her2-Fc expression vector—Standard recombinant DNA techniques were used for the construction of a recombinant transfer vector based on the vector pVL1393 (Pharmigen) (Sambrook, J., Fritsch, E. F., and Maniatis, T. (1989) Molecular Cloning: A Laboratory Manual, second Ed., Cold Spring Harbor Laboratory Press, New York; O'Reilly, D. R., Miller, L. K., and Luckow, V. A. (1994) Baculovirus Expression Vectors: A Laboratory Manual, Oxford University Press, New York). The pVL1393 derived plasmid pbPH.His was linearized with Nco I and Sma I and treated with shrimp alkaline phosphatase (Dwyer, M. A. et al. (1999) J. Biol. Chem. 274:9738–9743). The Fc portion of the human IgG1 was obtained as a 700 base pair fragment by restriction digestion using Nde I and subsequent treatment with Klenow and Nco I of another pVL1393 derived plasmid pVL1393.1gG. The signal sequence for MIP.5 was introduced before the Fc sequence as a PCR fragment digested with EcoR I, included within the fragment is an Asc I site. The Asc I site occurs following the putative signal sequence cleavage site. Following ligation, competent E. coli XL-1 Blue were transformed and bacteria were selected for the correct recombinant plasmid (pVL1393.MIP.5sig.Fc) by DNA sequence analysis. Then, pVL1393.MIP.5sig.Fc was linearized with Asc I and Stu I and treated with shrimp alkaline phosphatase. The linearized vector was then ligated with a synthetic piece of DNA with compatible ends. The synthetic DNA insert was formed by annealing 2 oligos with the sequences: 5'-CGC GCC CAG GTG TAC GAG TCC TGG GGA TGC ATC GGC CCC GGC TGC GCC TGC CTG CAG GCC TGC CTG GGA GGC GGG AGC TCC GGC-3' (SEQ ID NO:159) and 5'-GCC GGA GCT CCC GCC TCC CAG GCA GGC CTG CAG GCA GGC GCA GCC GGG GCC GAT GCA TCC CCA GGA CTC GTA CAC CTG GG-3' (SEQ ID NO:160) coding for peptide sequence 1.1FI including a GGGSSG (SEQ ID NO:130) linker. Following ligation, competent E. coli XL-1 Blue were transformed and bacteria were selected for the correct recombinant plasmid (termed pVL.1393.MIP5.1.1FI-Fc) by DNA sequence analysis using the dRhodamine dye-terminator method and an Applied Biosystems ABI Model 373 automated DNA sequencer. Recombinant transfer vector was purified using a Qiagen Mini-Prep and used for construction of recombinant baculovirus.

Recombinant baculovirus was generated following cotransfection of Sf9 cells with the transfer vector and the linearized wild type baculovirus DNA (Autographa californica nuclear polyhedrosis virus (AcNpV), Pharmingen). A primary amplification of the recombinant baculovirus achieved detectable protein expression. Subsequent plaque-purification and titering of the viral stock was performed by plaque assays. Standard methods were utilized as previously described (O'Reilly, D. R., Miller, L. K., and Luckow, V. A. (1994) Baculovirus Expression Vectors: A Laboratory Manual, Oxford University Press, New York).

Cell Culture—Adherent cultures of Spodeptera frugiperda (Sf9) insect cells (ATCC CRL 1711) were maintained at 28° C. in Hink's TNM-FH insect medium supplemented GRACE's (JRH Biosciences, #51942–78P), with glutamine, streptomycin/penicillin, and 10% fetal bovine serum (heat inactivated for 30 min at 56° C.). Cultures were passaged every 3 days. Spinner cultures of High 5 cells (Trichoplusia ni, BT1.TN.SB1–4 (Invitrogen)) (500 ml at $2.0 \times 10^6$ cells/ml) were infected at a multiplicity of infection of 0.5 and harvested 60 h posttransfection. Suspension cultures were maintained in spinner flasks at 28° C. using ESF-921 protein free insect cell culture medium (Expression Systems LLC, #96–001). Cultures were passaged every 3 days to a starting cell density of 106 cells/ml.

Peptide-Fc Purification—Following the optimized infection protocol, the High 5 cells were removed by centrifugation at 800×g at 4° C. for 10 min. The clarified supernatant (0.5 L) was filtered using a 0.45 $\mu$ Nalgene filter and applied to a 0.5 ml Hi-Trap Protein A Column (Amersham Pharmacia Biotech) equilibrated with PBS (phosphate buffered saline) at 25° C. After washing with 20 ml of PBS, the column was eluted with 3 ml of 0.2 N HOAc and fractions containing peptide-Fc were lyophilized and stored at 4° C.

SDS-PAGE—Samples were analyzed reduced and unreduced on a 4–20% Tris-glycine SDS-PAGE (Novex) along with prestained protein molecular weight markers (SeaBlue, Novex) using the method of Laemmli (Laemmli, U. K. (1970) Nature 227:680–685).

Protein Sequencing—1.1FI-Fc purified from the infected Sf9 cell supernatants was subjected to SDS-PAGE, and then transferred to a PVDF membrane. Electroblotting onto Millipore Immobilon-PSQ membranes was carried out for 1 h at 250 mA constant current in a BioRad Trans-Blot transfer cell (Matsudaira, P. (1987) J. Biol. Chem. 262: 10035–10038).

The PVDF membrane was stained with 0.1% Coomassie Blue R-250 in 50% methanol, 0.5 min and destained for 2–3 min with 10% acetic acid in 50% methanol. The membrane was thoroughly washed with water and allowed to dry before storage at −20° C. The 1.1FI-Fc band at about 50 kD was cut out and the first 11 residues were sequenced using a model 494A Applied Biosystems sequencer equipped with an on-line PTH analyzer. Peaks were integrated with Justice Innovation software using Nelson Analytical 760 interfaces. Sequence interpretation was performed on a DEC alpha (Henzel, W. J., Rodriguez, H., and Watanabe, C. (1987) J. Chromatog. 404: 41–52).

HER2 Competition ELISA—1.1FI-Fc binding to HER2-ECD was monitored using a competition ELISA. Samples were titered in PBS-BSA and tested for their ability to block the binding of 40 nM biotinylated 1.1.FI-Z to HER2-ECD immobilized on microtiter plates as described above. Following a 1 h incubation the plate was washed with PBS-Tween and Strepavidin/HRP conjugate (Streptavidin-POD, Roche Molecular Biochemicals) was added for 30 min. Plates were washed again with PBS-Tween and the bound HRP was assayed using ABTS/$H_2O_2$ substrate (Kirkegaard & Perry Laboratories) and the absorbance at 405 nm was monitored. The absorbance at 405 nm was plotted versus the concentration of 1.1FI-Fc originally added to the well. Sigmoidal curves were fit to a four parameter equation by nonlinear regression analysis (Marquardt, J. Soc. Indust. Appl. Math. 11:431–441 (1963); the concentration of 1.1FI-Fc required to give a half-maximal signal in the assay was calculated from the curves and is referred to as the $IC_{50}$ value.

Cell binding—Cells expressing HER2 (BT 474 [3+], MDA 361 [2+], and BaF3 [0+]) were detached with trypsin, washed twice with Wash Buffer (PBS containing 0.5% BSA, 1 mM NaOH), and split into fractions containing $0.5 \times 10^6$ cells each. The cells were suspended in Wash Buffer containing 0, 0.5 or 5 $\mu$M 1.1.FI-Zb, washed twice with Wash Buffer and suspended in Wash Buffer containing strepavidin-PE, washed twice with Wash Buffer and subjected to FACS analysis.

Results

Characterization of Peptides that bind to HER2-ECD—Peptide HER201 was synthesized corresponding to partially randomized phage-clone 1.1.2 (FIG. 15). In addition, peptide HER212 corresponding to a representative clone 1.1.FI (FIG. 16) derived from the fully randomized full length library was also synthesized. Due to the presence of 2 disulfides in this peptide, orthogonal protecting groups were used for the cysteines in order to induce a 1–2 and 3–4 disulfide arrangement. This arrangement was suspected because of the order in which the disulfide bonds evolved during the selection process.

Figure 6:
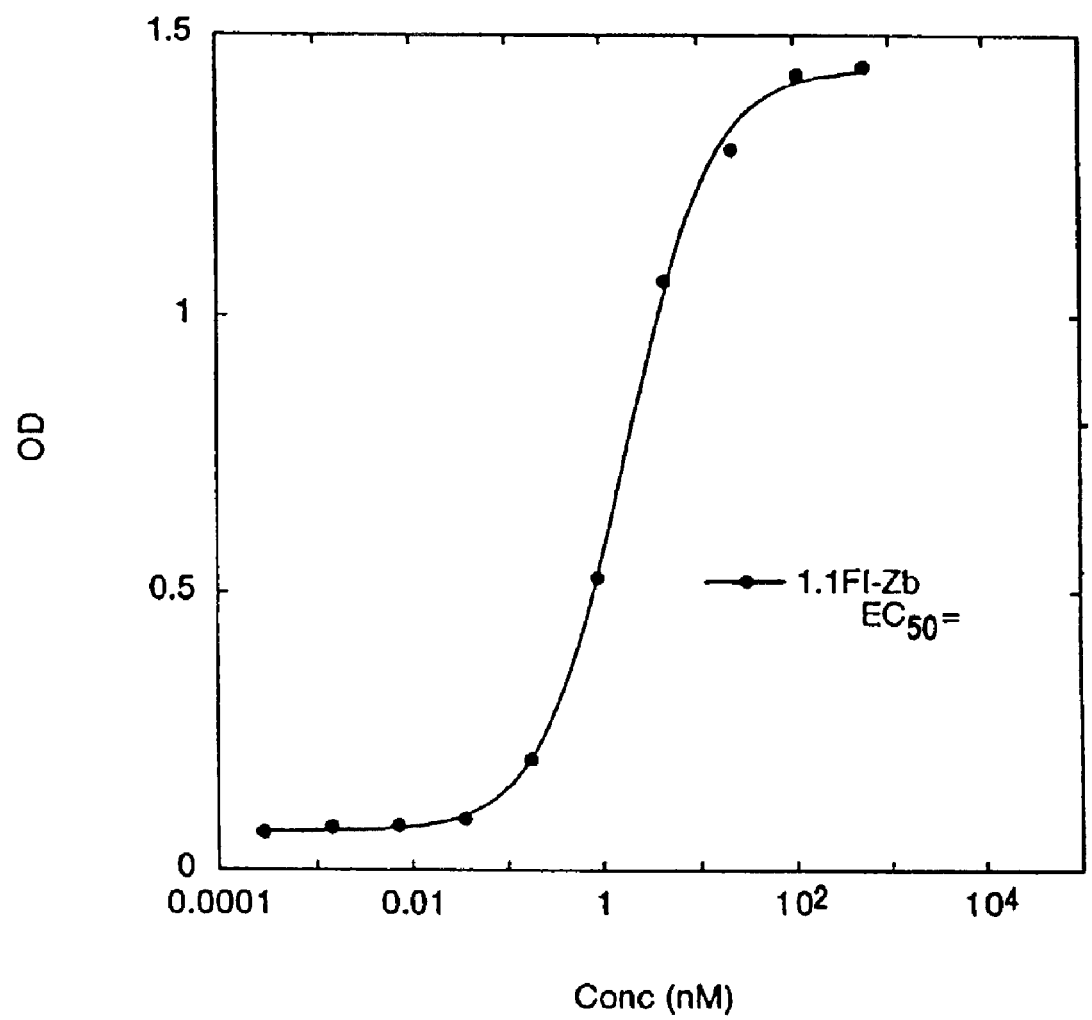
FIG. 6 shows EC50 determination for peptide 1.1.FIZb binding immobilized HER2.

Additionally, this peptide and a peptide sequence derived from the consensus of library 7.1 (FIG. 15) (7.1c) were expressed and secreted from *E. coli* as a fusion to the Z domain of protein A (called 1.1.FI-Z and 7.1c-Z) where cysteine oxidation might be allowed to occur as it does during phage production. The 1.1.FI-Z preparation was biotinylated (1.1.FI-Zb) and bound to immobilized HER2 with an EC50 of 2 nM based on the total protein concentration (FIG. 6) and served as a reagent for the competition ELISA.

Figure 7:
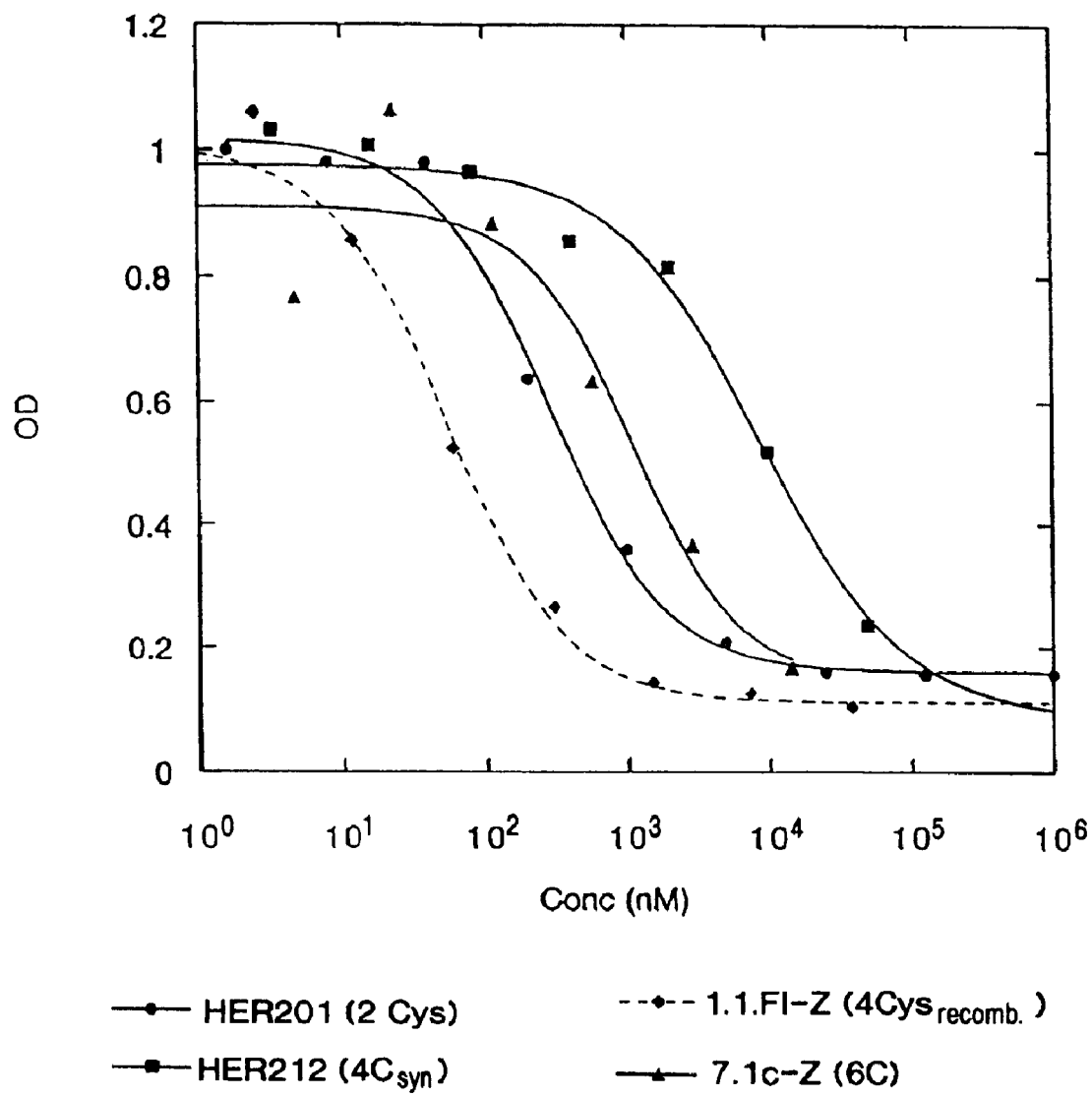
FIG. 7 shows the results of a competition assay for synthetic peptides HER201 and HER212 as well as recombinant peptides 1.1.FI-Z and 7.1c-Z with peptide 1.1.FI-Zb for binding to immobilized HER2-ECD.

Peptides HER201, HER212 as well as the recombinant peptide fusions 1.1.FI-Z and 7.1c-Z were tested for the ability to block binding of 1.1.FI-Zb to immobilized HER2 (FIG. 7). HER201 and 7.1c-Z had IC50s of 300 and 1,100 nM respectively. Interestingly, HER212 and 1.1.FI-Z, which were derived from the same phage-peptide sequence had dramatically different IC50s: 9 $\mu$M and 50 nM respectively. One explanation could be that another disulfide arrangement was forced in the synthesis of HER212. Additionally, SDS-PAGE analysis of 1.1.FI-Z (FIG. 8B)(lane S) revealed a heterogeneous mixture likely due to multimerization caused by intermolecular disulfides. Mass spectral analysis confirmed presence of dimer 1.1.FI-Z while HER212 was present only as monomer.

Figure 8A:
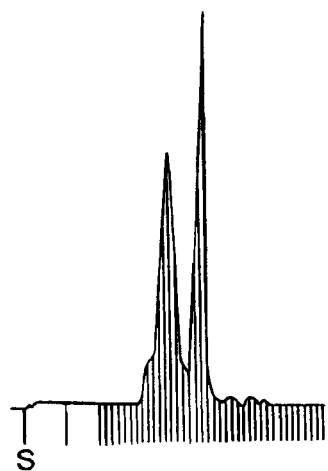
FIGS. 8A–C.
Figure 8B:
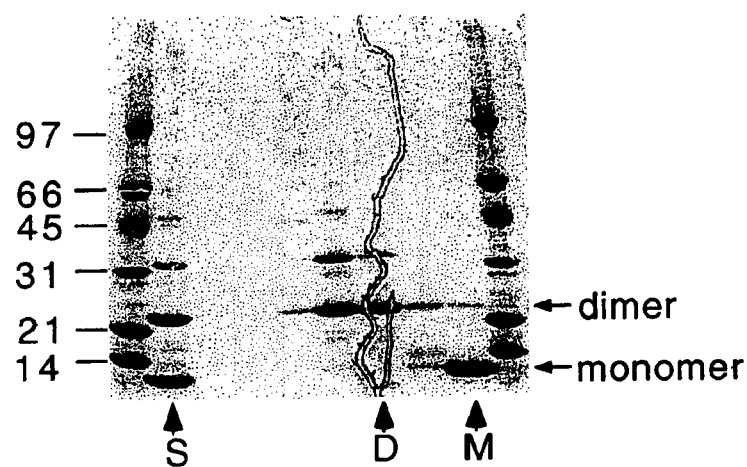
Figure 8C:
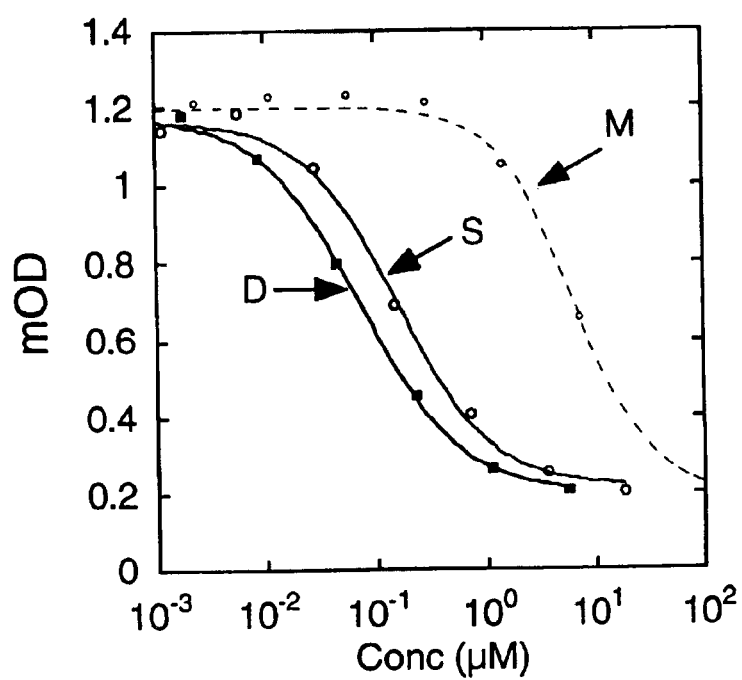

The 1.1.FI-Z preparation was further purified using a Superdex 75 into monomer and dimer containing fractions (FIGS. 8A and 8B). Surprisingly, HER2 binding activity coincided with the dimer fractions rather than the monomer fractions (FIGS. 8B and 8C) when assayed in the HER2 competition ELISA.

In addition, 1.1.FI-Z was digested with trypsin to removed the Z domain and subjected to reversed phase HPLC. Fractions from the HPLC were tested for their ability to compete in the HER2 competition ELISA. The active fraction had a mass corresponding to the sequence of HER212 but was also found to contain dimer. This fraction had an IC50 of 3 nM in the HER2 competition ELISA based on protein concentration.

In an attempt to facilitate dimer formation, an expression vector was constructed in which the amino acid sequence of 1.1.FI was repeated twice prior to fusion with Z domain (FIG. 9). While this "single chain dimer" (called $(FI)_2$-Z), also produced dimer when expressed, the dominate species formed was monomer (FIG. 9B). In addition, when fractionated on a Superdex 75 column (FIG. 9A) and assayed in the HER2 competition ELISA, the active species was now identified as monomer (FIGS. 9B and C). $(FI)_2$-Z has a similar affinity for HER2 as the 1.1.FI-Z dimer (IC50=20 nM).

Figure 10A:
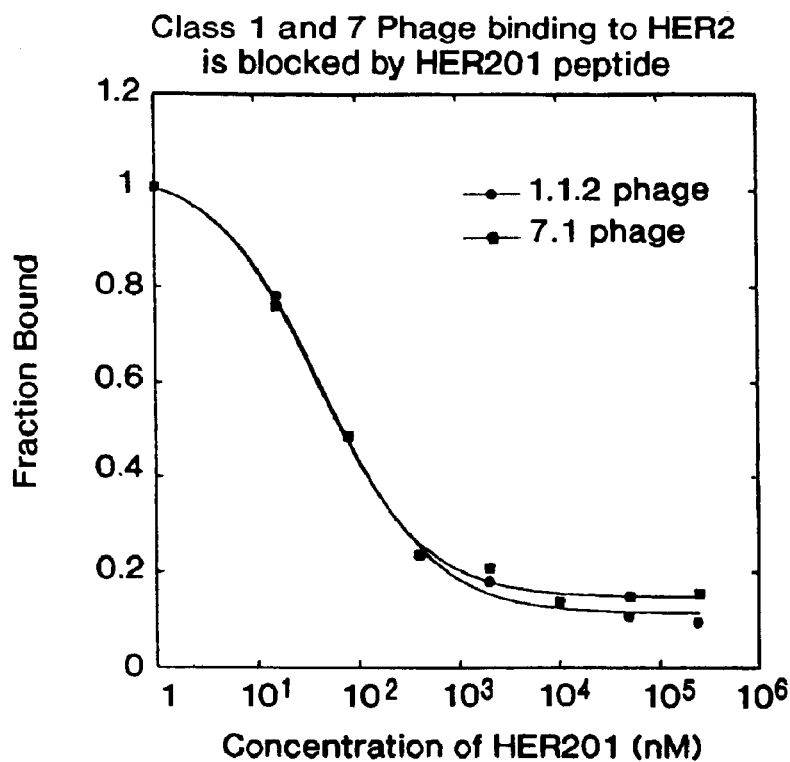
FIGS. 10A and B.
Figure 10B:
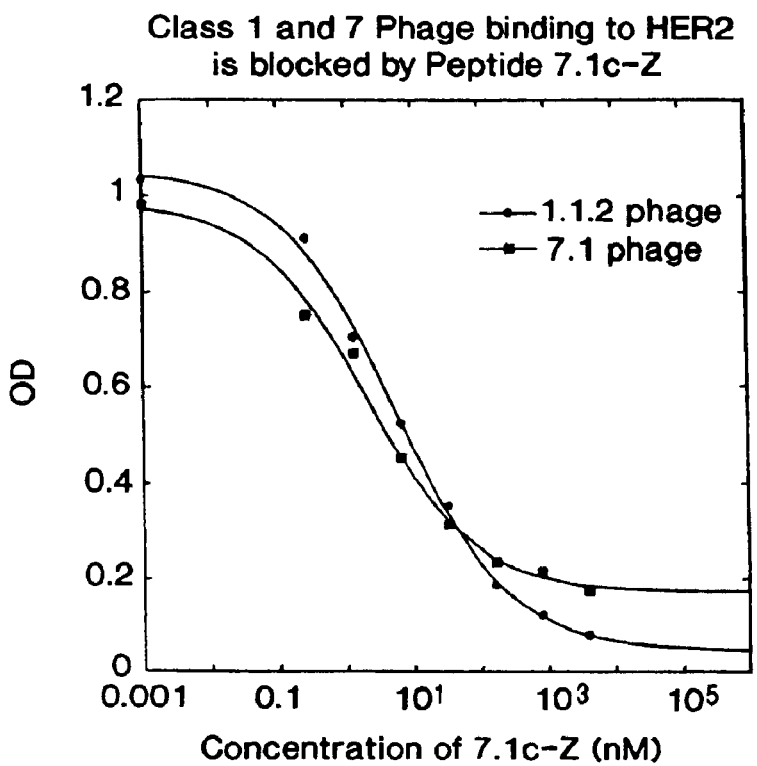
Figure 11:
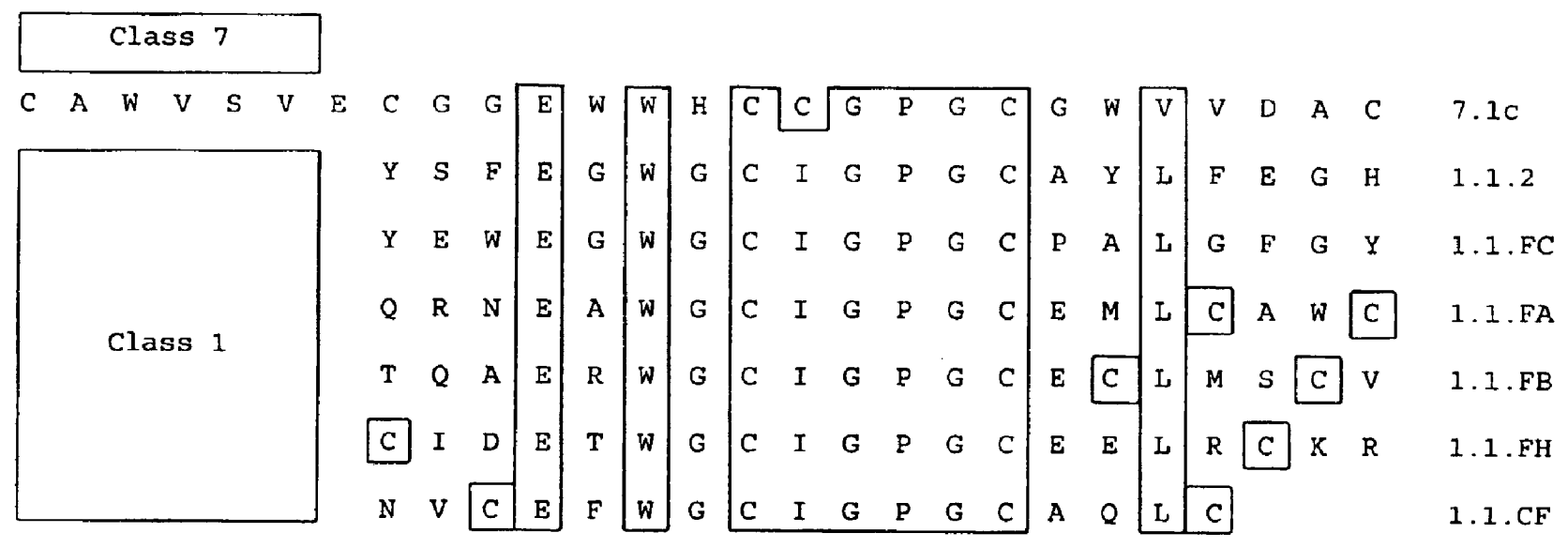

Binding Site on HER2—To test whether Class 1 and Class 7 sequences bound to the same or independent sites on HER2, the binding of phage clones from Class 1 and Class 7 libraries to immobilized HER2 was examined in the presence of HER201 or 7.1c-Z. From FIGS. 10A and 10B, it is apparent that HER201 and 7.1c-Z block the binding of both Class 1 and Class 7 phage suggesting that both Classes bind to the same site on HER2. A closer look at the sequences obtained in these 2 classes reveals a core homology region (FIG. 11).

Figure 12:
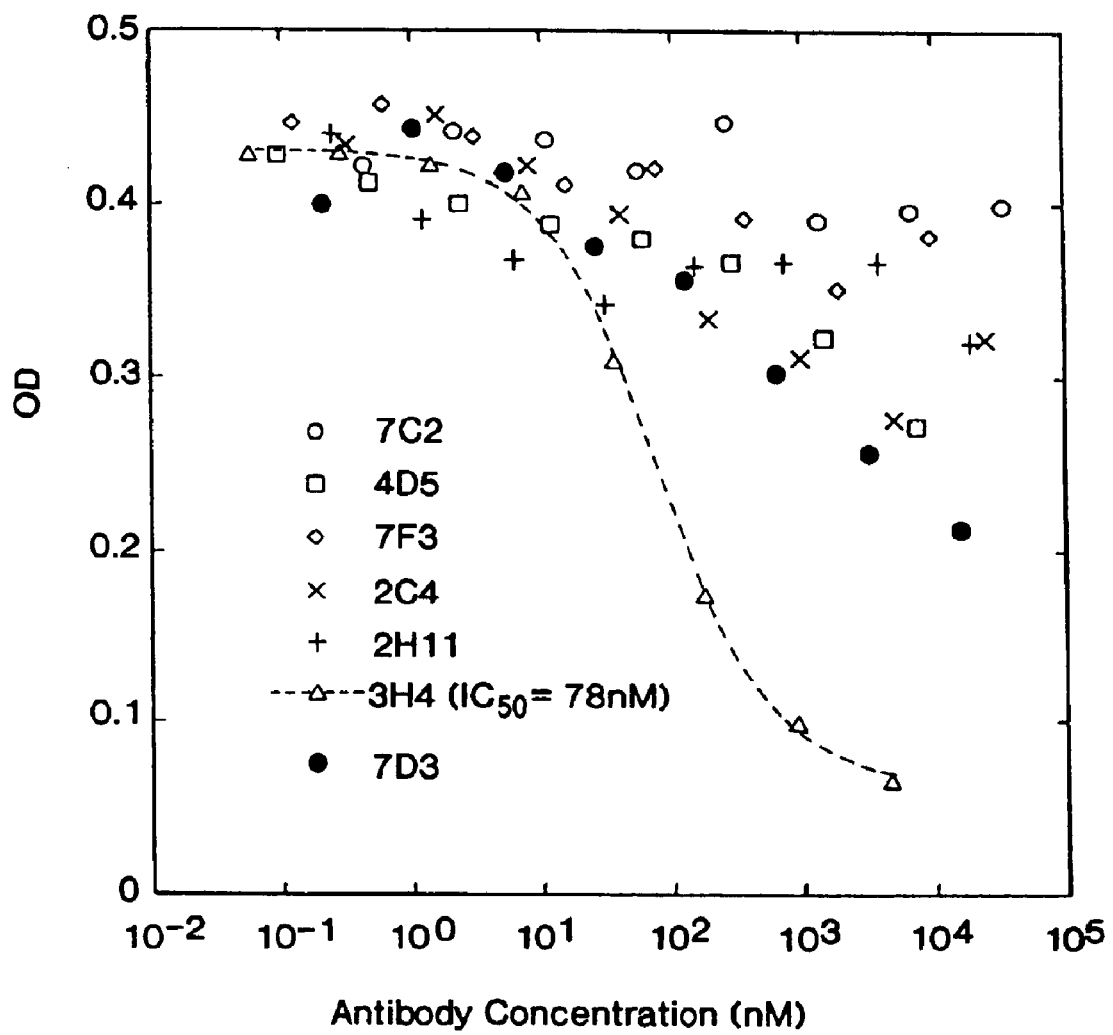
FIG. 12 shows the results of a competition assay of Class 1 and Class 7 peptides with known monoclonal antibodies directed against HER2 for binding HER2-ECD. The peptides do not compete with the monoclonal antibodies for binding HER2-ECD suggesting that the peptides bind a HER2-ECD site distinct from that recognized by known monoclonal antibodies.

The binding site of the Class 1 and Class 7 peptides also appears to be a novel site on HER2 in that known monoclonal antibodies to HER2 did not directly compete with 1.1.FI-phage binding to immobilized HER2 (FIG. 12). Increasing concentrations of various monoclonal antibodies were added to block 1.1.FI-phage binding to immobilized HER2 without effect. The reduction in binding at very high concentrations of 3H4 (>100 nM) are thought to result through an indirect effect since the affinity of this monoclonal antibody for HER2 is below 100 pM.

Figure 13:
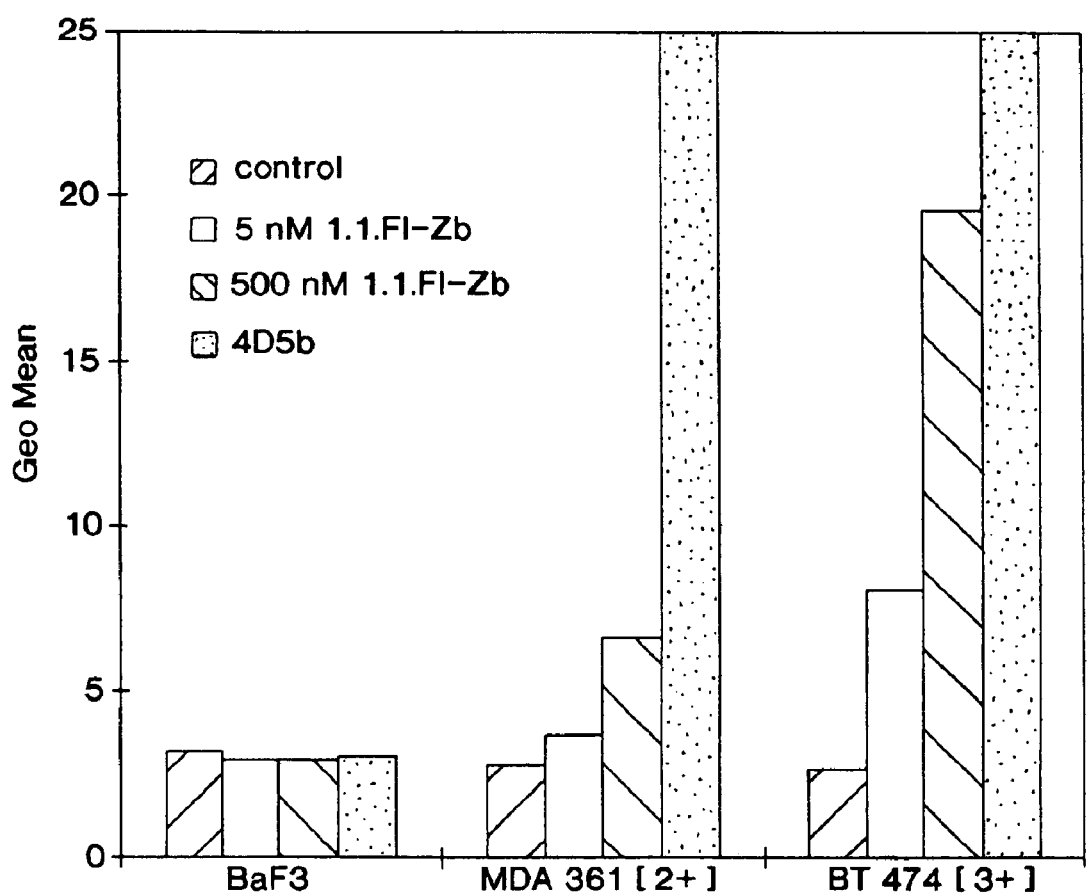
FIG. 13 shows the results of a binding assay conducted using peptide 1.1.FI-Zb and cells either expressing HER2 at different levels (MDA 361 [$4 \times 10^5$ receptors/cell]) and BT 474 ([$3 \times 10^6$ receptors/cell]) or cells not expressing HER2 (BaF3). 1.1.FI-Zb was found to bind cells proportional to the number of HER2 receptors expressed on the cell and concentration of 1.1.FI-Zb peptide.

Cell Binding—1.1.FI-Zb was tested for its ability to recognize HER2 expressed on cells. Three cell types which expressed HER2 at different levels were examined: BT 474 [3+] ($3 \times 10^6$ receptors/cell), MDA 361 [2+] ($4 \times 10^5$ receptors/cell), and a control cell line that doesn't express HER2, BaF3. By FACS analysis, 1.1.FI-Zb was found to bind to cells proportional to the number of HER2 of receptors expressed/cell and the concentration of 1.1.FI-Zb used (FIG. 13).

Figure 14:
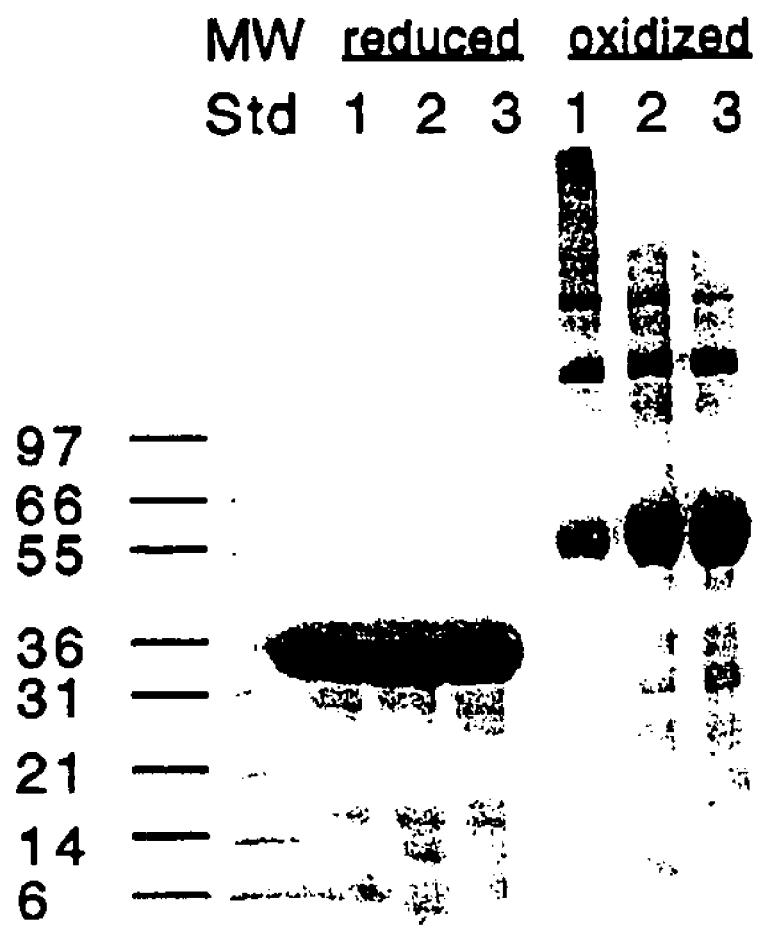
FIG. 14 shows the results of SDS PAGE analysis under oxidizing and reducing conditions of peptide 1.1.FI fused through a linker to the hinge, CH1 and CH2 domains of human IgG1 (1.1FI-Fc). The molecular weight shift under the two conditions suggests dimerization of the Ig constant regions and the formation of a Fc domain.
Figure 17:
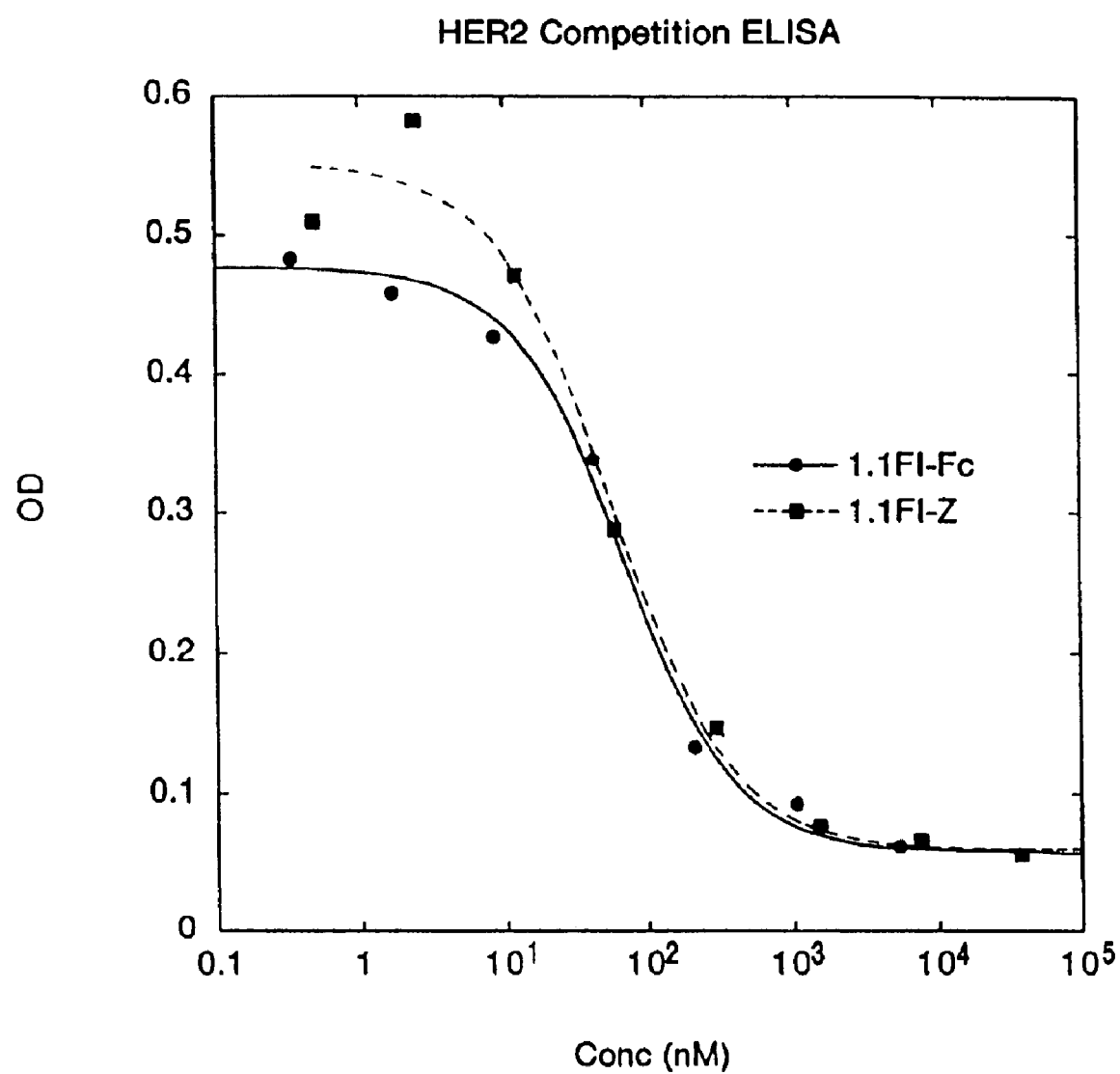
FIG. 17 shows the results of a competition assay of 1.1FI-Fc and 1.1FI-Z with peptide 1.1FI-Zb for binding to immobilized HER2-ECD.

Peptide-Fc fusions—DNA coding for the 1.1.FI sequence was fused through a linker to an Fc from a $IgG_1$ and expressed in bacolovirus. The resulting protein was purified on a Protein A column and characterized under oxidizing and reducing conditions by SDS-PAGE (FIG. 14). A clear molecular weight shift is observed under these 2 conditions suggesting dimerization of the Fc. This molecule, when tested for its ability to block 1.1FI phage binding to immobilized HER2, has an IC50 of 3 nM. When tested in the HER2 competition ELEISA, 1.1FI-Fc had a similar IC50 to 1.1FI-Z indicating that the 1.1FI sequence was fully capable of binding HER2 when fused to an Fc (FIG. 17).

What is claimed is:

1. An isolated peptide ligand that binds HER2 in an in vitro assay, the peptide ligand consisting of an amino acid sequence: $Xaa_{(1-14)}$-Cys-$Xaa_{16}$-Gly-Pro-Gly-Cys-$Xaa_{(21-27)}$ (SEQ ID NO: 90), wherein: $Xaa_{(1-14)}$ is absent or between one and fourteen amino acids; $Xaa_{16}$ is an amino acid selected from the group consisting of Met, Thr, Cys, and Ile; and $Xaa_{(21-27)}$ is absent or between one and seven amino acids.

2. The peptide ligand of claim 1, wherein the amino acid sequence consists of: $Xaa_{(1-7)}$-Cys-$Xaa_9$-Gly-Cys-$Xaa_{(14-20)}$ (SEQ ID NO:92), wherein $Xaa_{(1-7)}$ is absent or between one and seven amino acids; and $Xaa_9$ is an amino acid selected from the group consisting of Met, Ile, Thy, or Cys; and $Xaa_{(14-20)}$ is absent or between one and seven amino acids.

3. The peptide ligand of claim 2, wherein the amino acid sequence consists of: $Xaa_{(1-7)}$-Cys-Ile-Gly-Pro-Gly-Pro-Gyl-Cys-$Xaa_{(14-20)}$ (SEQ ID NO:161).

4. A peptide ligand comprising an amino acid sequence: AZA, wherein A is the peptide ligand of claim 3 and is an optional linker domain.

5. A polypeptide comprising:
  (a) a peptide ligand according to claim 1 or 4; and
  (b) an immunoglobulin constant region sequence.

6. The polypeptide of claim 5, further comprising a linker sequence connected to the peptide ligand and the immunogloblin constant region sequence.

7. The polypeptide of claim 5, wherein the immunoglobulin constant region sequence is the constant domain of an IgG heavy chain.

8. The polypeptide of claim 7, wherein said constant region sequence comprises the CH3 domain of an immunoglobulin heavy chain.

9. The polypeptide of claim 8, further comprising the hinge region of an immunoglobulin heavy chain.

10. The polypeptide of claim 9, wherein said constant region sequence comprises at least functionally active hinge, CH2, and CH3 domains of the constant region of an immunoglobulin heavy chain.

11. The polypeptide of claim 5, further comprising an additional functional moiety.

12. The polypeptide of claim 11, wherein the additional functional moiety is selected from the group consisting of a cytotoxic agent and an enzyme.

13. A pharmaceutical composition comprising the polypeptide of claim 12 and a pharmaceutically acceptable excipient.

14. The polypeptide of claim 11, wherein the additional functional moiety is a cytotoxic agent.

15. An isolated peptide ligand that binds HER2 in an in vitro assay, the peptide ligand having an amino acid sequence comprising the formula: $Xaa_{(1-5)}$-Trp-$Xaa_7$-Cys-Ile-Gly-Pro-Gly-Cys-$Xaa_{(14-20)}$ (SEQ ID NO:93), wherein: $Xaa_{(1-5)}$ is absent or between one and five amino acids, $Xaa_7$ is Gly, and wherein $Xaa_{(14-20)}$ is absent or between one and seven amino acids.

16. The peptide ligand of claim 15 consisting of an amino acid sequence: $Xaa_{(1-3)}$-Glu-$Xaa_5$-Trp-Gly-Cys-Ile-Gly-Pro-Gly-Cys-$Xaa_{14}$-$Xaa_{15}$-Leu-$Xaa_{(17-20)}$ (SEQ ID NO:91), wherein:

$Xaa_{(1-3)}$ is absent or between one and three amino acids;

$Xaa_5$ is an amino acid;

$Xaa_{14}$ is an amino acid;

$Xaa_{15}$ is an amino acid; and

-$Xaa_{(17-20)}$ is absent or between one and four amino acids.

17. The peptide ligand of claim 16, wherein: $Xaa_{(1-3)}$- is absent or selected ftom the group consisting of:

Gln-Arg-Asn-,

Leu-Ser-Pro-,

Glu-Asn-Trp-,

Ala-Ser-His-,

Lys-Leu-Asn-,

Thr-Gln-Ala-,

Ala-Pro-Arg-,

Gln-Val-Tyr-,

Arg-Thr-Glu-,

Phe-Ala-Gly-,

Thr-Ala-Arg-,

Arg-Pro-His-,

Asn-Val-Cys-,

Cys-Ile Asp-,

Tyr-Glu-Trp-,

Arg-Trp-Asp-,

His-Trp-Met-,

Asn-Trp-Pro-,

Phe-Asn-Trp-,

Phe-Ser-Gly-,

Gly-Gly-Trp-,

Leu-Trp-Phe-,

Gly-Ile-Pro-,

Trp-Trp-Thr-,

Leu-Gly-Trp-,

Ser-Pro-Trp-,

Arg-Gly-Trp-;

$Xaa_5$ is selected from the group consisting of: Ala, Thr, Met, Val, Arg, Glu, Asp, Ser, Gln, Pro, Gly, Phe; and Lys;

$Xaa_{14}$ is selected from the group consisting of: Gln, Lys, Arg, Asp, Ser, Ala, Asn, Gly, Pro, and Gln;

$Xaa_{15}$ is selected from the group consisting of: Met, Phe, Ala, Met, Cys, Gln, Glu, Ala, Trp, Phe, Leu, Val, Tyr, and Trp; and -$Xaa_{(17-20)}$ is a four amino acid peptide having the following formula: -$Xaa_{17}$-$Xaa_{18}$-Cys-$Xaa_{20}$.

18. The peptide ligand of claim 17, wherein: -$Xaa_{(17-20)}$ is selected from the group consisting of:

-Gln-Ala-Cys-Met (SEQ ID NO:102),

-Leu-Gln-Cys-Trp (SEQ ID NO:103),

-Met-Ser-Cys-Val (SEQ ID NO:104),

-Leu-Arg-Cys-Ile (SEQ ID NO:105),

-Gln-Ala-Cys-Leu (SEQ ID NO:106),

-Leu-Ser-Cys-Leu (SEQ ID NO:107),

-Ile-Gly-Cys-Leu (SEQ ID NO:108),

-Leu-Ala-Cys-Leu (SEQ ID NO:109),

-Leu-Ser-Cys-Ile (SEQ ID NO:110),

-Met-Asn-Cys-Leu (SEQ ID NO:111),

-Leu-Arg-Cys-Leu (SEQ ID NO:112),

-Leu-Lys-Cys-Leu (SEQ ID NO:113),

-Leu-Gly-Cys-Leu (SEQ ID NO:114),

-Leu-Asn-Cys-Ile (SEQ ID NO:115),

-Met-Gly-Cys-Leu (SEQ ID NO:116), and

-Met-Ala-Cys-Leu (SEQ ID NO:117).

19. A pharmaceutical composition comprising the peptide ligand of claim 1 and pharmaceutically acceptable excipient.

20. A pharmaceutical composition comprising the polypeptide of claim 5 and a pharmaceutically acceptable excipient.

21. An isolated DNA molecule encoding the peptide ligand of claim 1.

22. The DNA molecule of claim 21, further comprising an expression control sequence operably linked to the DNA molecule.

23. An expression vector comprising the DNA molecule of claim 22, wherein the control sequence is recognized by a host cell transformed with the vector.

24. A host cell transformed with the vector of claim 23.

25. A method for expressing a DNA molecule encoding a peptide ligand in a host cell, comprising culturing the host cell of claim 24 under conditions suitable for expression of the peptide ligand.

26. The method of claim 25, further comprising recovering the peptide ligand from the culture medium.

* * * * *

UNITED STATES PATENT AND TRADEMARK OFFICE
CERTIFICATE OF CORRECTION

PATENT NO. : 6,987,088 B2
DATED : January 17, 2006
INVENTOR(S) : Mark S. Dennis

It is certified that error appears in the above-identified patent and that said Letters Patent is hereby corrected as shown below:

Title page,
Item [56], References Cited, OTHER PUBLICATIONS, "Seq IG No.: 15 (sequence search results only)." should be -- Seq ID No. 15 from US 5,279,966 by Jessell et al. (sequence search results only). --.
"Seq IG No.: 8 (sequence search results only)." should be -- Seq ID No. 8 from US 5,871,969 by Hastings et al. (sequence search results only). --.

Column 113,
Line 58, after "Gly-" and before "-Cys", insert -- Pro-Gly --;
Line 60, replace "Thy" with -- Thr --;
Lines 63 and 64, "$Xaa_{(1-7)}$-Cys-Ile-Gly-Pro-Gly-Pro-Gyl-Cys-$Xaa_{(1-7)}$" should be -- $Xaa_{(1-7)}$-Cys -Ile-Gly-Pro-Gly-Cys-$Xaa_{(1-7)}$ --.
Line 66, after "and" and before "is" insert -- Z --.

Column 114,
Line 53, after "sequence" and before "connects" insert -- operably --.

Column 115,
Line 7, replace "Gln, Lys" with -- Glu, Lys --.

Signed and Sealed this

Thirtieth Day of May, 2006

JON W. DUDAS
*Director of the United States Patent and Trademark Office*

SEQUENCE LISTING

```
<160> NUMBER OF SEQ ID NOS: 162

<210> SEQ ID NO 1
<211> LENGTH: 20
<212> TYPE: PRT
<213> ORGANISM: Artificial Sequence
<220> FEATURE:
<223> OTHER INFORMATION: synthetic peptide sequence

<400> SEQUENCE: 1

Gln Arg Asn Glu Ala Trp Gly Cys Ile Gly Pro Gly Cys Glu Met
 1               5                  10                  15

Leu Cys Ala Trp Cys
            20

<210> SEQ ID NO 2
<211> LENGTH: 20
<212> TYPE: PRT
<213> ORGANISM: Artificial Sequence
<220> FEATURE:
<223> OTHER INFORMATION: synthetic peptide sequence

<400> SEQUENCE: 2

Leu Ser Pro Glu Thr Trp Gly Cys Ile Gly Pro Gly Cys Glu Met
 1               5                  10                  15

Leu Cys Ser Trp Cys
            20

<210> SEQ ID NO 3
<211> LENGTH: 20
<212> TYPE: PRT
<213> ORGANISM: Artificial Sequence
<220> FEATURE:
<223> OTHER INFORMATION: synthetic peptide sequence

<400> SEQUENCE: 3

Glu Asn Trp Glu Met Trp Gly Cys Ile Gly Pro Gly Cys Lys Phe
 1               5                  10                  15

Leu Cys Glu Pro Cys
            20

<210> SEQ ID NO 4
<211> LENGTH: 17
<212> TYPE: PRT
<213> ORGANISM: Artificial Sequence
<220> FEATURE:
<223> OTHER INFORMATION: synthetic peptide sequence

<400> SEQUENCE: 4

Glu Val Trp Gly Cys Ile Gly Pro Gly Cys Lys Ala Leu Cys Asp
 1               5                  10                  15

Trp Cys

<210> SEQ ID NO 5
<211> LENGTH: 17
<212> TYPE: PRT
<213> ORGANISM: Artificial Sequence
```

-continued

```
<220> FEATURE:
<223> OTHER INFORMATION: synthetic peptide sequence

<400> SEQUENCE: 5

Glu Arg Trp Gly Cys Ile Gly Pro Gly Cys Arg Met Leu Cys Glu
 1               5                  10                  15

Trp Cys

<210> SEQ ID NO 6
<211> LENGTH: 17
<212> TYPE: PRT
<213> ORGANISM: Artificial Sequence
<220> FEATURE:
<223> OTHER INFORMATION: synthetic peptide sequence

<400> SEQUENCE: 6

Glu Val Trp Gly Cys Ile Gly Pro Gly Cys Asp Met Leu Cys Asn
 1               5                  10                  15

Trp Cys

<210> SEQ ID NO 7
<211> LENGTH: 17
<212> TYPE: PRT
<213> ORGANISM: Artificial Sequence
<220> FEATURE:
<223> OTHER INFORMATION: synthetic peptide sequence

<400> SEQUENCE: 7

Glu Val Trp Gly Cys Ile Gly Pro Gly Cys Ser Met Leu Cys Gly
 1               5                  10                  15

Trp Cys

<210> SEQ ID NO 8
<211> LENGTH: 20
<212> TYPE: PRT
<213> ORGANISM: Artificial Sequence
<220> FEATURE:
<223> OTHER INFORMATION: synthetic peptide sequence
<220> FEATURE:
<221> NAME/KEY: unsure
<222> LOCATION: 1-3, 5, 14, 18
<223> OTHER INFORMATION: unknown amino acid

<400> SEQUENCE: 8

Xaa Xaa Xaa Glu Xaa Trp Gly Cys Ile Gly Pro Gly Cys Xaa Met
 1               5                  10                  15

Leu Cys Xaa Trp Cys
            20

<210> SEQ ID NO 9
<211> LENGTH: 20
<212> TYPE: PRT
<213> ORGANISM: Artificial Sequence
<220> FEATURE:
<223> OTHER INFORMATION: synthetic peptide sequence

<400> SEQUENCE: 9

Ala Ser His Glu Val Trp Gly Cys Ile Gly Pro Gly Cys Lys Cys
 1               5                  10                  15

Leu Gln Ala Cys Met
            20

<210> SEQ ID NO 10
<211> LENGTH: 20
```

```
<212> TYPE: PRT
<213> ORGANISM: Artificial Sequence
<220> FEATURE:
<223> OTHER INFORMATION: synthetic peptide sequence

<400> SEQUENCE: 10

Lys Leu Asn Glu Glu Trp Gly Cys Ile Gly Pro Gly Cys Ala Cys
 1               5                  10                  15

Leu Leu Gln Cys Trp
                20

<210> SEQ ID NO 11
<211> LENGTH: 20
<212> TYPE: PRT
<213> ORGANISM: Artificial Sequence
<220> FEATURE:
<223> OTHER INFORMATION: synthetic peptide sequence
<220> FEATURE:
<221> NAME/KEY: unsure
<222> LOCATION: 18, 20
<223> OTHER INFORMATION: unknown amino acid

<400> SEQUENCE: 11

Lys Leu Asn Glu Asp Trp Gly Cys Ile Gly Pro Gly Cys Ala Cys
 1               5                  10                  15

Leu Leu Xaa Cys Xaa
                20

<210> SEQ ID NO 12
<211> LENGTH: 20
<212> TYPE: PRT
<213> ORGANISM: Artificial Sequence
<220> FEATURE:
<223> OTHER INFORMATION: synthetic peptide sequence

<400> SEQUENCE: 12

Thr Gln Ala Glu Arg Trp Gly Cys Ile Gly Pro Gly Cys Glu Cys
 1               5                  10                  15

Leu Met Ser Cys Val
                20

<210> SEQ ID NO 13
<211> LENGTH: 20
<212> TYPE: PRT
<213> ORGANISM: Artificial Sequence
<220> FEATURE:
<223> OTHER INFORMATION: synthetic peptide sequence

<400> SEQUENCE: 13

Ala Pro Arg Glu Val Trp Gly Cys Ile Gly Pro Gly Cys Ala Cys
 1               5                  10                  15

Leu Leu Arg Cys Ile
                20

<210> SEQ ID NO 14
<211> LENGTH: 20
<212> TYPE: PRT
<213> ORGANISM: Artificial Sequence
<220> FEATURE:
<223> OTHER INFORMATION: synthetic peptide sequence

<400> SEQUENCE: 14

Gln Val Tyr Glu Ser Trp Gly Cys Ile Gly Pro Gly Cys Ala Cys
 1               5                  10                  15

Leu Gln Ala Cys Leu
```

<210> SEQ ID NO 15
<211> LENGTH: 20
<212> TYPE: PRT
<213> ORGANISM: Artificial Sequence
<220> FEATURE:
<223> OTHER INFORMATION: synthetic peptide sequence

<400> SEQUENCE: 15

Arg Thr Glu Glu Gln Trp Gly Cys Ile Gly Pro Gly Cys Arg Cys
 1               5                  10                  15

Leu Leu Ser Cys Leu
                20

<210> SEQ ID NO 16
<211> LENGTH: 20
<212> TYPE: PRT
<213> ORGANISM: Artificial Sequence
<220> FEATURE:
<223> OTHER INFORMATION: synthetic peptide sequence

<400> SEQUENCE: 16

Phe Ala Gly Glu Ser Trp Gly Cys Ile Gly Pro Gly Cys Glu Cys
 1               5                  10                  15

Leu Ile Gly Cys Leu
                20

<210> SEQ ID NO 17
<211> LENGTH: 20
<212> TYPE: PRT
<213> ORGANISM: Artificial Sequence
<220> FEATURE:
<223> OTHER INFORMATION: synthetic peptide sequence

<400> SEQUENCE: 17

Thr Ala Arg Glu Val Trp Gly Cys Ile Gly Pro Gly Cys Asn Cys
 1               5                  10                  15

Leu Leu Ala Cys Leu
                20

<210> SEQ ID NO 18
<211> LENGTH: 20
<212> TYPE: PRT
<213> ORGANISM: Artificial Sequence
<220> FEATURE:
<223> OTHER INFORMATION: synthetic peptide sequence

<400> SEQUENCE: 18

Arg Pro His Glu Pro Trp Gly Cys Ile Gly Pro Gly Cys Ser Cys
 1               5                  10                  15

Leu Leu Ser Cys Ile
                20

<210> SEQ ID NO 19
<211> LENGTH: 17
<212> TYPE: PRT
<213> ORGANISM: Artificial Sequence
<220> FEATURE:
<223> OTHER INFORMATION: synthetic peptide sequence

<400> SEQUENCE: 19

Glu Val Trp Gly Cys Ile Gly Pro Gly Cys Glu Cys Leu Met Asn
 1               5                  10                  15

Cys Leu

<210> SEQ ID NO 20
<211> LENGTH: 17
<212> TYPE: PRT
<213> ORGANISM: Artificial Sequence
<220> FEATURE:
<223> OTHER INFORMATION: synthetic peptide sequence

<400> SEQUENCE: 20

Glu Gly Trp Gly Cys Ile Gly Pro Gly Cys Glu Cys Leu Leu Arg
 1               5                  10                  15

Cys Leu

<210> SEQ ID NO 21
<211> LENGTH: 17
<212> TYPE: PRT
<213> ORGANISM: Artificial Sequence
<220> FEATURE:
<223> OTHER INFORMATION: synthetic peptide sequence

<400> SEQUENCE: 21

Glu Gly Trp Gly Cys Ile Gly Pro Gly Cys Gly Cys Leu Leu Lys
 1               5                  10                  15

Cys Leu

<210> SEQ ID NO 22
<211> LENGTH: 17
<212> TYPE: PRT
<213> ORGANISM: Artificial Sequence
<220> FEATURE:
<223> OTHER INFORMATION: synthetic peptide sequence

<400> SEQUENCE: 22

Glu Pro Trp Gly Cys Ile Gly Pro Gly Cys Ala Cys Leu Leu Gly
 1               5                  10                  15

Cys Leu

<210> SEQ ID NO 23
<211> LENGTH: 17
<212> TYPE: PRT
<213> ORGANISM: Artificial Sequence
<220> FEATURE:
<223> OTHER INFORMATION: synthetic peptide sequence

<400> SEQUENCE: 23

Glu Glu Trp Gly Cys Ile Gly Pro Gly Cys Ala Cys Leu Leu Asn
 1               5                  10                  15

Cys Ile

<210> SEQ ID NO 24
<211> LENGTH: 17
<212> TYPE: PRT
<213> ORGANISM: Artificial Sequence
<220> FEATURE:
<223> OTHER INFORMATION: synthetic peptide sequence

<400> SEQUENCE: 24

Glu Gln Trp Gly Cys Ile Gly Pro Gly Cys Lys Cys Leu Met Gly
 1               5                  10                  15

Cys Leu

<210> SEQ ID NO 25

```
<211> LENGTH: 17
<212> TYPE: PRT
<213> ORGANISM: Artificial Sequence
<220> FEATURE:
<223> OTHER INFORMATION: synthetic peptide sequence

<400> SEQUENCE: 25

Glu Gln Trp Gly Cys Ile Gly Pro Gly Cys Gly Cys Leu Leu Arg
 1               5                  10                  15

Cys Leu

<210> SEQ ID NO 26
<211> LENGTH: 17
<212> TYPE: PRT
<213> ORGANISM: Artificial Sequence
<220> FEATURE:
<223> OTHER INFORMATION: synthetic peptide sequence

<400> SEQUENCE: 26

Glu Ala Trp Gly Cys Ile Gly Pro Gly Cys Gly Cys Leu Met Ala
 1               5                  10                  15

Cys Leu

<210> SEQ ID NO 27
<211> LENGTH: 20
<212> TYPE: PRT
<213> ORGANISM: Artificial Sequence
<220> FEATURE:
<223> OTHER INFORMATION: synthetic peptide sequence
<220> FEATURE:
<221> NAME/KEY: unsure
<222> LOCATION: 1-3, 5, 14, 18
<223> OTHER INFORMATION: unknown amino acid

<400> SEQUENCE: 27

Xaa Xaa Xaa Glu Xaa Trp Gly Cys Ile Gly Pro Gly Cys Xaa Cys
 1               5                  10                  15

Leu Leu Xaa Cys Leu
                20

<210> SEQ ID NO 28
<211> LENGTH: 17
<212> TYPE: PRT
<213> ORGANISM: Artificial Sequence
<220> FEATURE:
<223> OTHER INFORMATION: synthetic peptide sequence

<400> SEQUENCE: 28

Asn Val Cys Glu Phe Trp Gly Cys Ile Gly Pro Gly Cys Ala Gln
 1               5                  10                  15

Leu Cys

<210> SEQ ID NO 29
<211> LENGTH: 20
<212> TYPE: PRT
<213> ORGANISM: Artificial Sequence
<220> FEATURE:
<223> OTHER INFORMATION: synthetic peptide sequence

<400> SEQUENCE: 29

Cys Ile Asp Glu Thr Trp Gly Cys Ile Gly Pro Gly Cys Glu Glu
 1               5                  10                  15

Leu Arg Cys Lys Arg
                20
```

```
<210> SEQ ID NO 30
<211> LENGTH: 20
<212> TYPE: PRT
<213> ORGANISM: Artificial Sequence
<220> FEATURE:
<223> OTHER INFORMATION: synthetic peptide sequence

<400> SEQUENCE: 30

Tyr Glu Trp Glu Gly Trp Gly Cys Ile Gly Pro Gly Cys Pro Ala
 1               5                  10                  15

Leu Gly Phe Gly Tyr
                 20

<210> SEQ ID NO 31
<211> LENGTH: 20
<212> TYPE: PRT
<213> ORGANISM: Artificial Sequence
<220> FEATURE:
<223> OTHER INFORMATION: synthetic peptide sequence

<400> SEQUENCE: 31

Arg Trp Asp Glu Glu Trp Gly Cys Ile Gly Pro Gly Cys Glu Trp
 1               5                  10                  15

Leu Val Val Arg Lys
                 20

<210> SEQ ID NO 32
<211> LENGTH: 16
<212> TYPE: PRT
<213> ORGANISM: Artificial Sequence
<220> FEATURE:
<223> OTHER INFORMATION: synthetic peptide sequence

<400> SEQUENCE: 32

His Trp Met Glu Arg Trp Gly Cys Ile Gly Pro Gly Cys Gly Phe
 1               5                  10                  15

Leu

<210> SEQ ID NO 33
<211> LENGTH: 16
<212> TYPE: PRT
<213> ORGANISM: Artificial Sequence
<220> FEATURE:
<223> OTHER INFORMATION: synthetic peptide sequence

<400> SEQUENCE: 33

Asn Trp Pro Glu Gly Trp Gly Cys Ile Gly Pro Gly Cys Lys Leu
 1               5                  10                  15

Leu

<210> SEQ ID NO 34
<211> LENGTH: 16
<212> TYPE: PRT
<213> ORGANISM: Artificial Sequence
<220> FEATURE:
<223> OTHER INFORMATION: synthetic peptide sequence

<400> SEQUENCE: 34

Phe Asn Trp Glu Lys Trp Gly Cys Ile Gly Pro Gly Cys Arg Thr
 1               5                  10                  15

Leu

<210> SEQ ID NO 35
```

<211> LENGTH: 16
<212> TYPE: PRT
<213> ORGANISM: Artificial Sequence
<220> FEATURE:
<223> OTHER INFORMATION: synthetic peptide sequence

<400> SEQUENCE: 35

Phe Ser Gly Glu Arg Trp Gly Cys Ile Gly Pro Gly Cys Gln Val
 1               5                  10                  15
Leu

<210> SEQ ID NO 36
<211> LENGTH: 16
<212> TYPE: PRT
<213> ORGANISM: Artificial Sequence
<220> FEATURE:
<223> OTHER INFORMATION: synthetic peptide sequence

<400> SEQUENCE: 36

Gly Gly Trp Glu Gly Trp Gly Cys Ile Gly Pro Gly Cys Arg Tyr
 1               5                  10                  15
Leu

<210> SEQ ID NO 37
<211> LENGTH: 16
<212> TYPE: PRT
<213> ORGANISM: Artificial Sequence
<220> FEATURE:
<223> OTHER INFORMATION: synthetic peptide sequence
<220> FEATURE:
<221> NAME/KEY: unsure
<222> LOCATION: 15
<223> OTHER INFORMATION: unknown amino acid

<400> SEQUENCE: 37

Leu Trp Phe Glu Arg Trp Gly Cys Ile Gly Pro Gly Cys Thr Xaa
 1               5                  10                  15
Leu

<210> SEQ ID NO 38
<211> LENGTH: 16
<212> TYPE: PRT
<213> ORGANISM: Artificial Sequence
<220> FEATURE:
<223> OTHER INFORMATION: synthetic peptide sequence

<400> SEQUENCE: 38

Gly Ile Pro Glu Gly Trp Gly Cys Ile Gly Pro Gly Cys Glu Trp
 1               5                  10                  15
Leu

<210> SEQ ID NO 39
<211> LENGTH: 16
<212> TYPE: PRT
<213> ORGANISM: Artificial Sequence
<220> FEATURE:
<223> OTHER INFORMATION: synthetic peptide sequence

<400> SEQUENCE: 39

Trp Trp Thr Glu Arg Trp Gly Cys Ile Gly Pro Gly Cys Ser Met
 1               5                  10                  15
Leu

<210> SEQ ID NO 40

```
<211> LENGTH: 20
<212> TYPE: PRT
<213> ORGANISM: Artificial Sequence
<220> FEATURE:
<223> OTHER INFORMATION: synthetic peptide sequence
<220> FEATURE:
<221> NAME/KEY: unsure
<222> LOCATION: 1, 3, 17-20
<223> OTHER INFORMATION: unknown amino acid

<400> SEQUENCE: 40

Xaa Cys Xaa Glu Arg Trp Gly Cys Ile Gly Pro Gly Cys Ser Met
 1               5                  10                  15

Leu Xaa Xaa Xaa Xaa
                20

<210> SEQ ID NO 41
<211> LENGTH: 16
<212> TYPE: PRT
<213> ORGANISM: Artificial Sequence
<220> FEATURE:
<223> OTHER INFORMATION: synthetic peptide sequence

<400> SEQUENCE: 41

Leu Gly Trp Glu Arg Trp Gly Cys Ile Gly Pro Gly Cys Arg Ala
 1               5                  10                  15

Leu

<210> SEQ ID NO 42
<211> LENGTH: 16
<212> TYPE: PRT
<213> ORGANISM: Artificial Sequence
<220> FEATURE:
<223> OTHER INFORMATION: synthetic peptide sequence

<400> SEQUENCE: 42

Ser Pro Trp Glu Gly Trp Gly Cys Ile Gly Pro Gly Cys Arg Trp
 1               5                  10                  15

Leu

<210> SEQ ID NO 43
<211> LENGTH: 16
<212> TYPE: PRT
<213> ORGANISM: Artificial Sequence
<220> FEATURE:
<223> OTHER INFORMATION: synthetic peptide sequence

<400> SEQUENCE: 43

Arg Gly Trp Glu Gly Trp Gly Cys Ile Gly Pro Gly Cys Ser Phe
 1               5                  10                  15

Leu

<210> SEQ ID NO 44
<211> LENGTH: 20
<212> TYPE: PRT
<213> ORGANISM: Artificial Sequence
<220> FEATURE:
<223> OTHER INFORMATION: synthetic peptide sequence
<220> FEATURE:
<221> NAME/KEY: unsure
<222> LOCATION: 1-2, 5, 14-15, 17-20
<223> OTHER INFORMATION: unknown amino acid

<400> SEQUENCE: 44

Xaa Xaa Trp Glu Xaa Trp Gly Cys Ile Gly Pro Gly Cys Xaa Xaa
 1               5                  10                  15
```

```
Leu Xaa Xaa Xaa Xaa
            20
```

<210> SEQ ID NO 45
<211> LENGTH: 27
<212> TYPE: PRT
<213> ORGANISM: Artificial Sequence
<220> FEATURE:
<223> OTHER INFORMATION: synthetic peptide sequence

<400> SEQUENCE: 45

```
Cys Ser Trp Val Leu Val Gln Cys Gly Gly Glu Trp Trp His Cys
  1               5                  10                  15

Cys Gly Leu Gly Cys Gly Leu Val Val Asn Ala Cys
                 20                  25
```

<210> SEQ ID NO 46
<211> LENGTH: 27
<212> TYPE: PRT
<213> ORGANISM: Artificial Sequence
<220> FEATURE:
<223> OTHER INFORMATION: synthetic peptide sequence

<400> SEQUENCE: 46

```
Cys Ala Trp Val Ser Phe Glu Cys Gly Gly Glu Val Trp His Cys
  1               5                  10                  15

Cys Gly Leu Gly Cys Gly Trp Val Trp Lys Ala Cys
                 20                  25
```

<210> SEQ ID NO 47
<211> LENGTH: 27
<212> TYPE: PRT
<213> ORGANISM: Artificial Sequence
<220> FEATURE:
<223> OTHER INFORMATION: synthetic peptide sequence

<400> SEQUENCE: 47

```
Cys Ala Trp Val Leu Val Gln Cys Gly Gly Glu Trp Trp His Cys
  1               5                  10                  15

Cys Gly Pro Gly Cys Glu Phe Val Val Asp Ala Cys
                 20                  25
```

<210> SEQ ID NO 48
<211> LENGTH: 27
<212> TYPE: PRT
<213> ORGANISM: Artificial Sequence
<220> FEATURE:
<223> OTHER INFORMATION: synthetic peptide sequence

<400> SEQUENCE: 48

```
Cys Ala Trp Val Ala Val Tyr Cys Gly Gly Glu Leu Trp His Cys
  1               5                  10                  15

Cys Gly Pro Gly Cys Gly Phe Val Val Asp Ser Cys
                 20                  25
```

<210> SEQ ID NO 49
<211> LENGTH: 27
<212> TYPE: PRT
<213> ORGANISM: Artificial Sequence
<220> FEATURE:
<223> OTHER INFORMATION: synthetic peptide sequence

<400> SEQUENCE: 49

```
Cys Ala Trp Val Arg Val Trp Cys Phe Gly Glu Trp Trp Asp Cys
```

```
                1               5              10              15

Cys Gly Leu Gly Cys Gly Trp Val Val Asn Val Cys
                20                      25

<210> SEQ ID NO 50
<211> LENGTH: 27
<212> TYPE: PRT
<213> ORGANISM: Artificial Sequence
<220> FEATURE:
<223> OTHER INFORMATION: synthetic peptide sequence

<400> SEQUENCE: 50

Cys Ala Trp Val Arg Val Leu Cys Gly Gly Glu Trp Trp His Cys
  1               5                      10                      15

Cys Gly Leu Gly Cys Gly Trp Val Val Glu Ala Cys
                20                      25

<210> SEQ ID NO 51
<211> LENGTH: 27
<212> TYPE: PRT
<213> ORGANISM: Artificial Sequence
<220> FEATURE:
<223> OTHER INFORMATION: synthetic peptide sequence

<400> SEQUENCE: 51

Cys Ser Trp Val Ser Val Leu Cys Gly Gly Glu Trp Trp Gln Cys
  1               5                      10                      15

Cys Gly Pro Gly Cys Gly Leu Val Val Asn Ala Cys
                20                      25

<210> SEQ ID NO 52
<211> LENGTH: 27
<212> TYPE: PRT
<213> ORGANISM: Artificial Sequence
<220> FEATURE:
<223> OTHER INFORMATION: synthetic peptide sequence

<400> SEQUENCE: 52

Cys Ser Trp Val Ser Leu Gln Cys Gly Gly Glu Trp Trp His Cys
  1               5                      10                      15

Cys Gly Gly Gly Cys Gly Trp Val Val Asn Val Cys
                20                      25

<210> SEQ ID NO 53
<211> LENGTH: 27
<212> TYPE: PRT
<213> ORGANISM: Artificial Sequence
<220> FEATURE:
<223> OTHER INFORMATION: synthetic peptide sequence

<400> SEQUENCE: 53

Cys Ser Trp Val Leu Leu His Cys Gly Gly Glu Trp Trp His Cys
  1               5                      10                      15

Cys Gly Gly Gly Cys Gly Trp Val Gly Glu Ala Cys
                20                      25

<210> SEQ ID NO 54
<211> LENGTH: 27
<212> TYPE: PRT
<213> ORGANISM: Artificial Sequence
<220> FEATURE:
<223> OTHER INFORMATION: synthetic peptide sequence

<400> SEQUENCE: 54
```

Cys Ser Trp Val Leu Leu Glu Cys Gly Gly Glu Leu Trp Glu Cys
1               5                   10                  15

Cys Gly Leu Gly Cys Gly Trp Val Ala Asp Ala Cys
                20                  25

<210> SEQ ID NO 55
<211> LENGTH: 27
<212> TYPE: PRT
<213> ORGANISM: Artificial Sequence
<220> FEATURE:
<223> OTHER INFORMATION: synthetic peptide sequence

<400> SEQUENCE: 55

Cys Ser Trp Val Val Phe Glu Cys Leu Gly Glu Ser Trp His Cys
1               5                   10                  15

Cys Gly Gly Gly Cys Gly Trp Val Val His Ala Cys
                20                  25

<210> SEQ ID NO 56
<211> LENGTH: 27
<212> TYPE: PRT
<213> ORGANISM: Artificial Sequence
<220> FEATURE:
<223> OTHER INFORMATION: synthetic peptide sequence

<400> SEQUENCE: 56

Cys Ala Trp Val Ser Val Glu Cys Gly Gly Glu Trp Trp His Cys
1               5                   10                  15

Cys Gly Pro Gly Cys Gly Trp Val Val Asp Ala Cys
                20                  25

<210> SEQ ID NO 57
<211> LENGTH: 20
<212> TYPE: PRT
<213> ORGANISM: Artificial Sequence
<220> FEATURE:
<223> OTHER INFORMATION: synthetic peptide sequence

<400> SEQUENCE: 57

Tyr Glu Val Glu Ala Trp Asp Cys Met Gly Pro Gly Cys Ala Asn
1               5                   10                  15

Leu Phe Glu Ala His
                20

<210> SEQ ID NO 58
<211> LENGTH: 20
<212> TYPE: PRT
<213> ORGANISM: Artificial Sequence
<220> FEATURE:
<223> OTHER INFORMATION: synthetic peptide sequence

<400> SEQUENCE: 58

Tyr Glu Phe Glu Gly Trp Asp Cys Met Gly Pro Gly Cys Ala Ser
1               5                   10                  15

Val Phe Gly Ala His
                20

<210> SEQ ID NO 59
<211> LENGTH: 20
<212> TYPE: PRT
<213> ORGANISM: Artificial Sequence
<220> FEATURE:
<223> OTHER INFORMATION: synthetic peptide sequence

<400> SEQUENCE: 59

```
Tyr Glu Gly Glu Ser Trp Gly Cys Ile Gly Pro Gly Cys Ala Ser
1               5                   10                  15

Leu Phe Asp Ala His
            20

<210> SEQ ID NO 60
<211> LENGTH: 20
<212> TYPE: PRT
<213> ORGANISM: Artificial Sequence
<220> FEATURE:
<223> OTHER INFORMATION: synthetic peptide sequence

<400> SEQUENCE: 60

Tyr Glu Val Glu Val Trp Glu Cys Ile Gly Pro Gly Cys Gly Tyr
1               5                   10                  15

Leu Phe Gly Ala His
            20

<210> SEQ ID NO 61
<211> LENGTH: 20
<212> TYPE: PRT
<213> ORGANISM: Artificial Sequence
<220> FEATURE:
<223> OTHER INFORMATION: synthetic peptide sequence

<400> SEQUENCE: 61

Tyr Glu Val Glu Gly Trp Gly Cys Met Gly Pro Gly Cys Ala Phe
1               5                   10                  15

Leu Leu Glu Ala His
            20

<210> SEQ ID NO 62
<211> LENGTH: 20
<212> TYPE: PRT
<213> ORGANISM: Artificial Sequence
<220> FEATURE:
<223> OTHER INFORMATION: synthetic peptide sequence

<400> SEQUENCE: 62

Tyr Ser Phe Glu Gly Trp Gly Cys Ile Gly Pro Gly Cys Ala Tyr
1               5                   10                  15

Leu Phe Glu Gly His
            20

<210> SEQ ID NO 63
<211> LENGTH: 20
<212> TYPE: PRT
<213> ORGANISM: Artificial Sequence
<220> FEATURE:
<223> OTHER INFORMATION: synthetic peptide sequence

<400> SEQUENCE: 63

Tyr Asp Phe Glu Gly Trp Gly Cys Ile Gly Pro Gly Cys Gly Asn
1               5                   10                  15

Leu Leu Glu Ala His
            20

<210> SEQ ID NO 64
<211> LENGTH: 20
<212> TYPE: PRT
<213> ORGANISM: Artificial Sequence
<220> FEATURE:
<223> OTHER INFORMATION: synthetic peptide sequence
```

```
<400> SEQUENCE: 64

Tyr Asp Phe Glu Gly Trp Asp Cys Thr Gly Pro Gly Cys Ala Tyr
 1               5                  10                  15

Leu Phe Glu Gly His
            20

<210> SEQ ID NO 65
<211> LENGTH: 20
<212> TYPE: PRT
<213> ORGANISM: Artificial Sequence
<220> FEATURE:
<223> OTHER INFORMATION: synthetic peptide sequence

<400> SEQUENCE: 65

Asp Glu Val Glu Ser Trp Gly Cys Ile Gly Pro Gly Cys Ala Tyr
 1               5                  10                  15

Leu Phe Gly Ala Leu
            20

<210> SEQ ID NO 66
<211> LENGTH: 20
<212> TYPE: PRT
<213> ORGANISM: Artificial Sequence
<220> FEATURE:
<223> OTHER INFORMATION: synthetic peptide sequence

<400> SEQUENCE: 66

Ser Glu Val Glu Val Trp His Cys Ile Gly Pro Gly Cys Val Tyr
 1               5                  10                  15

Leu Phe Glu Ala Tyr
            20

<210> SEQ ID NO 67
<211> LENGTH: 20
<212> TYPE: PRT
<213> ORGANISM: Artificial Sequence
<220> FEATURE:
<223> OTHER INFORMATION: synthetic peptide sequence

<400> SEQUENCE: 67

Phe Glu Phe Glu Gly Trp Glu Cys Met Gly Pro Gly Cys Ala Glu
 1               5                  10                  15

Leu Phe Ala Gly His
            20

<210> SEQ ID NO 68
<211> LENGTH: 20
<212> TYPE: PRT
<213> ORGANISM: Artificial Sequence
<220> FEATURE:
<223> OTHER INFORMATION: synthetic peptide sequence

<400> SEQUENCE: 68

His Asp Val Glu Gly Trp Gly Cys Ile Gly Pro Gly Cys Ala Asp
 1               5                  10                  15

Leu Phe Glu Ala Phe
            20

<210> SEQ ID NO 69
<211> LENGTH: 20
<212> TYPE: PRT
<213> ORGANISM: Artificial Sequence
<220> FEATURE:
<223> OTHER INFORMATION: synthetic peptide sequence
```

```
<400> SEQUENCE: 69

Tyr Glu Phe Glu Gly Trp Gly Cys Ile Gly Pro Gly Cys Ala Tyr
 1               5                  10                  15

Leu Phe Glu Ala His
                20

<210> SEQ ID NO 70
<211> LENGTH: 27
<212> TYPE: PRT
<213> ORGANISM: Artificial Sequence
<220> FEATURE:
<223> OTHER INFORMATION: synthetic peptide sequence
<220> FEATURE:
<221> NAME/KEY: Mutagen
<222> LOCATION: 2-7, 9-14, 17-19, 21-26
<223> OTHER INFORMATION: More than one possible amino acid

<400> SEQUENCE: 70

Cys Xaa Xaa Xaa Xaa Xaa Xaa Cys Xaa Xaa Xaa Xaa Xaa Xaa Cys
 1               5                  10                  15

Cys Xaa Xaa Xaa Cys Xaa Xaa Xaa Xaa Xaa Xaa Cys
                20                  25

<210> SEQ ID NO 71
<211> LENGTH: 6
<212> TYPE: PRT
<213> ORGANISM: Artificial Sequence
<220> FEATURE:
<223> OTHER INFORMATION: synthetic peptide sequence
<220> FEATURE:
<221> NAME/KEY: Mutagen
<222> LOCATION: 2
<223> OTHER INFORMATION: Xaa can be Cys or Ile

<400> SEQUENCE: 71

Cys Xaa Gly Pro Gly Cys
 1               5

<210> SEQ ID NO 72
<211> LENGTH: 218
<212> TYPE: PRT
<213> ORGANISM: Homo sapiens

<400> SEQUENCE: 72

Pro Ala Pro Glu Leu Leu Gly Gly Pro Ser Val Phe Leu Phe Pro
 1               5                  10                  15

Pro Lys Pro Lys Asp Thr Leu Met Ile Ser Arg Thr Pro Glu Val
                20                  25                  30

Thr Cys Val Val Val Asp Val Ser His Glu Asp Pro Glu Val Lys
                35                  40                  45

Phe Asn Trp Tyr Val Asp Gly Val Glu Val His Asn Ala Lys Thr
                50                  55                  60

Lys Pro Arg Glu Glu Gln Tyr Asn Ser Thr Tyr Arg Val Val Ser
                65                  70                  75

Val Leu Thr Val Leu His Gln Asp Trp Leu Asn Gly Lys Glu Tyr
                80                  85                  90

Lys Cys Lys Val Ser Asn Lys Ala Leu Pro Ala Pro Ile Glu Lys
                95                  100                 105

Thr Ile Ser Lys Ala Lys Gly Gln Pro Arg Glu Pro Gln Val Tyr
                110                 115                 120

Thr Leu Pro Pro Ser Arg Glu Glu Met Thr Lys Asn Gln Val Ser
```

```
                        125                 130                 135
Leu Thr Cys Leu Val Lys Gly Phe Tyr Pro Ser Asp Ile Ala Val
                140                 145                 150
Glu Trp Glu Ser Asn Gly Gln Pro Glu Asn Asn Tyr Lys Thr Thr
                155                 160                 165
Pro Pro Val Leu Asp Ser Asp Gly Ser Phe Phe Leu Tyr Ser Lys
                170                 175                 180
Leu Thr Val Asp Lys Ser Arg Trp Gln Gln Gly Asn Val Phe Ser
                185                 190                 195
Cys Ser Val Met His Glu Ala Leu His Asn His Tyr Thr Gln Lys
                200                 205                 210
Ser Leu Ser Leu Ser Pro Gly Lys
                215

<210> SEQ ID NO 73
<211> LENGTH: 218
<212> TYPE: PRT
<213> ORGANISM: Homo sapiens

<400> SEQUENCE: 73

Pro Ala Pro Glu Leu Leu Gly Gly Pro Ser Val Phe Leu Phe Pro
  1               5                  10                  15
Pro Lys Pro Lys Asp Thr Leu Met Ile Ser Arg Thr Pro Glu Val
                 20                  25                  30
Thr Cys Val Val Val Asp Val Ser His Glu Asp Pro Glu Val Lys
                 35                  40                  45
Phe Asn Trp Tyr Val Asp Gly Val Glu Val His Asn Ala Lys Thr
                 50                  55                  60
Lys Pro Arg Glu Glu Gln Tyr Asn Ser Thr Tyr Arg Val Val Ser
                 65                  70                  75
Val Leu Thr Val Leu His Gln Asp Trp Leu Asn Gly Lys Glu Tyr
                 80                  85                  90
Lys Cys Lys Val Ser Asn Lys Ala Leu Pro Ala Pro Ile Glu Lys
                 95                 100                 105
Thr Ile Ser Lys Ala Lys Gly Gln Pro Arg Glu Pro Gln Val Tyr
                110                 115                 120
Thr Leu Pro Pro Ser Arg Asp Glu Leu Thr Lys Asn Gln Val Ser
                125                 130                 135
Leu Thr Cys Leu Val Lys Gly Phe Tyr Pro Ser Asp Ile Ala Val
                140                 145                 150
Glu Trp Glu Ser Asn Gly Gln Pro Glu Asn Asn Tyr Lys Thr Thr
                155                 160                 165
Pro Pro Val Leu Asp Ser Asp Gly Ser Phe Phe Leu Tyr Ser Lys
                170                 175                 180
Leu Thr Val Asp Lys Ser Arg Trp Gln Gln Gly Asn Val Phe Ser
                185                 190                 195
Cys Ser Val Met His Glu Ala Leu His Asn His Tyr Thr Gln Lys
                200                 205                 210
Ser Leu Ser Leu Ser Pro Gly Lys
                215

<210> SEQ ID NO 74
<211> LENGTH: 217
<212> TYPE: PRT
<213> ORGANISM: Homo sapiens
```

-continued

```
<400> SEQUENCE: 74

Pro Ala Pro Pro Val Ala Gly Pro Ser Val Phe Leu Phe Pro Pro
  1               5                  10                  15

Lys Pro Lys Asp Thr Leu Met Ile Ser Arg Thr Pro Glu Val Thr
             20                  25                  30

Cys Val Val Asp Val Ser His Glu Asp Pro Glu Val Gln Phe
             35                  40                  45

Asn Trp Tyr Val Asp Gly Val Glu Val His Asn Ala Lys Thr Lys
             50                  55                  60

Pro Arg Glu Glu Gln Phe Asn Ser Thr Phe Arg Val Val Ser Val
             65                  70                  75

Leu Thr Val Val His Gln Asp Trp Leu Asn Gly Lys Glu Tyr Lys
             80                  85                  90

Cys Lys Val Ser Asn Lys Gly Leu Pro Ala Pro Ile Glu Lys Thr
             95                 100                 105

Ile Ser Lys Thr Lys Gly Gln Pro Arg Glu Pro Gln Val Tyr Thr
            110                 115                 120

Leu Pro Pro Ser Arg Glu Glu Met Thr Lys Asn Gln Val Ser Leu
            125                 130                 135

Thr Cys Leu Val Lys Gly Phe Tyr Pro Ser Asp Ile Ala Val Glu
            140                 145                 150

Trp Glu Ser Asn Gly Gln Pro Glu Asn Asn Tyr Lys Thr Thr Pro
            155                 160                 165

Pro Met Leu Asp Ser Asp Gly Ser Phe Phe Leu Tyr Ser Lys Leu
            170                 175                 180

Thr Val Asp Lys Ser Arg Trp Gln Gln Gly Asn Val Phe Ser Cys
            185                 190                 195

Ser Val Met His Glu Ala Leu His Asn His Tyr Thr Gln Lys Ser
            200                 205                 210

Leu Ser Leu Ser Pro Gly Lys
            215

<210> SEQ ID NO 75
<211> LENGTH: 218
<212> TYPE: PRT
<213> ORGANISM: Homo sapiens

<400> SEQUENCE: 75

Pro Ala Pro Glu Leu Leu Gly Gly Pro Ser Val Phe Leu Phe Pro
  1               5                  10                  15

Pro Lys Pro Lys Asp Thr Leu Met Ile Ser Arg Thr Pro Glu Val
             20                  25                  30

Thr Cys Val Val Asp Val Ser His Glu Asp Pro Glu Val Gln
             35                  40                  45

Phe Lys Trp Tyr Val Asp Gly Val Glu Val His Asn Ala Lys Thr
             50                  55                  60

Lys Pro Arg Glu Glu Gln Phe Asn Ser Thr Phe Arg Val Val Ser
             65                  70                  75

Val Leu Thr Val Leu His Gln Asp Trp Leu Asn Gly Lys Glu Tyr
             80                  85                  90

Lys Cys Lys Val Ser Asn Lys Ala Leu Pro Ala Pro Ile Glu Lys
             95                 100                 105

Thr Ile Ser Lys Thr Lys Gly Gln Pro Arg Glu Pro Gln Val Tyr
            110                 115                 120
```

```
Thr Leu Pro Pro Ser Arg Glu Glu Met Thr Lys Asn Gln Val Ser
            125                 130                 135

Leu Thr Cys Leu Val Lys Gly Phe Tyr Pro Ser Asp Ile Ala Val
            140                 145                 150

Glu Trp Glu Ser Ser Gly Gln Pro Glu Asn Asn Tyr Asn Thr Thr
            155                 160                 165

Pro Pro Met Leu Asp Ser Asp Gly Ser Phe Phe Leu Tyr Ser Lys
            170                 175                 180

Leu Thr Val Asp Lys Ser Arg Trp Gln Gln Gly Asn Ile Phe Ser
            185                 190                 195

Cys Ser Val Met His Glu Ala Leu His Asn Arg Phe Thr Gln Lys
            200                 205                 210

Ser Leu Ser Leu Ser Pro Gly Lys
            215

<210> SEQ ID NO 76
<211> LENGTH: 218
<212> TYPE: PRT
<213> ORGANISM: Homo sapiens

<400> SEQUENCE: 76

Pro Ala Pro Glu Phe Leu Gly Gly Pro Ser Val Phe Leu Phe Pro
  1               5                  10                  15

Pro Lys Pro Lys Asp Thr Leu Met Ile Ser Arg Thr Pro Glu Val
            20                  25                  30

Thr Cys Val Val Val Asp Val Ser Gln Glu Asp Pro Glu Val Gln
            35                  40                  45

Phe Asn Trp Tyr Val Asp Gly Val Glu Val His Asn Ala Lys Thr
            50                  55                  60

Lys Pro Arg Glu Glu Gln Phe Asn Ser Thr Tyr Arg Val Val Ser
            65                  70                  75

Val Leu Thr Val Leu His Gln Asp Trp Leu Asn Gly Lys Glu Tyr
            80                  85                  90

Lys Cys Lys Val Ser Asn Lys Gly Leu Pro Ser Ser Ile Glu Lys
            95                 100                 105

Thr Ile Ser Lys Ala Lys Gly Gln Pro Arg Glu Pro Gln Val Tyr
           110                 115                 120

Thr Leu Pro Pro Ser Gln Glu Glu Met Thr Lys Asn Gln Val Ser
           125                 130                 135

Leu Thr Cys Leu Val Lys Gly Phe Tyr Pro Ser Asp Ile Ala Val
           140                 145                 150

Glu Trp Glx Ser Asn Gly Gln Pro Glu Asn Asn Tyr Lys Thr Thr
           155                 160                 165

Pro Pro Val Leu Asp Ser Asp Gly Ser Phe Phe Leu Tyr Ser Arg
           170                 175                 180

Leu Thr Val Asp Lys Ser Arg Trp Gln Glu Gly Asn Val Phe Ser
           185                 190                 195

Cys Ser Val Met His Glu Ala Leu His Asn His Tyr Thr Gln Lys
           200                 205                 210

Ser Leu Ser Leu Ser Leu Gly Lys
           215

<210> SEQ ID NO 77
<211> LENGTH: 215
<212> TYPE: PRT
<213> ORGANISM: Mus musculus
```

<400> SEQUENCE: 77

```
Thr Val Pro Glu Val Ser Ser Val Phe Ile Phe Pro Lys Pro
 1               5                  10                  15
Lys Asp Val Leu Thr Ile Thr Leu Thr Pro Lys Val Thr Cys Val
                20                  25                  30
Val Val Asp Ile Ser Lys Asp Asp Pro Glu Val Gln Phe Ser Trp
                35                  40                  45
Phe Val Asp Asp Val Glu Val His Thr Ala Gln Thr Gln Pro Arg
                50                  55                  60
Glu Glu Gln Phe Asn Ser Thr Phe Arg Ser Val Ser Glu Leu Pro
                65                  70                  75
Ile Met His Gln Asp Cys Leu Asn Gly Lys Glu Phe Lys Cys Arg
                80                  85                  90
Val Asn Ser Ala Ala Phe Pro Ala Pro Ile Glu Lys Thr Ile Ser
                95                 100                 105
Lys Thr Lys Gly Arg Pro Lys Ala Pro Gln Val Tyr Thr Ile Pro
               110                 115                 120
Pro Pro Lys Glu Gln Met Ala Lys Asp Lys Val Ser Leu Thr Cys
               125                 130                 135
Met Ile Thr Asp Phe Phe Pro Glu Asp Ile Thr Val Glu Trp Gln
               140                 145                 150
Trp Asn Gly Gln Pro Ala Glu Asn Tyr Lys Asn Thr Gln Pro Ile
               155                 160                 165
Met Asp Thr Asp Gly Ser Tyr Phe Val Tyr Ser Lys Leu Asn Val
               170                 175                 180
Gln Lys Ser Asn Trp Glu Ala Gly Asn Thr Phe Thr Cys Ser Val
               185                 190                 195
Leu His Glu Gly Leu His Asn His His Thr Glu Lys Ser Leu Ser
               200                 205                 210
His Ser Pro Gly Lys
               215
```

<210> SEQ ID NO 78
<211> LENGTH: 218
<212> TYPE: PRT
<213> ORGANISM: Mus musculus

<400> SEQUENCE: 78

```
Pro Ala Pro Asn Leu Leu Gly Gly Pro Ser Val Phe Ile Phe Pro
 1               5                  10                  15
Pro Lys Ile Lys Asp Val Leu Met Ile Ser Leu Ser Pro Ile Val
                20                  25                  30
Thr Cys Val Val Val Asp Val Ser Glu Asp Asp Pro Asp Val Gln
                35                  40                  45
Ile Ser Trp Phe Val Asn Asn Val Glu Val His Thr Ala Gln Thr
                50                  55                  60
Gln Thr His Arg Glu Asp Tyr Asn Ser Thr Leu Arg Val Val Ser
                65                  70                  75
Ala Leu Pro Ile Gln His Gln Asp Trp Met Ser Gly Lys Glu Phe
                80                  85                  90
Lys Cys Lys Val Asn Asn Lys Asp Leu Pro Ala Pro Ile Glu Arg
                95                 100                 105
Thr Ile Ser Lys Pro Lys Gly Ser Val Arg Ala Pro Gln Val Tyr
               110                 115                 120
```

-continued

```
Val Leu Pro Pro Glu Glu Glu Met Thr Lys Lys Gln Val Thr
            125                 130                 135

Leu Thr Cys Met Val Thr Asp Phe Met Pro Glu Asp Ile Tyr Val
            140                 145                 150

Glu Trp Thr Asn Asn Gly Lys Thr Glu Leu Asn Tyr Lys Asn Thr
            155                 160                 165

Glu Pro Val Leu Asp Ser Asp Gly Ser Tyr Phe Met Tyr Ser Lys
            170                 175                 180

Leu Arg Val Glu Lys Lys Asn Trp Val Glu Arg Asn Ser Tyr Ser
            185                 190                 195

Cys Ser Val Val His Glu Gly Leu His Asn His His Thr Thr Lys
            200                 205                 210

Ser Phe Ser Arg Thr Pro Gly Lys
            215
```

<210> SEQ ID NO 79
<211> LENGTH: 218
<212> TYPE: PRT
<213> ORGANISM: Mus musculus

<400> SEQUENCE: 79

```
Pro Ala Pro Asn Leu Glu Gly Gly Pro Ser Val Phe Ile Phe Pro
 1               5                  10                  15

Pro Asn Ile Lys Asp Val Leu Met Ile Ser Leu Thr Pro Lys Val
            20                  25                  30

Thr Cys Val Val Val Asp Val Ser Glu Asp Asp Pro Asp Val Gln
            35                  40                  45

Ile Ser Trp Phe Val Asn Asn Val Glu Val His Thr Ala Gln Thr
            50                  55                  60

Gln Thr His Arg Glu Asp Tyr Asn Ser Thr Ile Arg Val Val Ser
            65                  70                  75

His Leu Pro Ile Gln His Gln Asp Trp Met Ser Gly Lys Glu Phe
            80                  85                  90

Lys Cys Lys Val Asn Asn Lys Asp Leu Pro Ser Pro Ile Glu Arg
            95                  100                 105

Thr Ile Ser Lys Pro Lys Gly Leu Val Arg Ala Pro Gln Val Tyr
            110                 115                 120

Thr Leu Pro Pro Pro Ala Glu Gln Leu Ser Arg Lys Asp Val Ser
            125                 130                 135

Leu Thr Cys Leu Val Val Gly Phe Asn Pro Gly Asp Ile Ser Val
            140                 145                 150

Glu Trp Thr Ser Asn Gly His Thr Glu Glu Asn Tyr Lys Asp Thr
            155                 160                 165

Ala Pro Val Leu Asp Ser Asp Gly Ser Tyr Phe Ile Tyr Ser Lys
            170                 175                 180

Leu Asn Met Lys Thr Ser Lys Trp Glu Lys Thr Asp Ser Phe Ser
            185                 190                 195

Cys Asn Val Arg His Glu Gly Leu Lys Asn Tyr Tyr Leu Lys Lys
            200                 205                 210

Thr Ile Ser Arg Ser Pro Gly Lys
            215
```

<210> SEQ ID NO 80
<211> LENGTH: 218
<212> TYPE: PRT

<213> ORGANISM: Mus musculus

<400> SEQUENCE: 80

Pro Pro Gly Asn Ile Leu Gly Gly Pro Ser Val Phe Ile Phe Pro
 1               5                  10                  15

Pro Lys Pro Lys Asp Ala Leu Met Ile Ser Leu Thr Pro Lys Val
             20                  25                  30

Thr Cys Val Val Val Asp Val Ser Glu Asp Pro Asp Val His
             35                  40                  45

Val Ser Trp Phe Val Asp Asn Lys Glu Val His Thr Ala Trp Thr
             50                  55                  60

Gln Pro Arg Glu Ala Gln Tyr Asn Ser Thr Phe Arg Val Val Ser
             65                  70                  75

Ala Leu Pro Ile Gln His Gln Asp Trp Met Arg Gly Lys Glu Phe
             80                  85                  90

Lys Cys Lys Val Asn Asn Lys Ala Leu Pro Ala Pro Ile Glu Arg
             95                 100                 105

Thr Ile Ser Lys Pro Lys Gly Arg Ala Gln Thr Pro Gln Val Tyr
            110                 115                 120

Thr Ile Pro Pro Pro Arg Glu Gln Met Ser Lys Lys Lys Val Ser
            125                 130                 135

Leu Thr Cys Leu Val Thr Asn Phe Phe Ser Glu Ala Ile Ser Val
            140                 145                 150

Glu Trp Glu Arg Asn Gly Glu Leu Glu Gln Asp Tyr Lys Asn Thr
            155                 160                 165

Pro Pro Ile Leu Asp Ser Asp Gly Thr Tyr Phe Leu Tyr Ser Lys
            170                 175                 180

Leu Thr Val Asp Thr Asp Ser Trp Leu Gln Gly Glu Ile Phe Thr
            185                 190                 195

Cys Ser Val Val His Glu Ala Leu His Asn His His Thr Gln Lys
            200                 205                 210

Asn Leu Ser Arg Ser Pro Gly Lys
            215

<210> SEQ ID NO 81
<211> LENGTH: 20
<212> TYPE: PRT
<213> ORGANISM: Artificial Sequence
<220> FEATURE:
<223> OTHER INFORMATION: synthetic peptide sequence

<400> SEQUENCE: 81

Gln Val Tyr Glu Ser Trp Gly Cys Ile Gly Pro Gly Cys Ala Cys
 1               5                  10                  15

Leu Gln Ala Cys Leu
             20

<210> SEQ ID NO 82
<211> LENGTH: 46
<212> TYPE: PRT
<213> ORGANISM: Artificial Sequence
<220> FEATURE:
<223> OTHER INFORMATION: synthetic peptide sequence

<400> SEQUENCE: 82

Gln Val Tyr Glu Ser Trp Gly Cys Ile Gly Pro Gly Cys Ala Cys
 1               5                  10                  15

Leu Gln Ala Cys Leu Gly Gly Gly Ser Gly Gly Gln Val Tyr Glu

-continued

Ser Trp Gly Cys Ile Gly Pro Gly Cys Ala Cys Leu Gln Ala Cys
            35                  40                  45
Leu

<210> SEQ ID NO 83
<211> LENGTH: 27
<212> TYPE: PRT
<213> ORGANISM: Artificial Sequence
<220> FEATURE:
<223> OTHER INFORMATION: synthetic peptide sequence

<400> SEQUENCE: 83

Cys Ala Trp Val Ser Val Glu Cys Gly Gly Glu Trp Trp His Cys
  1               5                  10                  15

Cys Gly Pro Gly Cys Gly Trp Val Val Asp Ala Cys
            20                  25

<210> SEQ ID NO 84
<211> LENGTH: 20
<212> TYPE: PRT
<213> ORGANISM: Artificial Sequence
<220> FEATURE:
<223> OTHER INFORMATION: synthetic peptide sequence

<400> SEQUENCE: 84

Tyr Ser Phe Glu Gly Trp Gly Cys Ile Gly Pro Gly Cys Ala Tyr
  1               5                  10                  15

Leu Phe Glu Gly His
            20

<210> SEQ ID NO 85
<211> LENGTH: 20
<212> TYPE: PRT
<213> ORGANISM: Artificial Sequence
<220> FEATURE:
<223> OTHER INFORMATION: synthetic peptide sequence

<400> SEQUENCE: 85

Tyr Glu Trp Glu Gly Trp Gly Cys Ile Gly Pro Gly Cys Pro Ala
  1               5                  10                  15

Leu Gly Phe Gly Tyr
            20

<210> SEQ ID NO 86
<211> LENGTH: 20
<212> TYPE: PRT
<213> ORGANISM: Artificial Sequence
<220> FEATURE:
<223> OTHER INFORMATION: synthetic peptide sequence

<400> SEQUENCE: 86

Gln Arg Asn Glu Ala Trp Gly Cys Ile Gly Pro Gly Cys Glu Met
  1               5                  10                  15

Leu Cys Ala Trp Cys
            20

<210> SEQ ID NO 87
<211> LENGTH: 20
<212> TYPE: PRT
<213> ORGANISM: Artificial Sequence
<220> FEATURE:
<223> OTHER INFORMATION: synthetic peptide sequence

```
<400> SEQUENCE: 87

Thr Gln Ala Glu Arg Trp Gly Cys Ile Gly Pro Gly Cys Glu Cys
  1               5                  10                  15

Leu Met Ser Cys Val
                20

<210> SEQ ID NO 88
<211> LENGTH: 20
<212> TYPE: PRT
<213> ORGANISM: Artificial Sequence
<220> FEATURE:
<223> OTHER INFORMATION: synthetic peptide sequence

<400> SEQUENCE: 88

Cys Ile Asp Glu Thr Trp Gly Cys Ile Gly Pro Gly Cys Glu Glu
  1               5                  10                  15

Leu Arg Cys Lys Arg
                20

<210> SEQ ID NO 89
<211> LENGTH: 17
<212> TYPE: PRT
<213> ORGANISM: Artificial Sequence
<220> FEATURE:
<223> OTHER INFORMATION: synthetic peptide sequence

<400> SEQUENCE: 89

Asn Val Cys Glu Phe Trp Gly Cys Ile Gly Pro Gly Cys Ala Gln
  1               5                  10                  15

Leu Cys

<210> SEQ ID NO 90
<211> LENGTH: 27
<212> TYPE: PRT
<213> ORGANISM: Artificial Sequence
<220> FEATURE:
<223> OTHER INFORMATION: synthetic peptide sequence
<220> FEATURE:
<221> NAME/KEY: Mutagen
<222> LOCATION: 1-14, 16, 21-27
<223> OTHER INFORMATION: More than one possible amino acid

<400> SEQUENCE: 90

Xaa Xaa Xaa Xaa Xaa Xaa Xaa Xaa Xaa Xaa Xaa Xaa Xaa Xaa Cys
  1               5                  10                  15

Xaa Gly Pro Gly Cys Xaa Xaa Xaa Xaa Xaa Xaa Xaa
                20                  25

<210> SEQ ID NO 91
<211> LENGTH: 20
<212> TYPE: PRT
<213> ORGANISM: Artificial Sequence
<220> FEATURE:
<223> OTHER INFORMATION: synthetic peptide sequence
<220> FEATURE:
<221> NAME/KEY: Mutagen
<222> LOCATION: 1-3, 5, 14-15, 17-20
<223> OTHER INFORMATION: More than one possible amino acid

<400> SEQUENCE: 91

Xaa Xaa Xaa Glu Xaa Trp Gly Cys Ile Gly Pro Gly Cys Xaa Xaa
  1               5                  10                  15

Leu Xaa Xaa Xaa Xaa
                20
```

```
<210> SEQ ID NO 92
<211> LENGTH: 20
<212> TYPE: PRT
<213> ORGANISM: Artificial Sequence
<220> FEATURE:
<223> OTHER INFORMATION: synthetic peptide sequence
<220> FEATURE:
<221> NAME/KEY: Mutagen
<222> LOCATION: 1-7, 9, 14-20
<223> OTHER INFORMATION: More than one possible amino acid

<400> SEQUENCE: 92

Xaa Xaa Xaa Xaa Xaa Xaa Xaa Cys Xaa Gly Pro Gly Cys Xaa Xaa
 1               5                  10                  15

Xaa Xaa Xaa Xaa Xaa
                20

<210> SEQ ID NO 93
<211> LENGTH: 20
<212> TYPE: PRT
<213> ORGANISM: Artificial Sequence
<220> FEATURE:
<223> OTHER INFORMATION: synthetic peptide sequence
<220> FEATURE:
<221> NAME/KEY: Mutagen
<222> LOCATION: 1-5, 7, 9, 14-20
<223> OTHER INFORMATION: More than one possible amino acid

<400> SEQUENCE: 93

Xaa Xaa Xaa Xaa Xaa Trp Xaa Cys Xaa Gly Pro Gly Cys Xaa Xaa
 1               5                  10                  15

Xaa Xaa Xaa Xaa Xaa
                20

<210> SEQ ID NO 94
<211> LENGTH: 4
<212> TYPE: PRT
<213> ORGANISM: Artificial Sequence
<220> FEATURE:
<223> OTHER INFORMATION: synthetic peptide sequence

<400> SEQUENCE: 94

Phe Gly Ala His
 1

<210> SEQ ID NO 95
<211> LENGTH: 4
<212> TYPE: PRT
<213> ORGANISM: Artificial Sequence
<220> FEATURE:
<223> OTHER INFORMATION: synthetic peptide sequence

<400> SEQUENCE: 95

Phe Asp Ala His
 1

<210> SEQ ID NO 96
<211> LENGTH: 4
<212> TYPE: PRT
<213> ORGANISM: Artificial Sequence
<220> FEATURE:
<223> OTHER INFORMATION: synthetic peptide sequence

<400> SEQUENCE: 96

Leu Glu Ala His
 1
```

```
<210> SEQ ID NO 97
<211> LENGTH: 4
<212> TYPE: PRT
<213> ORGANISM: Artificial Sequence
<220> FEATURE:
<223> OTHER INFORMATION: synthetic peptide sequence

<400> SEQUENCE: 97

Phe Glu Gly His
  1

<210> SEQ ID NO 98
<211> LENGTH: 4
<212> TYPE: PRT
<213> ORGANISM: Artificial Sequence
<220> FEATURE:
<223> OTHER INFORMATION: synthetic peptide sequence

<400> SEQUENCE: 98

Phe Gly Ala Leu
  1

<210> SEQ ID NO 99
<211> LENGTH: 4
<212> TYPE: PRT
<213> ORGANISM: Artificial Sequence
<220> FEATURE:
<223> OTHER INFORMATION: synthetic peptide sequence

<400> SEQUENCE: 99

Phe Glu Ala Tyr
  1

<210> SEQ ID NO 100
<211> LENGTH: 4
<212> TYPE: PRT
<213> ORGANISM: Artificial Sequence
<220> FEATURE:
<223> OTHER INFORMATION: synthetic peptide sequence

<400> SEQUENCE: 100

Phe Ala Gly His
  1

<210> SEQ ID NO 101
<211> LENGTH: 4
<212> TYPE: PRT
<213> ORGANISM: Artificial Sequence
<220> FEATURE:
<223> OTHER INFORMATION: synthetic peptide sequence

<400> SEQUENCE: 101

Phe Glu Ala Phe
  1

<210> SEQ ID NO 102
<211> LENGTH: 4
<212> TYPE: PRT
<213> ORGANISM: Artificial Sequence
<220> FEATURE:
<223> OTHER INFORMATION: synthetic peptide sequence

<400> SEQUENCE: 102

Gln Ala Cys Met
  1
```

```
<210> SEQ ID NO 103
<211> LENGTH: 4
<212> TYPE: PRT
<213> ORGANISM: Artificial Sequence
<220> FEATURE:
<223> OTHER INFORMATION: synthetic peptide sequence

<400> SEQUENCE: 103

Leu Gln Cys Trp
  1

<210> SEQ ID NO 104
<211> LENGTH: 4
<212> TYPE: PRT
<213> ORGANISM: Artificial Sequence
<220> FEATURE:
<223> OTHER INFORMATION: synthetic peptide sequence

<400> SEQUENCE: 104

Met Ser Cys Val
  1

<210> SEQ ID NO 105
<211> LENGTH: 4
<212> TYPE: PRT
<213> ORGANISM: Artificial Sequence
<220> FEATURE:
<223> OTHER INFORMATION: synthetic peptide sequence

<400> SEQUENCE: 105

Leu Arg Cys Ile
  1

<210> SEQ ID NO 106
<211> LENGTH: 4
<212> TYPE: PRT
<213> ORGANISM: Artificial Sequence
<220> FEATURE:
<223> OTHER INFORMATION: synthetic peptide sequence

<400> SEQUENCE: 106

Gln Ala Cys Leu
  1

<210> SEQ ID NO 107
<211> LENGTH: 4
<212> TYPE: PRT
<213> ORGANISM: Artificial Sequence
<220> FEATURE:
<223> OTHER INFORMATION: synthetic peptide sequence

<400> SEQUENCE: 107

Leu Ser Cys Leu
  1

<210> SEQ ID NO 108
<211> LENGTH: 4
<212> TYPE: PRT
<213> ORGANISM: Artificial Sequence
<220> FEATURE:
<223> OTHER INFORMATION: synthetic peptide sequence

<400> SEQUENCE: 108

Ile Gly Cys Leu
  1

<210> SEQ ID NO 109
```

```
<211> LENGTH: 4
<212> TYPE: PRT
<213> ORGANISM: Artificial Sequence
<220> FEATURE:
<223> OTHER INFORMATION: synthetic peptide sequence

<400> SEQUENCE: 109

Leu Ala Cys Leu
 1

<210> SEQ ID NO 110
<211> LENGTH: 4
<212> TYPE: PRT
<213> ORGANISM: Artificial Sequence
<220> FEATURE:
<223> OTHER INFORMATION: synthetic peptide sequence

<400> SEQUENCE: 110

Leu Ser Cys Ile
 1

<210> SEQ ID NO 111
<211> LENGTH: 4
<212> TYPE: PRT
<213> ORGANISM: Artificial Sequence
<220> FEATURE:
<223> OTHER INFORMATION: synthetic peptide sequence

<400> SEQUENCE: 111

Met Asn Cys Leu
 1

<210> SEQ ID NO 112
<211> LENGTH: 4
<212> TYPE: PRT
<213> ORGANISM: Artificial Sequence
<220> FEATURE:
<223> OTHER INFORMATION: synthetic peptide sequence

<400> SEQUENCE: 112

Leu Arg Cys Leu
 1

<210> SEQ ID NO 113
<211> LENGTH: 4
<212> TYPE: PRT
<213> ORGANISM: Artificial Sequence
<220> FEATURE:
<223> OTHER INFORMATION: synthetic peptide sequence

<400> SEQUENCE: 113

Leu Lys Cys Leu
 1

<210> SEQ ID NO 114
<211> LENGTH: 4
<212> TYPE: PRT
<213> ORGANISM: Artificial Sequence
<220> FEATURE:
<223> OTHER INFORMATION: synthetic peptide sequence

<400> SEQUENCE: 114

Leu Gly Cys Leu
 1

<210> SEQ ID NO 115
<211> LENGTH: 4
```

```
<212> TYPE: PRT
<213> ORGANISM: Artificial Sequence
<220> FEATURE:
<223> OTHER INFORMATION: synthetic peptide sequence

<400> SEQUENCE: 115

Leu Asn Cys Ile
  1

<210> SEQ ID NO 116
<211> LENGTH: 4
<212> TYPE: PRT
<213> ORGANISM: Artificial Sequence
<220> FEATURE:
<223> OTHER INFORMATION: synthetic peptide sequence

<400> SEQUENCE: 116

Met Gly Cys Leu
  1

<210> SEQ ID NO 117
<211> LENGTH: 4
<212> TYPE: PRT
<213> ORGANISM: Artificial Sequence
<220> FEATURE:
<223> OTHER INFORMATION: synthetic peptide sequence

<400> SEQUENCE: 117

Met Ala Cys Leu
  1

<210> SEQ ID NO 118
<211> LENGTH: 4
<212> TYPE: PRT
<213> ORGANISM: Artificial Sequence
<220> FEATURE:
<223> OTHER INFORMATION: synthetic peptide sequence

<400> SEQUENCE: 118

Cys Ala Trp Cys
  1

<210> SEQ ID NO 119
<211> LENGTH: 4
<212> TYPE: PRT
<213> ORGANISM: Artificial Sequence
<220> FEATURE:
<223> OTHER INFORMATION: synthetic peptide sequence

<400> SEQUENCE: 119

Cys Ser Trp Cys
  1

<210> SEQ ID NO 120
<211> LENGTH: 4
<212> TYPE: PRT
<213> ORGANISM: Artificial Sequence
<220> FEATURE:
<223> OTHER INFORMATION: synthetic peptide sequence

<400> SEQUENCE: 120

Cys Glu Pro Cys
  1

<210> SEQ ID NO 121
<211> LENGTH: 4
<212> TYPE: PRT
```

```
<213> ORGANISM: Artificial Sequence
<220> FEATURE:
<223> OTHER INFORMATION: synthetic peptide sequence

<400> SEQUENCE: 121

Cys Asp Trp Cys
  1

<210> SEQ ID NO 122
<211> LENGTH: 4
<212> TYPE: PRT
<213> ORGANISM: Artificial Sequence
<220> FEATURE:
<223> OTHER INFORMATION: synthetic peptide sequence

<400> SEQUENCE: 122

Cys Glu Trp Cys
  1

<210> SEQ ID NO 123
<211> LENGTH: 4
<212> TYPE: PRT
<213> ORGANISM: Artificial Sequence
<220> FEATURE:
<223> OTHER INFORMATION: synthetic peptide sequence

<400> SEQUENCE: 123

Cys Asn Trp Cys
  1

<210> SEQ ID NO 124
<211> LENGTH: 4
<212> TYPE: PRT
<213> ORGANISM: Artificial Sequence
<220> FEATURE:
<223> OTHER INFORMATION: synthetic peptide sequence

<400> SEQUENCE: 124

Cys Gly Trp Cys
  1

<210> SEQ ID NO 125
<211> LENGTH: 27
<212> TYPE: PRT
<213> ORGANISM: Artificial Sequence
<220> FEATURE:
<223> OTHER INFORMATION: synthetic peptide sequence
<220> FEATURE:
<221> NAME/KEY: Mutagen
<222> LOCATION: 2-7, 9-14, 17-19, 21-26
<223> OTHER INFORMATION: More than one possible amino acid

<400> SEQUENCE: 125

Cys Xaa Xaa Xaa Xaa Xaa Xaa Cys Xaa Xaa Xaa Xaa Xaa Xaa Cys
  1               5                  10                  15

Cys Xaa Xaa Xaa Cys Xaa Xaa Xaa Xaa Xaa Xaa Cys
                20                  25

<210> SEQ ID NO 126
<211> LENGTH: 27
<212> TYPE: PRT
<213> ORGANISM: Artificial Sequence
<220> FEATURE:
<223> OTHER INFORMATION: synthetic peptide sequence
<220> FEATURE:
<221> NAME/KEY: Mutagen
<222> LOCATION: 1-10, 12, 14, 21-27
<223> OTHER INFORMATION: More than one possible amino acid
```

-continued

```
<400> SEQUENCE: 126

Xaa Xaa Xaa Xaa Xaa Xaa Xaa Xaa Xaa Xaa Glu Xaa Trp Xaa Cys
 1               5                  10                  15

Cys Gly Pro Gly Cys Xaa Xaa Xaa Xaa Xaa Xaa Xaa
                20                  25

<210> SEQ ID NO 127
<211> LENGTH: 10
<212> TYPE: PRT
<213> ORGANISM: Artificial Sequence
<220> FEATURE:
<223> OTHER INFORMATION: synthetic peptide sequence
<220> FEATURE:
<221> NAME/KEY: Mutagen
<222> LOCATION: 2, 5-7, 9
<223> OTHER INFORMATION: More than one possible amino acid

<400> SEQUENCE: 127

Cys Xaa Trp Val Xaa Xaa Xaa Cys Xaa Gly
 1               5                  10

<210> SEQ ID NO 128
<211> LENGTH: 10
<212> TYPE: PRT
<213> ORGANISM: Artificial Sequence
<220> FEATURE:
<223> OTHER INFORMATION: synthetic peptide sequence
<220> FEATURE:
<221> NAME/KEY: Mutagen
<222> LOCATION: 6-7
<223> OTHER INFORMATION: More than one possible amino acid

<400> SEQUENCE: 128

Cys Ala Trp Val Leu Xaa Xaa Cys Gly Gly
 1               5                  10

<210> SEQ ID NO 129
<211> LENGTH: 6
<212> TYPE: PRT
<213> ORGANISM: Artificial Sequence
<220> FEATURE:
<223> OTHER INFORMATION: synthetic peptide sequence

<400> SEQUENCE: 129

Gly Gly Gly Ser Gly Gly
 1               5

<210> SEQ ID NO 130
<211> LENGTH: 6
<212> TYPE: PRT
<213> ORGANISM: Artificial Sequence
<220> FEATURE:
<223> OTHER INFORMATION: synthetic peptide sequence

<400> SEQUENCE: 130

Gly Gly Gly Ser Ser Gly
 1               5

<210> SEQ ID NO 131
<211> LENGTH: 6
<212> TYPE: PRT
<213> ORGANISM: Artificial Sequence
<220> FEATURE:
<223> OTHER INFORMATION: synthetic peptide sequence

<400> SEQUENCE: 131
```

```
Gly Gly Gly Arg Gly Gly
  1               5
```

<210> SEQ ID NO 132
<211> LENGTH: 20
<212> TYPE: PRT
<213> ORGANISM: Artificial Sequence
<220> FEATURE:
<223> OTHER INFORMATION: synthetic peptide sequence

<400> SEQUENCE: 132

```
Tyr Glu Val Glu Ala Trp Asp Cys Met Gly Pro Gly Cys Ala Asn
  1               5                  10                  15

Leu Phe Glu Ala His
                 20
```

<210> SEQ ID NO 133
<211> LENGTH: 20
<212> TYPE: PRT
<213> ORGANISM: Artificial Sequence
<220> FEATURE:
<223> OTHER INFORMATION: synthetic peptide sequence

<400> SEQUENCE: 133

```
Ser Ser Glu Cys Ala Cys Asp Lys Gly Gly Arg Arg Val Leu Cys
  1               5                  10                  15

Ile Asn Lys Val Gly
                 20
```

<210> SEQ ID NO 134
<211> LENGTH: 20
<212> TYPE: PRT
<213> ORGANISM: Artificial Sequence
<220> FEATURE:
<223> OTHER INFORMATION: synthetic peptide sequence

<400> SEQUENCE: 134

```
Glu Pro His Gly Cys Ser Leu Trp Asp Trp Glu Leu Arg Thr Cys
  1               5                  10                  15

Ser Glu Tyr Ala Asn
                 20
```

<210> SEQ ID NO 135
<211> LENGTH: 20
<212> TYPE: PRT
<213> ORGANISM: Artificial Sequence
<220> FEATURE:
<223> OTHER INFORMATION: synthetic peptide sequence

<400> SEQUENCE: 135

```
Lys Glu Arg Pro Cys Ala Gly Asp Ala Pro Arg Lys Gly Val Cys
  1               5                  10                  15

His Val Ala Thr His
                 20
```

<210> SEQ ID NO 136
<211> LENGTH: 20
<212> TYPE: PRT
<213> ORGANISM: Artificial Sequence
<220> FEATURE:
<223> OTHER INFORMATION: synthetic peptide sequence

<400> SEQUENCE: 136

```
Lys Val Arg Ser Cys Ile Glu Glu Ser Leu Asp Thr Arg Arg Cys
  1               5                  10                  15
```

```
Tyr Leu Val Val Glu
            20

<210> SEQ ID NO 137
<211> LENGTH: 20
<212> TYPE: PRT
<213> ORGANISM: Artificial Sequence
<220> FEATURE:
<223> OTHER INFORMATION: synthetic peptide sequence

<400> SEQUENCE: 137

Ala Lys Thr Ser Ser Cys Gly Glu His Glu Glu Arg Arg Ala Val
 1               5                  10                  15

Cys Val Leu Ser Arg
            20

<210> SEQ ID NO 138
<211> LENGTH: 8
<212> TYPE: PRT
<213> ORGANISM: Artificial Sequence
<220> FEATURE:
<223> OTHER INFORMATION: synthetic peptide sequence

<400> SEQUENCE: 138

Lys Val Trp Ser Val Gln Ser Pro
 1               5

<210> SEQ ID NO 139
<211> LENGTH: 8
<212> TYPE: PRT
<213> ORGANISM: Artificial Sequence
<220> FEATURE:
<223> OTHER INFORMATION: synthetic peptide sequence

<400> SEQUENCE: 139

Gly Lys Val Gln Arg Cys Ile Pro
 1               5

<210> SEQ ID NO 140
<211> LENGTH: 10
<212> TYPE: PRT
<213> ORGANISM: Artificial Sequence
<220> FEATURE:
<223> OTHER INFORMATION: synthetic peptide sequence

<400> SEQUENCE: 140

Gln Thr Cys Arg Arg Val Leu Cys Leu Pro
 1               5                  10

<210> SEQ ID NO 141
<211> LENGTH: 8
<212> TYPE: PRT
<213> ORGANISM: Artificial Sequence
<220> FEATURE:
<223> OTHER INFORMATION: synthetic peptide sequence

<400> SEQUENCE: 141

Arg Val Trp Thr Trp Arg Trp Asn
 1               5

<210> SEQ ID NO 142
<211> LENGTH: 9
<212> TYPE: PRT
<213> ORGANISM: Artificial Sequence
<220> FEATURE:
<223> OTHER INFORMATION: synthetic peptide sequence
```

```
<400> SEQUENCE: 142

Arg Ile Cys Thr Thr Pro Cys Ala Val
  1               5

<210> SEQ ID NO 143
<211> LENGTH: 10
<212> TYPE: PRT
<213> ORGANISM: Artificial Sequence
<220> FEATURE:
<223> OTHER INFORMATION: synthetic peptide sequence

<400> SEQUENCE: 143

Thr Ser Cys Arg Arg Val Phe Cys Ala Val
  1               5                  10

<210> SEQ ID NO 144
<211> LENGTH: 8
<212> TYPE: PRT
<213> ORGANISM: Artificial Sequence
<220> FEATURE:
<223> OTHER INFORMATION: synthetic peptide sequence

<400> SEQUENCE: 144

Arg Val Cys Thr Gly Cys Val Thr
  1               5

<210> SEQ ID NO 145
<211> LENGTH: 10
<212> TYPE: PRT
<213> ORGANISM: Artificial Sequence
<220> FEATURE:
<223> OTHER INFORMATION: synthetic peptide sequence

<400> SEQUENCE: 145

Lys Val Cys Thr Arg Val Cys Cys Gly Thr
  1               5                  10

<210> SEQ ID NO 146
<211> LENGTH: 11
<212> TYPE: PRT
<213> ORGANISM: Artificial Sequence
<220> FEATURE:
<223> OTHER INFORMATION: synthetic peptide sequence

<400> SEQUENCE: 146

His Pro Cys His Met Arg Val Leu Cys Ala Ala
  1               5                  10

<210> SEQ ID NO 147
<211> LENGTH: 13
<212> TYPE: PRT
<213> ORGANISM: Artificial Sequence
<220> FEATURE:
<223> OTHER INFORMATION: synthetic peptide sequence

<400> SEQUENCE: 147

Arg Gly Cys Lys Ala Thr Gly Lys Val Leu Cys Ser Leu
  1               5                  10

<210> SEQ ID NO 148
<211> LENGTH: 12
<212> TYPE: PRT
<213> ORGANISM: Artificial Sequence
<220> FEATURE:
<223> OTHER INFORMATION: synthetic peptide sequence
```

```
<400> SEQUENCE: 148

Ser Gly Cys Leu Arg Ala Val Gly Ala Cys Asn Thr
 1               5                  10

<210> SEQ ID NO 149
<211> LENGTH: 11
<212> TYPE: PRT
<213> ORGANISM: Artificial Sequence
<220> FEATURE:
<223> OTHER INFORMATION: synthetic peptide sequence

<400> SEQUENCE: 149

Ala Gly Cys Gly Ser Lys Ala Val Cys Val Ser
 1               5                  10

<210> SEQ ID NO 150
<211> LENGTH: 10
<212> TYPE: PRT
<213> ORGANISM: Artificial Sequence
<220> FEATURE:
<223> OTHER INFORMATION: synthetic peptide sequence

<400> SEQUENCE: 150

Arg Val Trp Thr Ala Pro Gln Cys Leu Ile
 1               5                  10

<210> SEQ ID NO 151
<211> LENGTH: 11
<212> TYPE: PRT
<213> ORGANISM: Artificial Sequence
<220> FEATURE:
<223> OTHER INFORMATION: synthetic peptide sequence

<400> SEQUENCE: 151

Lys Val Cys His Ala Ser Ser Gly Cys Val Ala
 1               5                  10

<210> SEQ ID NO 152
<211> LENGTH: 11
<212> TYPE: PRT
<213> ORGANISM: Artificial Sequence
<220> FEATURE:
<223> OTHER INFORMATION: synthetic peptide sequence

<400> SEQUENCE: 152

Arg Ala Cys Gln Arg Ala Cys Leu Cys Pro Ala
 1               5                  10

<210> SEQ ID NO 153
<211> LENGTH: 16
<212> TYPE: PRT
<213> ORGANISM: Artificial Sequence
<220> FEATURE:
<223> OTHER INFORMATION: synthetic peptide sequence

<400> SEQUENCE: 153

Arg Ser Cys Ala Asp Val Ala Ser Arg Cys Trp Glu His Cys Ile
 1               5                  10                  15

Thr

<210> SEQ ID NO 154
<211> LENGTH: 16
<212> TYPE: PRT
<213> ORGANISM: Artificial Sequence
<220> FEATURE:
<223> OTHER INFORMATION: synthetic peptide sequence
```

<400> SEQUENCE: 154

Thr Asp Cys Gly Arg Val Ala Ser Val Cys Trp Glu Ser Cys Leu
 1               5                  10                  15

Ile

<210> SEQ ID NO 155
<211> LENGTH: 19
<212> TYPE: PRT
<213> ORGANISM: Artificial Sequence
<220> FEATURE:
<223> OTHER INFORMATION: synthetic peptide sequence

<400> SEQUENCE: 155

Cys Cys Glu Thr Arg Trp Trp Cys Gln Trp Gly Phe Cys Ser Gly
 1               5                  10                  15

Ser Ala Cys Cys

<210> SEQ ID NO 156
<211> LENGTH: 12
<212> TYPE: PRT
<213> ORGANISM: Artificial Sequence
<220> FEATURE:
<223> OTHER INFORMATION: synthetic peptide sequence

<400> SEQUENCE: 156

Gly Cys Lys Arg Val Cys Ser Leu Gly Val Met Cys
 1               5                  10

<210> SEQ ID NO 157
<211> LENGTH: 27
<212> TYPE: PRT
<213> ORGANISM: Artificial Sequence
<220> FEATURE:
<223> OTHER INFORMATION: synthetic peptide sequence

<400> SEQUENCE: 157

Cys Ser Trp Val Leu Val Gln Cys Gly Gly Glu Trp Trp His Cys
 1               5                  10                  15

Cys Gly Leu Gly Cys Gly Leu Val Val Asn Ala Cys
                 20                  25

<210> SEQ ID NO 158
<211> LENGTH: 21
<212> TYPE: PRT
<213> ORGANISM: Artificial Sequence
<220> FEATURE:
<223> OTHER INFORMATION: synthetic peptide sequence

<400> SEQUENCE: 158

Cys Gly Cys Glu Glu Arg Lys Ala Trp Lys Cys Gln Glu Ala Cys
 1               5                  10                  15

Ala Arg Ser Gly Thr Val
                 20

<210> SEQ ID NO 159
<211> LENGTH: 84
<212> TYPE: DNA
<213> ORGANISM: Artificial Sequence
<220> FEATURE:
<223> OTHER INFORMATION: Synthetic Oligonucleotide

<400> SEQUENCE: 159
cgcgcccagg tgtacgagtc ctggggatgc atcggccccg gctgcgcctg            50

-continued

```
cctgcaggcc tgcctgggag gcgggagctc cggc                              84
```

<210> SEQ ID NO 160
<211> LENGTH: 80
<212> TYPE: DNA
<213> ORGANISM: Artificial Sequence
<220> FEATURE:
<223> OTHER INFORMATION: Synthetic Oligonucleotide

<400> SEQUENCE: 160

```
gccggagctc ccgcctccca ggcaggcctg caggcaggcg cagccggggc            50
cgatgcatcc ccaggactcg tacacctggg                                  80
```

<210> SEQ ID NO 161
<211> LENGTH: 20
<212> TYPE: PRT
<213> ORGANISM: Artificial Sequence
<220> FEATURE:
<223> OTHER INFORMATION: synthetic peptide sequence
<220> FEATURE:
<221> NAME/KEY: Mutagen
<222> LOCATION: 1-7, 14-20
<223> OTHER INFORMATION: More than one possible amino acid

<400> SEQUENCE: 161

Xaa Xaa Xaa Xaa Xaa Xaa Xaa Cys Ile Gly Pro Gly Cys Xaa Xaa
 1               5                  10                  15

Xaa Xaa Xaa Xaa Xaa
                20

<210> SEQ ID NO 162
<211> LENGTH: 10
<212> TYPE: PRT
<213> ORGANISM: Artificial Sequence
<220> FEATURE:
<223> OTHER INFORMATION: synthetic peptide sequence
<220> FEATURE:
<221> NAME/KEY: Mutagen
<222> LOCATION: 6-7
<223> OTHER INFORMATION: More than one possible amino acid

<400> SEQUENCE: 162

Cys Ser Trp Val Leu Xaa Xaa Cys Gly Gly
 1               5                  10